US007973143B2

(12) United States Patent
Saba et al.

(10) Patent No.: US 7,973,143 B2
(45) Date of Patent: *Jul. 5, 2011

(54) SPHINGOSINE-1-PHOSPHATE LYASE POLYPEPTIDES, POLYNUCLEOTIDES AND MODULATING AGENTS AND METHODS OF USE THEREFOR

(75) Inventors: Julie D. Saba, Oakland, CA (US); Jianhui Zhou, Redwood City, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 45 days.

This patent is subject to a terminal disclaimer.

(21) Appl. No.: 12/341,520

(22) Filed: Dec. 22, 2008

(65) Prior Publication Data

US 2009/0203044 A1 Aug. 13, 2009

Related U.S. Application Data

(63) Continuation of application No. 11/782,458, filed on Jul. 24, 2007, now abandoned, which is a continuation of application No. 10/979,085, filed on Nov. 1, 2004, now Pat. No. 7,262,044, which is a continuation of application No. 10/053,510, filed on Jan. 17, 2002, now Pat. No. 6,830,881, which is a continuation-in-part of application No. 09/356,643, filed on Jul. 19, 1999, now Pat. No. 6,569,666, which is a continuation-in-part of application No. 08/939,309, filed on Sep. 29, 1997, now Pat. No. 6,423,527.

(51) Int. Cl.
*C07K 16/40* (2006.01)
*C07K 16/00* (2006.01)
*G01N 33/573* (2006.01)

(52) U.S. Cl. ............. 530/388.26; 530/387.1; 530/388.1; 435/7.4; 435/810

(58) Field of Classification Search .................. None
See application file for complete search history.

(56) References Cited

U.S. PATENT DOCUMENTS

| | | | |
|---|---|---|---|
| 5,430,169 A | 7/1995 | Boumendjel et al. | 558/169 |
| 6,187,562 B1 | 2/2001 | Duckworth et al. | 435/69.1 |
| 6,423,527 B1 | 7/2002 | Saba et al. | 435/232 |
| 6,495,359 B1 | 12/2002 | Saba et al. | 435/232 |
| 6,569,666 B1 | 5/2003 | Saba | 435/232 |
| 6,830,881 B2 | 12/2004 | Saba et al. | 435/4 |
| 6,858,427 B2 | 2/2005 | Gerritsen et al. | 435/325 |
| 7,041,291 B2 | 5/2006 | Saba et al. | 424/139.1 |
| 7,262,044 B2 | 8/2007 | Saba et al. | 435/232 |
| 7,674,580 B2 | 3/2010 | Saba et al. | 435/6 |
| 2003/0054366 A1 | 3/2003 | Schlegel et al. | 435/6 |
| 2003/0059922 A1 | 3/2003 | Saba et al. | 435/232 |
| 2003/0175939 A1 | 9/2003 | Saba et al. | 435/232 |
| 2003/0215805 A1 | 11/2003 | Lillie et al. | 435/6 |
| 2003/0219782 A1 | 11/2003 | Saba et al. | 435/6 |
| 2004/0005563 A1 | 1/2004 | Mack et al. | 435/6 |
| 2004/0029114 A1 | 2/2004 | Mack et al. | 435/6 |
| 2004/0110197 A1 | 6/2004 | Skinner et al. | 435/6 |
| 2005/0221346 A1 | 10/2005 | Saba et al. | 435/6 |
| 2006/0252035 A1 | 11/2006 | Friedman et al. | 435/6 |
| 2008/0085995 A1 | 4/2008 | Saba et al. | 536/23.1 |

FOREIGN PATENT DOCUMENTS

| | | |
|---|---|---|
| WO | WO 93/19760 | 10/1993 |
| WO | WO 95/21848 | 8/1995 |
| WO | WO 99/16888 | 4/1999 |
| WO | WO 99/38983 | 8/1999 |
| WO | WO 99/61581 | 12/1999 |
| WO | WO 00/70028 | 11/2000 |
| WO | WO 01/31029 | 5/2001 |
| WO | WO 01/42479 | 6/2001 |
| WO | WO 01/49879 | 7/2001 |
| WO | WO 01/85953 | 11/2001 |
| WO | WO 02/27028 | 4/2002 |
| WO | WO 03/062390 | 7/2003 |

OTHER PUBLICATIONS

Attwood Science 290: 471-473, 2000.*
Skolnick et al. Trends in Biotech. 18: 34-39, 2000.*
Lederman et al. Molecular Immunology 28: 1171-1181, 1991.*
Li et al. PNAS 77: 3211-3214, 1980.*
Houghten et al. New Approaches to Immunization, Vaccines 86, Cold Spring Harbor Laboratory, p. 21-25, 1986.*
Adachi-Yamada et al., "De Novo Synthesis of Sphingolipids Is Required for Cell Survival by Down-Regulating c-Jun N-Terminal Kinase in *Drosophila* Imaginal Discs," *Molecular and Cellular Biology* 19(10):7276-7286, Oct. 1999.
Adams et al., GenBank Accession No. AA338781, Apr. 18, 1997, 2 pages.
Amalfitano et al., "Fluorescence in situ hybridization study of aneuploidy of chromosomes 7, 10, X, and Y in primary and secondary glioblastomas," *Cancer Genet Cytogenet* 116:6-9, 2000. Amann et al., "Tightly regulated *tac* promoter vectors useful for the expression of unfused and fused proteins in *Escherichia coli*," *Gene* 69(2):301-315, Sep. 30, 1988.
Bejaoui et al., "SPTLC1 is mutated in hereditary sensory neuropathy, type 1," *Nature Genetics* 27(3):261-262, Mar. 2001.
Branden et al., "Prediction, Engineering, and Design of Protein Structures," Introduction to Protein Structure, Garland Publishing, Inc., New York, p. 247, 1991.
Broun et al., "Catalytic Plasticity of Fatty Acid Modification Enzymes Underlying Chemical Diversity of Plant Lipids," *Science* 282:1315-1317, Nov. 13, 1998.
Caligan et al., "A High-Performance Liquid Chromatographic Method to Measure Sphingosine 1-Phosphate and Related Compounds from Sphingosine Kinase Assays and Other Biological Samples," *Analytical Biochemistry* 281(1):36-44, May 15, 2000.
Dawkins et al., "Mutations in *SPTLC1*, encoding serine palmitoyltransferase, long chain base subunit-1, cause hereditary sensory neuropathy type I," *Nature Genetics* 27(3):309-312, Mar. 2001.

(Continued)

*Primary Examiner* — Sharon Wen

(74) *Attorney, Agent, or Firm* — Seed IP Law Group PLLC

(57) ABSTRACT

Compositions, methods and kits for diagnosing and treating cancer are provided. Therapeutic compositions may comprise agents that modulate the expression or activity of a sphingosine-1-phosphate lyase (SPL). Such compositions may be administered to a mammal afflicted with cancer. Diagnostic methods and kits may employ an agent suitable for detecting alterations in endogenous SPL. Such methods and kits may be used to detect the presence of a cancer or to evaluate the prognosis of a known disease. SPL polypeptides, polynucleotides and antibodies are also provided.

7 Claims, No Drawings

OTHER PUBLICATIONS

Fulton, GenBank Database, Accession No. U51031, Mar. 23, 1996, 5 pages.

Fulton, GenBank Database, Accession No. S70123, May 1996, 1 page.

Fyrst et al., "The *PLB2* Gene of *Saccharomyces cerevisiae* Confers Resistance to Lysophophatidylcholine and Encodes a Phospholipase B/Lysophospholipase," *Biochemistry* 38(18):5864-5871, May 4, 1999.

Gable et al., "Mutations in the Yeast *LCB1* and *LCB2* Genes, Including Those Corresponding to the Hereditary Sensory Neuropathy Type I Mutations, Dominantly Inactivate Serine Palmitoyltransferase," *The Journal of Biological Chemistry* 277(12):10194-10200, Mar. 22, 2002.

GenBank Accession No. GI:1855648, Aug. 1997, 2 pages.

Genbank Accession No. GI:5532486, Apr. 20, 1999, 2 pages.

Genbank Accession No. GI:8133099, May 11, 2000, 2 pages.

Gottlieb et al., "The *DPL1* Gene Is Involved in Mediating the Response to Nutrient Deprivation in *Saccharomyces cerevisiae*," *Molecular Cell Biology Research Communications* 1(1):66-71, Apr. 1999.

Hannun et al., "Enzymes of Sphingolipid Metabolism: From Modular to Integrative Signaling," *Biochemistry* 40(16):4893-4903, Apr. 24, 2001.

Heitman et al., "FK 506-binding protein proline rotamase is a target for the immunosuppressive agent FK 506 in *Saccharomyces cerevisiae*," *Proc. Natl. Acad. Sci. USA* 88:1948-1952, Mar. 1991.

Herr et al., "*Sply* regulation of sphingolipid signaling molecules is essential for *Drosophila* development," *Development* 130:2443-2453, 2003.

Hillier et al., GenBank Database, Accession No. T86263, Mar. 1995, 2 pages.

Ikeda et al., "Sphingosine-1-phosphate lyase SPL is an endoplasmic reticulum-resident, integral membrane protein with the pyridoxal 5'-phosphate binding domain exposed to the cytosol," *Biochemical and Biophysical Research Communications* 325:338-343, 2004.

Ioannidis, "Replication validity of genetic association studies," *Nature Genetics* 29:306-309, 2001.

Kim et al., "Accumulation of Phosphorylated Sphingoid Long Chain Bases Results in Cell Growth Inhibition in *Saccharomyces cerevisiae*," *Genetics* 156:1519-1529, Dec. 2000.

Kohara, GenBank Database, Accession No. D66593, Dec. 13, 1995, 2 pages.

Lanterman et al., "Characterization of sphingosine kinase (SK) activity in *Saccharomyces cerevisiae* and isolation of SK-deficient mutants," *Biochem. J.* 332:525-531, 1998.

Lucentini et al., "Gene Association Studies Typically Wrong," *The Scientist* 18(24), 6 pages, 2004.

Mao et al., "The dihydrosphingosine-1-phosphate phosphatases of *Saccharomyces cerevisiae* are important regulators of cell proliferation and heat stress responses," *Biochem. J.* 342:667-675, 1999.

Marra et al., GenBank Database, Accession No. AA107456, Nov. 6, 1996, 2 pages.

Marra et al., GenBank Database, Accession No. AA589412, Sep. 18, 1997, 2 pages.

Marra et al., GenBank Database, Accession No. WO8172, Sep. 5, 1996, 2 pages.

Melendez et al., "Human sphingosine kinase: molecular cloning, functional characterization and tissue distribution," *Gene* 251:19-26, 2000.

Mendel et al., "Sphingosine Phosphate Lyase Expression Is Essential for Normal Development in *Caenorhabditis elegans*," *The Journal of Biological Chemistry* 278(25):22341-22349, Jun. 20, 2003.

Olivera et al., "Sphingosine-1-phosphate as second messenger in cell proliferation induced by PDGF and FCS mitogens," *Nature* 365:557-560, Oct. 7, 1993.

Oskouian et al., "Sphingosine-1-phosphate lyase potentiates apoptosis via p53- and p38-dependent pathways and is down-regulated in colon cancer," *PNAS* 103(46):17384-17389, 2006.

Pyne et al., "Sphingosine 1-phosphate signaling in mammalian cells," *Biochem J.* 349:385-402, 2000.

Pyne et al., "Sphingosine 1-phosphate signalling via the endothelial differentiation gene family of G-protein-coupled receptors," *Pharmacology & Therapeutics* 88:115-131, 2000.

Qie et al., "Identification of a *Saccaromyces* Gene, *LCB3*, Necessary for Incorporation of Exogenous Long Chain Bases into Sphingolipids," *J. Biol. Chem.*, 272(26):16110-16117, Jun. 27, 1997.

Reiss et al., "Sphingosine-phosphate Lyase Enhances Stress-induced Ceramide Generation and Apoptosis," *J. Biol. Chem.* 279(2):1281-1290, 2004.

Roseman et al., "A *P* Element Containing *suppressor of Hairy-wing* Binding Regions Has Novel Properties for Mutagenesis in *Drosophila melanogaster*," *Genetics* 141:1061-1074, Nov. 1995.

Saba et al., "Ceramide: an intracellular mediator of apopotosis and growth suppression," *Phil. Trans. R. Soc. Lond. B* 351:233-244, 1996, 9 pages.

Saba et al., "The *BST1* Gene of *Saccharomyces cerevisiae* Is the Sphingosine-1-phosphate Lyase," *The Journal of Biological Chemistry* 272(42):26087-26090, Oct. 17, 1997.

Sadahira et al., "Sphingosine 1-phosphate, a specific endogenous signaling molecule controlling cell motility and tumor cell invasiveness," *Proc. Natl. Acad. Sci. USA* 89(20):9686-9690, Oct. 15, 1992.

Seffernick et al., "Melamine Deaminase and Atrazine Chlorohydrolase: 98 Percent Identical but Functionally Different," *J. Bacteriol.* 183(8):2405-2410, Apr. 2001.

Spiegel et al., "Sphingosine-1-phosphate, a novel second messenger involved in cell growth regulation and signal transduction, affects growth and invasiveness of human breast cancer cells," *Breast Cancer Research and Treatment* 31:337-348, 1994.

Thompson et al., "p53 gene mRNA expression and chromosome 17p allele loss in breast cancer," *Br J Cancer* 61:74-78, 1990.

van de Loo et al., "An oleate 12-hydroxylase from *Ricinus communis* L. is a fatty acyl desaturase homolog," *Proc. Natl. Acad. Sci. USA* 92:6743-6747, Jul. 1995.

Van Veldhoven et al., "Human sphingosine-1-phosphate Lyase: cDNA cloning, functional expression studies and mapping to chromosome 10q22[1]," *Biochimica et Biophysica Acta* 1487:128-134, 2000.

Van Veldhoven et al., "Sphingosine-Phosphate Lyase," *Advances in Lipid Research* 26:69-98, 1993.

Van Veldhoven et al., "Subcellular Localization and Membrane Topology of Sphingosine-1-phosphate Lyase in Rat Liver," *J. Biol. Chem.* 266(19):12502-12507, 1991.

Wacholder et al., "Assessing the Probability That a Positive Report is False: An Approach for Molecular Epidemiology Studies," *J Natl Cancer Institute* 96(6):434-442, 2004.

Waterston, GenBank Database, Accession No. AAC69001, Oct. 22, 1998, 2 pages.

Waterston et al., GenBank Database Accession No. AAA92321, Feb. 1996.

Witkowski et al., "Conversion of a β-Ketoacyl Synthase to a Malonyl Decarboxylase by Replacement of the Active-Site Cysteine with Glutamine," *Biochemistry* 38(36):11643-11650, 1999.

Xia et al., "An oncogenic role of sphingosine kinase," *Curr Biol.* 10(23):1527-1530, 2000.

Zhou and Saba, "Identification of the First Mammalian Sphingosine Phosphate Lyase Gene and Its Functional Expression in Yeast," *Biochemical and Biophysical Research Communications* 242(3):502-507, Jan. 26, 1998.

\* cited by examiner

SPHINGOSINE-1-PHOSPHATE LYASE POLYPEPTIDES, POLYNUCLEOTIDES AND MODULATING AGENTS AND METHODS OF USE THEREFOR

CROSS-REFERENCES TO RELATED APPLICATIONS

This application is a continuation of U.S. patent application Ser. No. 11/782,458, filed Jul. 24, 2007, now abandoned; which is a continuation of U.S. patent application Ser. No. 10/979,085, filed Nov. 1, 2004, now U.S. Pat. No. 7,262,044; which is a continuation of U.S. patent application Ser. No. 10/053,510, filed Jan. 17, 2002, now U.S. Pat. No. 6,830,881; which is a continuation-in-part of U.S. patent application Ser. No. 09/356,643, filed Jul. 19, 1999, now U.S. Pat. No. 6,569,666; which is a continuation-in-part of U.S. patent application Ser. No. 08/939,309, filed Sep. 29, 1997, now U.S. Pat. No. 6,423,527, which applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200116_402C6_SEQUENCE_LISTING.txt. The text file is 95 KB, was created on Dec. 22, 2008, and is being submitted electronically via EFS-Web, concurrent with the filing of the specification.

BACKGROUND

1. Technical Field

The present invention relates generally to cancer detection and therapy. The invention is more particularly related to sphingosine-1-phosphate lyase polynucleotides and polypeptides, and to agents that modulate the expression and/or activity of such polypeptides. Such agents may be used, for example, to diagnose and/or treat cancers such as breast and colon cancer.

2. Description of the Related Art

Breast cancer is a significant health problem for women in the United States and throughout the world. Although advances have been made in detection and treatment of the disease, breast cancer remains the most common form of cancer, and the second leading cause of cancer death, in American women. Among African-American women and women between 15 and 54 years of age, breast cancer is the leading cause of cancer death. One out of every eight women in the United States will develop breast cancer, a risk which has increased 52% during 1950-1990. In 1994, it is estimated that 182,000 new cases of female breast cancer were diagnosed, and 46,000 women died from the disease.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. However, the use of established markers often leads to a result that is difficult to interpret.

With current therapies, tumor invasiveness and metastasis is a critical determinant in the outcome for breast cancer patients. Although the five year survival for women diagnosed with localized breast cancer is about 90%, the five year survival drops to 18% for women whose disease has metastasized. Present therapies are inadequate for inhibiting tumor invasiveness for the large population of women with this severe disease.

Colon cancer is the second most frequently diagnosed malignancy in the United States as well as the second most common cause of cancer death. The five-year survival rate for patients with colorectal cancer detected in an early localized stage is 92%; unfortunately, only 37% of colorectal cancer is diagnosed at this stage. The survival rate drops to 64% if the cancer is allowed to spread to adjacent organs or lymph nodes, and to 7% in patients with distant metastases.

The prognosis of colon cancer is directly related to the degree of penetration of the tumor through the bowel wall and the presence or absence of nodal involvement, consequently, early detection and treatment are especially important. Currently, diagnosis is aided by the use of screening assays for fecal occult blood, sigmoidoscopy, colonoscopy and double contrast barium enemas. Treatment regimens are determined by the type and stage of the cancer, and include surgery, radiation therapy and/or chemotherapy. Recurrence following surgery (the most common form of therapy) is a major problem and is often the ultimate cause of death. In spite of considerable research into therapies for the disease, colon cancer remains difficult to diagnose and treat. In spite of considerable research into therapies for these and other cancers, colon cancer remains difficult to diagnose and treat effectively. Accordingly, improvements are needed in the treatment, diagnosis and prevention of breast and colon cancer. The present invention fulfills this need and further provides other related advantages.

BRIEF SUMMARY

Briefly stated, the present invention provides compositions and methods for the diagnosis and therapy of cancer. Within one aspect, the present invention provides isolated polynucleotides comprising a sequence selected from the group consisting of: (a) a sequence shown in SEQ ID NO:15; (b) nucleotide sequences that hybridize to a polynucleotide complementary to a sequence shown in SEQ ID NO:15 under moderately stringent conditions, wherein the nucleotide sequences encode polypeptides having sphingosine-1-phosphate lyase activity; and (c) nucleotide sequences that encode a polypeptide encoded by a sequence shown in SEQ ID NO:15.

Within a related aspect, an isolated polynucleotide is provided that encodes a polypeptide shown in SEQ ID NO:16, or a variant of such a polypeptide that has sphingosine-1-phosphate lyase activity. Recombinant expression vectors comprising any of the foregoing polynucleotides, and host cells transformed or transfected with such expression vectors, are also provided.

Within further aspects, SPL polypeptides are provided. Such polypeptides may be encoded by any of the foregoing polynucleotides. Alternatively, a polypeptide may comprise an amino acid sequence shown in SEQ ID NO:16, or a variant thereof, wherein the polypeptide has sphingosine-1-phosphate lyase activity.

Within a further aspect, the present invention provides isolated polynucleotides comprising at least 100 nucleotides complementary to a sequence shown in SEQ ID NO:15.

Within other aspects, methods are provided for preparing a sphingosine-1-phosphate lyase, comprising culturing a host cell transformed or transfected with a polynucleotide as described above under conditions promoting expression of the polynucleotide and recovering a sphingosine-1-phosphate lyase.

In further aspects, the present invention provides methods for identifying an agent that modulates sphingosine-1-phosphate lyase activity. In one such aspect, the method comprises: (a) contacting a candidate agent with a polypeptide comprising a sequence shown in SEQ ID NO:16, or a variant of such a sequence having sphingosine-1-phosphate lyase activity, wherein the step of contacting is carried out under conditions and for a time sufficient to allow the candidate agent to interact with the polypeptide; and (b) subsequently measuring the ability of the polypeptide to degrade sphingosine-1-phosphate or a derivative thereof, relative to an ability in the absence of candidate agent. The step of contacting may be performed by incubating a cell expressing the polypeptide with the candidate modulator, and the step of measuring the ability to degrade sphingosine-1-phosphate may be performed using an in vitro assay and a cellular extract.

The present invention further provides pharmaceutical compositions comprising an agent that modulates sphingosine-1-phosphate lyase activity in combination with a pharmaceutically acceptable carrier. Such agents preferably increase sphingosine-1-phosphate lyase activity. Such inhibition may be achieved by increasing expression of an endogenous SPL gene, or by increasing the ability of an endogenous SPL to degrade sphingosine-1-phosphate. Within certain preferred embodiments, a modulating agent comprises a polynucleotide or an antibody or an antigen-binding fragment thereof.

Within still further aspects, the present invention provides methods for modulating sphingosine-1-phosphate activity, comprising contacting a sphingosine-1-phosphate lyase with an effective amount of an agent that modulates sphingosine-1-phosphate lyase activity, wherein the step of contacting is performed under conditions and for a time sufficient to allow the agent and the sphingosine-1-phosphate lyase to interact. To modulate sphingosine-1-phosphate lyase activity in a cell, a cell expressing sphingosine-1-phosphate may be contacted with such an agent.

Within related aspects, the present invention provides methods for inhibiting the growth of a cancer cell, comprising contacting a cancer cell with an agent that increases sphingosine-1-phosphate lyase activity. In a preferred embodiment, the cancer cell is a breast cancer cell.

The present invention also provides methods for inhibiting the development and/or metastasis of a cancer in a mammal, comprising administering to a mammal an agent that increases sphingosine-1-phosphate lyase activity. Within certain embodiments, an agent may comprise, or be linked to, a targeting component, such as an anti-tumor antibody or a component that binds to an estrogen receptor.

Within other aspects, methods for diagnosing cancer in a mammal are provided, comprising detecting an alteration in an endogenous sphingosine-1-phosphate lyase gene in a sample obtained from a mammal, and therefrom diagnosing a cancer in the mammal. In certain embodiments the cancer is breast or colon cancer and the sample is a breast tumor biopsy.

In related aspects, the present invention provides methods for evaluating a cancer prognosis, comprising determining the presence or absence of an alteration in an endogenous sphingosine-1-phosphate lyase gene in a sample obtained from a mammal afflicted with cancer, and therefrom determining a prognosis.

The present invention further provides isolated antibodies that bind to a polypeptide having a sequence shown in SEQ ID NO:16. Such antibodies may be polyclonal or monoclonal, and may increase the ability of a polypeptide having a sequence shown in SEQ ID NO:16 degrade sphingosine-1-phosphate.

In still further aspects, the present invention provides methods for detecting sphingosine-1-phosphate lyase in a sample, comprising: (a) contacting a sample with an antibody as described above under conditions and for a time sufficient to allow the antibody to bind to sphingosine-1-phosphate lyase; and (b) detecting in the sample the presence of sphingosine-1-phosphate lyase bound to the antibody.

Kits for use in the above methods are also provided. A kit for detecting sphingosine-1-phosphate lyase in a sample comprises an antibody as described above and a buffer or detection reagent. A kit for detecting an alteration in a sphingosine-1-phosphate gene in a sample comprises a polynucleotide and a detection reagent.

The present invention further provides for a homozygous null mutant *Drosophila melanogaster* fly line the genome of which comprises a P-element transposon insertion in the coding region of the sphingosine phosphate lyase (SPL) gene wherein said gene encodes the sequence set forth in SEQ ID NO:16, and wherein said fly line has a flightless phenotype. In a related embodiment, the homozygous mutant flies demonstrate abnormal developmental patterning of thoracic muscles of the T2 segment.

The present invention also provides methods for testing an agent capable of inhibiting the development and/or metastasis of a cancer in a mammal, comprising contacting SPL mutant *Drosophila* progeny with growth medium comprising a test agent suspected of inhibiting mammalian sphingosine kinase, and detecting the restoration of flight ability in the progeny. In a related embodiment, the homozygous mutant flies used in this method demonstrate abnormal developmental patterning of thoracic muscles of the T2 segment.

The present invention further provides for methods for determining the presence of a cancer in a patient, comprising the steps of: (a) obtaining a biological sample from the patient; (b) contacting the biological sample with at least one oligonucleotide that is at least partially complementary to the sequence set forth in SEQ ID NO:7; (c) detecting in the sample an amount of said oligonucleotide that hybridizes to the polynucleotide; and comparing the amount of oligonucleotide that hybridizes to the polynucleotide to a predetermined cut-off value, and therefrom determining the presence of the cancer in the patient.

BRIEF DESCRIPTION OF THE SEQUENCE IDENTIFIERS

SEQ ID NO:1 is the determined cDNA sequence of *S. cerevisiae* SPL.

SEQ ID NO:2 is the amino acid sequence of *S. cerevisiae* SPL encoded by the polynucleotide sequence set forth in SEQ ID NO:1

SEQ ID NO:3 is the determined cDNA sequence of *C. elegans* SPL.

SEQ ID NO:4 is the amino acid sequence of *C. elegans* SPL encoded by the polynucleotide sequence set forth in SEQ ID NO:3.

SEQ ID NO:5 is the determined cDNA sequence of the mouse SPL.

SEQ ID NO:6 is the amino acid sequence of mouse SPL encoded by the polynucleotide sequence set forth in SEQ ID NO:5.

SEQ ID NO:7 is the determined cDNA sequence of the full-length human SPL.

SEQ ID NO:8 is the amino acid sequence of human SPL encoded by the polynucleotide sequence set forth in SEQ ID NO:7.

SEQ ID NO:9 is the determined cDNA sequence of a human SPL with a deletion.

SEQ ID NO:10 is the amino acid sequence of a human SPL with a deletion, encoded by the polynucleotide sequence set forth in SEQ ID NO:9.

SEQ ID NO:11 is the amino acid sequence of *C. elegans* SPL encoded by the polynucleotide sequence set forth in SEQ ID NO:12.

SEQ ID NO:12 is the determined cDNA sequence of a *C. elegans* SPL.

SEQ ID NO:13 is a PCR primer.

SEQ ID NO:14 is a PCR primer.

SEQ ID NO:15 is the determined cDNA sequence encoding the *Drosophila melanogaster* SPL.

SEQ ID NO:16 is the amino acid sequence of the *Drosophila melanogaster* SPL, encoded by the cDNA sequence set forth in SEQ ID NO:15.

SEQ ID NO:17 is the determined cDNA sequence of a human SPL as set forth in Genbank Accession No: AF144638.

SEQ ID NO:18 is the amino acid sequence of a human SPL encoded by the polynucleotide sequence provided in SEQ ID NO:17.

SEQ ID NO:19 is the amino acid sequence of a first *Drosophila melanogaster* SK protein.

SEQ ID NO:20 is the amino acid sequence of a second *Drosophila melanogaster* SK protein.

SEQ ID NO:21 is the amino acid sequence of a human SK protein.

DETAILED DESCRIPTION

As noted above, the present invention is generally directed to compositions and methods for the diagnosis and therapy of cancers such as breast cancer. The invention is more particularly related to sphingosine-1-phosphate lyase (SPL) polypeptides, which have the ability to cleave sphingosine-1-phosphate into inactive metabolites, and to polynucleotides encoding such polypeptides. Sphingosine-1-phosphate (S-1-P) is an endogenous sphingolipid metabolite present in most mammalian cells and in serum. Like other sphingolipid metabolites such as ceramide and sphingosine, S-1-P participates in specific signal transduction pathways. The results of S-1-P signaling are diverse and dependent upon the cell type being examined. However, many of the effects of S-1-P signaling, which include promotion of cellular proliferation, enhancement of migration, inhibition of apoptosis and stimulation of angiogenesis, influence the transformation, growth, drug resistance, vascularity and metastatic capacity of cancer cells. The gene encoding the enzyme responsible for S-1-P synthesis is sphingosine kinase, SK, and S-1-P degradation is sphingosine phosphate lyase, SPL and S-1-P phosphatase, S-1-PP. Several observations support the notion that SPL may be a cancer related gene. First, altered expression of SPL in human tumors compared to corresponding normal tissue from the same patient has been shown. Second, human SPL maps to 10q21, a chromosomal region frequently deleted in a variety of human cancers. Taken together, these observations raise the possibility that SPL may be potentially effective targets for pharmacological intervention in the treatment of cancer.

Agents that decrease the expression or activity of endogenous SPL polypeptides are encompassed by the present invention. Such modulating agents may be identified using methods described herein and used, for example, in cancer therapy. It has also been found, within the context of the present invention, that the detection of alterations in an endogenous SPL sequence can be used to diagnose cancer, and to assess the prognosis for recovery. The present invention further provides such diagnostic methods and kits.

As used herein, the term "polypeptide" encompasses amino acid chains of any length, including full length endogenous (i.e., native) SPL proteins and variants of endogenous sequences. "Variants" are polypeptides that differ in sequence from a native SPL only in substitutions, deletions and/or other modifications, such that the variant retains SPL activity, which may be determined using a representative method described herein SPL polypeptide variants generally encompassed by the present invention will typically exhibit at least about 70%, 75%, 80%, 85%, 90%, 91%, 92%, 93%, 94%, 95%, 96%, 97%, 98%, or 99% or more identity along its length, to an SPL polypeptide sequence set forth herein. Within an SPL polypeptide variant, amino acid substitutions are preferably made at no more than 50% of the amino acid residues in the native polypeptide, and more preferably at no more than 25% of the amino acid residues. Such substitutions are preferably conservative. A conservative substitution is one in which an amino acid is substituted for another amino acid that has similar properties, such that one skilled in the art of peptide chemistry would expect the secondary structure and hydropathic nature of the polypeptide to be substantially unchanged. In general, the following amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Substitutions, deletions and/or amino acid additions may be made at any location(s) in the polypeptide, provided that the modification does not diminish the SPL activity of the variant. Thus, a variant may comprise only a portion of a native SPL sequence. In addition, or alternatively, variants may contain additional amino acid sequences (such as, for example, linkers, tags and/or ligands), preferably at the amino and/or carboxy termini. Such sequences may be used, for example, to facilitate purification, detection or cellular uptake of the polypeptide.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Saitou, N. Nei, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

The SPL activity of an SPL polypeptide or variant thereof may generally be assessed using an in vitro assay that detects the degradation of labeled substrate (i.e., sphingosine-1-phosphate, or a derivative thereof). Within such assays, pyridoxal 5'-phosphate is a requirement for SPL activity. In addition, the reaction generally proceeds optimally at pH 7.4-7.6 and requires chelators due to sensitivity toward heavy metal ions. The substrate should be a D-erythro isomer, but in derivatives of sphingosine-1-phosphate the type and chain length of sphingoid base may vary. In general, an assay as described by Van Veldhoven and Mannaerts, *J. Biol. Chem.* 266:12502-07, 1991 may be employed. Briefly, a solution (e.g., a cellular extract) containing the polypeptide may be incubated with 40 µM substrate at 37° C. for 1 hour in the presence of, for example, 50 mM sucrose, 100 mM K-phosphate buffer pH 7.4, 25 mM NaF, 0.1% (w/v) Triton X-100, 0.5 mM EDTA, 2 mM DTT, 0.25 mM pyridoxal phosphate. Reactions may then be terminated and analyzed by thin-layer chromatography to detect the formation of labeled fatty aldehydes and further metabolites. In general, a polypeptide has SPL activity if, within such an assay: (1) the presence of 2-50 µg polypeptide (or 0.1-10 mg/mL) results in a statistically significant increase in the level of substrate degradation, preferably a two-fold increase, relative to the level observed in the absence of polypeptide; and (2) the increase in the level of substrate degradation is pyridoxal 5'-phosphate dependent.

Within certain embodiments, an in vitro assay for SPL activity may be performed using cellular extracts prepared from cells that express the polypeptide of interest. Preferably, in the absence of a gene encoding an SPL polypeptide, such cells do not produce a significant amount of endogenous SPL (i.e., a cellular extract should not contain a detectable increase in the level of SPL, as compared to buffer alone without extract). It has been found, within the context of the present invention, that yeast cells containing deletion of the SPL gene (BST1) are suitable for use in evaluating the SPL activity of a polypeptide. bst1Δ cells can be generated from *S. cerevisiae* using standard techniques, such as PCR, as described herein. A polypeptide to be tested for SPL activity may then be expressed in bst1Δ cells, and the level of SPL activity in an extract containing the polypeptide may be compared to that of an extract prepared from cells that do not express the polypeptide. For such a test, a polypeptide is preferably expressed on a high-copy yeast vector (such as pYES2, which is available from Invitrogen) yielding more than 20 copies of the gene per cell. In general, a polypeptide has SPL activity if, when expressed using such a vector in a bst1Δ cell, a cellular extract results in a two-fold increase in substrate degradation over the level observed for an extract prepared from cells not expressing the polypeptide.

A further test for SPL activity may be based upon functional complementation in the bst1Δ strain. It has been found, within the context of the present invention, that bst1Δ cells are highly sensitive to D-erythro-sphingosine. In particular, concentrations as low as 10 µM sphingosine completely inhibit the growth of bst1Δ cells. Such a level of sphingosine has no effect on the growth of wildtype cells. A polypeptide having SPL activity as provided above significantly diminishes (i.e., by at least two fold) the sphingosine sensitivity when expressed on a high-copy yeast vector yielding more than 20 copies of the gene per cell.

In general, SPL polypeptides, and polynucleotides encoding such polypeptides, may be prepared using any of a variety of techniques that are well known in the art. For example, a DNA sequence encoding native SPL may be prepared by amplification from a suitable cDNA or genomic library using, for example, polymerase chain reaction (PCR) or hybridization techniques. Libraries may generally be prepared and screened using methods well known to those of ordinary skill in the art, such as those described in Sambrook et al., *Molecular Cloning: A Laboratory Manual*, Cold Spring Harbor Laboratories, Cold Spring Harbor, N.Y., 1989. cDNA libraries may be prepared from any of a variety of sources known to contain enzymes having SPL activity. SPL activity is ubiquitous with regard to species and mammalian tissues, with the exception of platelets, in which SPL activity is notably absent. In rat tissues, the highest levels of activity have been demonstrated in intestinal mucosa, liver and Harderian gland, with low activity in skeletal muscle and heart. Activity has also been demonstrated in a number of human (hepatoma cell line HB 8065, cervical carcinoma HeLa), mouse (hepatoma line BW1, mouse embryo 3T3-L1, Swiss 3T3 cells) and other cell lines, as well as in human cultured fibroblasts. Preferred cDNA libraries may prepared from human liver, intestine or brain tissues or cells. Other libraries that may be employed will be apparent to those of ordinary skill in the art. Primers for use in amplification may be readily designed based on the sequence of a native SPL polypeptide or polynucleotide, as provided herein.

Alternatively, an endogenous SPL gene may be identified using a screen for cDNAs that complement the BST1 deletion in yeast. A cDNA expression library may be generated using a regulatable yeast expression vector (e.g., pYES, which is available from Invitrogen, Inc.) and standard techniques. A yeast bst1Δ strain may then be transformed with the cDNA library, and endogenous cDNAs having the ability to functionally complement the yeast lyase defect (i.e., restore the ability to grow in the presence of D-erythro-sphingosine) may be isolated.

An endogenous SPL gene may also be identified based on cross-reactivity of the protein product with anti-SPL antibodies, which may be prepared as described herein. Such screens may generally be performed using standard techniques (see Huynh et al., "Construction and Screening cDNA Libraries in λgt11," in D. M. Glover, ed., *DNA Cloning: A Practical Approach*, 1:49-78, 1984 (IRL Press, Oxford)).

Polynucleotides encompassed by the present invention include DNA and RNA molecules that comprise an endogenous SPL gene sequence. Such polynucleotides include those that comprise a sequence recited in any one of SEQ ID NOs:1-16. Also encompassed are other polynucleotides that encode an SPL amino acid sequence encoded by such polynucleotides, as well as polynucleotides that encode variants of a native SPL sequence that retain SPL activity. Polynucleotides that are substantially homologous to a sequence complementary to an endogenous SPL gene are also within the scope of the present invention. "Substantial homology," as used herein refers to polynucleotides that are capable of hybridizing under moderately stringent conditions to a polynucleotide complementary to an SPL polynucleotide sequence provided herein, provided that the encoded SPL polypeptide variant retains SPL activity. Suitable moderately stringent conditions include prewashing in a solution of 5×SSC, 0.5% SDS, 1.0 mM EDTA (pH 8.0); hybridizing at 50-65° C., 5×SSC, overnight; followed by washing twice at 65° C. for 20 minutes with each of 2×, 0.5× and 0.2×SSC containing 0.1% SDS. Nucleotide sequences that, because of code degeneracy, encode a polypeptide encoded by any of the above sequences are also encompassed by the present invention.

Polypeptides of the present invention may be prepared by expression of recombinant DNA encoding the polypeptide in cultured host cells. Preferably, the host cells are bacteria, yeast, insect or mammalian cells, and more preferably the host cells are *S. cerevisiae* bst1Δ cells. The recombinant DNA may be cloned into any expression vector suitable for use within the host cell and transfected into the host cell using techniques well known to those of ordinary skill in the art. A suitable expression vector contains a promoter sequence that is active in the host cell. A tissue-specific or conditionally active promoter may also be used. Preferred promoters express the polypeptide at high levels.

Optionally, the construct may contain an enhancer, a transcription terminator, a poly(A) signal sequence, a bacterial or mammalian origin of replication and/or a selectable marker, all of which are well known in the art. Enhancer sequences may be included as part of the promoter region or separately. Transcription terminators are sequences that stop RNA polymerase-mediated transcription. The poly(A) signal may be contained within the termination sequence or incorporated separately. A selectable marker includes any gene that confers a phenotype on the host cell that allows transformed cells to be identified. Such markers may confer a growth advantage under specified conditions. Suitable selectable markers for bacteria are well known and include resistance genes for ampicillin, kanamycin and tetracycline. Suitable selectable markers for mammalian cells include hygromycin, neomycin, genes that complement a deficiency in the host (e.g., thymidine kinase and TK-cells) and others well known in the art. For yeast cells, one suitable selectable marker is URA3, which confers the ability to grow on medium without uracil.

DNA sequences expressed in this manner may encode a native SPL polypeptide (e.g., human), or may encode portions or other variants of native SPL polypeptide. DNA molecules encoding variants of a native SPL may generally be prepared using standard mutagenesis techniques, such as oligonucleotide-directed site-specific mutagenesis, and sections of the DNA sequence may be removed to permit preparation of truncated polypeptides.

To generate cells that express a polynucleotide encoding an SPL polypeptide, cells may be transfected, transformed or transduced using any of a variety of techniques known in the art. Any number of transfection, transformation, and transduction protocols known to those in the art may be used, for example those outlined in Current Protocols in Molecular Biology, John Wiley & Sons, New York. N.Y., or in numerous kits available commercially (e.g., Invitrogen Life Technologies, Carlsbad, Calif.). Such techniques may result in stable transformants or may be transient. One suitable transfection technique is electroporation, which may be performed on a variety of cell types, including mammalian cells, yeast cells and bacteria, using commercially available equipment. Optimal conditions for electroporation (including voltage, resistance and pulse length) are experimentally determined for the particular host cell type, and general guidelines for optimizing electroporation may be obtained from manufacturers. Other suitable methods for transfection will depend upon the type of cell used (e.g., the lithium acetate method for yeast), and will be apparent to those of ordinary skill in the art. Following transfection, cells may be maintained in conditions that promote expression of the polynucleotide within the cell. Appropriate conditions depend upon the expression system and cell type, and will be apparent to those skilled in the art.

SPL polypeptides may be expressed in transfected cells by culturing the cell under conditions promoting expression of the transfected polynucleotide. Appropriate conditions will depend on the specific host cell and expression vector employed, and will be readily apparent to those of ordinary skill in the art. For commercially available expression vectors, the polypeptide may generally be expressed according to the manufacturer's instructions. For certain purposes, expressed polypeptides of this invention may be isolated in substantially pure form. Preferably, the polypeptides are isolated to a purity of at least 80% by weight, more preferably to a purity of at least 95% by weight, and most preferably to a purity of at least 99% by weight. In general, such purification may be achieved using, for example, the standard techniques of ammonium sulfate fractionation, SDS-PAGE electrophoresis, and/or affinity chromatography.

The present invention further provides antibodies that bind to an SPL polypeptide. Antibodies may function as modulating agents (as discussed further below) to inhibit or block SPL activity in vivo. Alternatively, or in addition, antibodies may be used within screens for endogenous SPL polypeptides or modulating agents, for purification of SPL polypeptides, for assaying the level of SPL within a sample and/or for studies of SPL expression. Such antibodies may be polyclonal or monoclonal, and are generally specific for one or more SPL polypeptides and/or one or more variants thereof. Within certain preferred embodiments, antibodies are polyclonal.

Antibodies may be prepared by any of a variety of techniques known to those of ordinary skill in the art (see, e.g., Harlow and Lane, *Antibodies: A Laboratory Manual*, Cold Spring Harbor Laboratory, 1988). In one such technique, an immunogen comprising an SPL polypeptide or antigenic portion thereof is initially injected into a suitable animal (e.g., mice, rats, rabbits, sheep and goats), preferably according to a predetermined schedule incorporating one or more booster immunizations. The use of rabbits is preferred. To increase immunogenicity, an immunogen may be linked to, for example, glutaraldehyde or keyhole limpet hemocyanin (KLH). Following injection, the animals are bled periodically to obtain post-immune serum containing polyclonal anti-SPL antibodies. Polyclonal antibodies may then be purified from such antisera by, for example, affinity chromatography using an SPL polypeptide or antigenic portion thereof coupled to a suitable solid support. Such polyclonal antibodies may be used directly for screening purposes and for Western blots.

More specifically, an adult rabbit (e.g., NZW) may be immunized with 10 µg purified (e.g., using a nickel-column) SPL polypeptide emulsified in complete Freund's adjuvant (1:1 v/v) in a volume of 1 mL. Immunization may be achieved via injection in at least six different subcutaneous sites. For subsequent immunizations, 5 µg of an SPL polypeptide may be emulsified in complete Freund's adjuvant and injected in the same manner. Immunizations may continue until a suitable serum antibody titer is achieved (typically a total of about three immunizations). The rabbit may be bled immediately before immunization to obtain pre-immune serum, and then 7-10 days following each immunization.

For certain embodiments, monoclonal antibodies may be desired. Monoclonal antibodies may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

As noted above, the present invention provides agents that modulate, preferably inhibit, the expression (transcription or translation), stability and/or activity of an SPL polypeptide. To identify such a modulating agent, any of a variety of screens may be performed. Candidate modulating agents may be obtained using well known techniques from a variety of sources, such as plants, fungi or libraries of chemicals, small molecules or random peptides. Antibodies that bind to an SPL polypeptide, and anti-sense polynucleotides that hybridize to a polynucleotides that encodes an SPL, may be candidate modulating agents. Preferably, a modulating agent has a minimum of side effects and is non-toxic. For some applications, agents that can penetrate cells are preferred.

Screens for modulating agents that decrease SPL expression or stability may be readily performed using well known techniques that detect the level of SPL protein or mRNA. Suitable assays include RNAse protection assays, in situ hybridization, ELISAs, Northern blots and Western blots. Such assays may generally be performed using standard methods (see Sambrook et al., *Molecular Cloning: A Laboratory Manual*, Cold Spring Harbor Laboratories, Cold Spring Harbor, N.Y., 1989). For example, to detect mRNA encoding SPL, a nucleic acid probe complementary to all or a portion of the SPL gene sequence may be employed in a Northern blot analysis of mRNA prepared from suitable cells. Alternatively, realt-time PCR can also be used to detect levels of mRNA encoding SPL (see Gibson et al., *Genome Research* 6:995-1001, 1996; Heid et al., *Genome Research* 6:986-994, 1996). The first-strand cDNA to be used in the quantitative real-time PCR is synthesized from 20 µg of total RNA that is first treated with DNase I (e.g., Amplification Grade, Gibco BRL Life Technology, Gaithersburg, Md.), using Superscript Reverse Transcriptase (RT) (e.g., Gibco BRL Life Technology, Gaithersburg, Md.). Real-time PCR is performed, for example, with a GeneAmp™ 5700 sequence detection system (PE Biosystems, Foster City, Calif.). The 5700 system uses SYBR™ green, a fluorescent dye that only intercalates into double stranded DNA, and a set of gene-specific forward and reverse primers. The increase in fluorescence is monitored during the whole amplification process. The optimal concentration of primers is determined using a checkerboard. The PCR reaction is performed in 25 µl volumes that include 2.5 µl of SYBR green buffer, 2 µl of cDNA template and 2.5 µl each of the forward and reverse primers for the SPL gene, or other gene of interest. The cDNAs used for RT reactions are diluted approximately 1:10 for each gene of interest and 1:100 for the β-actin control. In order to quantitate the amount of specific cDNA (and hence initial mRNA) in the sample, a standard curve is generated for each run using the plasmid DNA containing the gene of interest. Standard curves are generated using the Ct values determined in the real-time PCR which are related to the initial cDNA concentration used in the assay. Standard dilution ranging from $20-2\times10^6$ copies of the SPL gene or other gene of interest are used for this purpose. In addition, a standard curve is generated for β-actin ranging from 200 fg-2000 fg. This enables standardization of the initial RNA content of a sample to the amount of β-actin for comparison purposes. The mean copy number for each sample tested is normalized to a constant amount of β-actin, allowing the evaluation of the observed expression levels of SPL or other gene of interest.

To detect SPL protein, a reagent that binds to the protein (typically an antibody, as described herein) may be employed within an ELISA or Western assay. Following binding, a reporter group suitable for direct or indirect detection of the reagent is employed (i.e., the reporter group may be covalently bound to the reagent or may be bound to a second molecule, such as Protein A, Protein G, immunoglobulin or lectin, which is itself capable of binding to the reagent). Suitable reporter groups include, but are not limited to, enzymes (e.g., horseradish peroxidase), substrates, cofactors, inhibitors, dyes, radionuclides, luminescent groups, fluorescent groups and biotin. Such reporter groups may be used to directly or indirectly detect binding of the reagent to a sample component using standard methods known to those of ordinary skill in the art.

To use such assays for identifying a modulating agent, the level of SPL protein or mRNA may be evaluated in cells treated with one or more candidate modulating agents. An increase or decrease in SPL levels may be measured by evaluating the level of SPL mRNA and/or protein in the presence and absence of candidate modulating agent. For example, an antisense modulating agent may be evaluated by assaying the effect on SPL levels. Suitable cells for use in such assays include the breast cancer cell lines MCF-7 (ATCC Accession Number HTB-22) and MDA-MB-231 (ATCC Accession Number HTB-26). A candidate modulator may be tested by transfecting the cells with a polynucleotide encoding the candidate and evaluating the effect of expression of the polynucleotide on SPL levels. Alternatively, the cells may be contacted with a candidate modulator, typically in an amount ranging from about 10 nM to about 10 mM. A candidate that results in a statistically significant change in the level of SPL mRNA and/or protein is a modulating agent.

Alternatively, or in addition, a candidate modulating agent may be tested for the ability to inhibit or increase SPL activity, using an in vitro assay as described herein (see Van Veldhoven and Mannaerts, *J. Biol. Chem.* 266:12502-07, 1991) that detects the degradation of labeled substrate (i.e., sphingosine-1-phosphate, or a derivative thereof). Briefly, a solution (e.g., a cellular extract) containing an SPL polypeptide (e.g., 10 nM to about 10 mM) may be incubated with a candidate modulating agent (typically 1 nM to 10 mM, preferably 10 nM to 1 mM) and a substrate (e.g., 40 μM) at 37° C. for 1 hour in the presence of, for example, 50 mM sucrose, 100 mM K-phosphate buffer pH 7.4, 25 mM NaF, 0.1% (w/v) Triton X-100, 0.5 mM EDTA, 2 mM DTT, 0.25 mM pyridoxal phosphate. Reactions may then be terminated and analyzed by thin-layer chromatography to detect the formation of labeled fatty aldehydes and further metabolites. A modulating agent (e.g., an antibody) that increases SPL activity results in a statistically significant increase in the degradation of sphingosine-1-phosphate, relative to the level of degradation in the absence of modulating agent. Such modulating agents may be used to increase SPL activity in a cell culture or a mammal, as described below.

A modulating agent may additionally comprise, or may be associated with, a targeting component that serves to direct the agent to a desired tissue or cell type. As used herein, a "targeting component" may be any substance (such as a compound or cell) that, when linked to a compound enhances the transport of the compound to a target tissue, thereby increasing the local concentration of the compound. Targeting components include antibodies or fragments thereof, receptors, ligands and other molecules that bind to cells of, or in the vicinity of, the target tissue. Known targeting components include hormones, antibodies against cell surface antigens, lectins, adhesion molecules, tumor cell surface binding ligands, steroids, cholesterol, lymphokines, fibrinolytic enzymes and other drugs and proteins that bind to a desired target site. In particular, anti-tumor antibodies and compounds that bind to an estrogen receptor may serve as targeting components. An antibody employed in the present invention may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage may be via any suitable covalent bond using standard techniques that are well known in the art. Such linkage is generally covalent and may be achieved by, for example, direct condensation or other reactions, or by way of bi- or multi-functional linkers.

For in vivo use, a modulating agent as described herein is generally incorporated into a pharmaceutical composition prior to administration. A pharmaceutical composition comprises one or more modulating agents in combination with a physiologically acceptable carrier. To prepare a pharmaceutical composition, an effective amount of one or more modulating agents is mixed with any pharmaceutical carrier(s) known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerine, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof. In addition, other pharmaceutically active ingredients (including other anti-cancer agents) and/or suitable excipients such as salts, buffers and stabilizers may, but need not, be present within the composition.

A modulating agent may be prepared with carriers that protect it against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

Administration may be achieved by a variety of different routes, including oral, parenteral, nasal, intravenous, intradermal, subcutaneous or topical. Preferred modes of administration depend upon the nature of the condition to be treated or prevented. An amount that, following administration, inhibits, prevents or delays the progression and/or metastasis of a cancer is considered effective. Preferably, the amount administered is sufficient to result in regression, as indicated by 50% mass or by scan dimensions. The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

As an alternative to direct administration of a modulating agent, a polynucleotide encoding a modulating agent may be administered. Such a polynucleotide may be present in a pharmaceutical composition within any of a variety of delivery systems known to those of ordinary skill in the art, including nucleic acid, bacterial and viral expression systems, and colloidal dispersion systems such as liposomes. Appropriate nucleic acid expression systems contain the necessary DNA sequences for expression in the patient (such as a suitable promoter and terminating signal, as described above). The DNA may also be "naked," as described, for example, in Ulmer et al., *Science* 259:1745-49, 1993.

Various viral vectors that can be used to introduce a nucleic acid sequence into the targeted patient's cells include, but are not limited to, vaccinia or other pox virus, herpes virus, retrovirus, or adenovirus. Techniques for incorporating DNA into such vectors are well known to those of ordinary skill in the art. Another delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preparation and use of liposomes is well known to those of ordinary skill in the art.

Within certain aspects of the present invention, one or more modulating agents may be used to modulate SPL expression and/or activity in vitro, in a cell or in a mammal. In vitro, an SPL polypeptide may be contacted with a modulating agent that increases or decreases SPL activity (e.g., certain antibodies). For use within a cell or a mammal, such modulation may be achieved by contacting a target cell with an effective amount of a modulating agent, as described herein. Administration to a mammal may generally be achieved as described above.

As noted above, increase of SPL expression and/or activity provides a method for inhibiting the growth (i.e., proliferation) of a cancer cell, either in culture or in a mammal afflicted with cancer. In vivo, such increase may also be used to inhibit cancer development, progression and/or metastasis. Accordingly, one or more modulating agents as provided herein may be administered as described above to a mammal in need of anti-cancer therapy. Patients that may benefit from administration of a modulating agent are those afflicted with cancer. Such patients may be identified based on standard criteria that are well known in the art. Within preferred embodiments, a patient is afflicted with breast cancer, as identified based on tissue biopsy and microscopic evaluation, using techniques well known in the art. In particular, patients whose tumor cells contain a tissue-specific deletion and/or alteration within an endogenous SPL gene may benefit from administration of a modulating agent, as provided herein.

Within other aspects, the present invention provides methods and kits for diagnosing cancer and/or identifying individuals with a risk for metastasis that is higher or lower than average. It has been found, within the context of the present invention, that certain human tumor cells contain an altered SPL gene. In particular, certain brain tumor cells contain a deletion of amino acid residues 354 to 433 of the human SPL sequence set forth in SEQ ID NO:8 (cDNA and amino acid sequence of the SPL containing the deletion are set forth in SEQ ID NOs:9 and 10, respectively). Specific alterations present in other tumor cells, such as breast tumor cells, may be readily identified using standard techniques, such as PCR. Alterations that may be associated with a particular tumor include amino acid deletions, insertions, substitutions and combinations thereof. Methods in which the presence or absence of such an alteration is determined may generally be used to detect cancer and to evaluate the prognosis for a patient known to be afflicted with cancer.

To detect an altered SPL gene, any of a variety of well-known techniques may be used including, but not limited to, PCR and hybridization techniques. Any sample that may contain cancerous cells may be assayed. In general, suitable samples are tumor biopsies. Within a preferred embodiment, a sample is a breast tumor biopsy.

Kits for diagnosing or evaluating the prognosis of a cancer generally comprise reagents for use in the particular assay to be employed. In general, a kit of the present invention comprises one or more containers enclosing elements, such as primers, probes, reagents or buffers, to be used in an assay.

For example, a kit may contain one or more polynucleotide primers or probes comprising at least 15 nucleotides complementary to a polynucleotide encoding SPL. In certain embodiments, the primers or probes comprise at least 10, 25, 30, 35, 40, 45, 50, 55, 60, 65, 70, 75, 80, 85, 90, 95 or 100 nucleotides, and preferably at least 150 or 200 nucleotides, complementary to an SPL mRNA or to a polynucleotide encoding SPL. Such probe(s) may be used to detect an altered SPL gene by hybridization. For example, a kit may contain one probe that hybridizes to a region of an SPL gene that is not generally altered in tumors (a control) and a second probe that hybridizes to a region commonly deleted in breast cancer. A sample that contains mRNA that hybridizes to the first probe, and not to the second (using standard techniques) contains an altered SPL gene. Suitable control probes include probes that hybridize to a portion of the SPL gene outside of the commonly deleted region encoding amino acid resides 354 to 433; suitable probes for an altered region include probes that hybridize to a portion of the SPL gene that encodes amino acid residues 354 to 433. Alternatively, a kit may comprise one or more primers for PCR analyses, which may be readily designed based upon the sequences provided herein by those of ordinary skill in the art. Optionally, a kit may further comprise one or more solutions, compounds or detection reagents for use within an assay as described above.

In a related aspect of the present invention, kits for detecting SPL are provided. Such kits may be designed for detecting the level of SPL or nucleic acid encoding SPL within a sample, or may detect the level of SPL activity as described herein. A kit for detecting the level of SPL, or nucleic acid encoding SPL, typically contains a reagent that binds to the SPL protein, DNA or RNA. To detect nucleic acid encoding SPL, the reagent may be a nucleic acid probe or a PCR primer. To detect SPL protein, the reagent is typically an antibody. The kit may also contain a reporter group suitable for direct or indirect detection of the reagent as described above.

Within further aspects, the present invention provides transgenic mammals in which SPL activity is reduced, compared to a wild-type animal. Such animals may contain an alteration, insertion or deletion in an endogenous SPL gene, or may contain DNA encoding a modulating agent that modulates expression or activity of an SPL gene. In certain aspects, such animals may contain DNA encoding a modulating agent that increases expression or activity of an SPL gene. Transgenic animals may be generated using techniques that are known to those of ordinary skill in the art. For example, a transgenic animal containing an insertion or deletion in the coding region for the SPL gene may be generated from embryonic stem cells, using standard techniques. Such stem cells may be generated by first identifying the full genomic sequence of the gene encoding the SPL, and then creating an insertion or deletion in the coding region in embryonic stem cells. Alternatively, appropriate genetically altered embryonic stem cells may be identified from a bank. Using the altered stem cells, hybrid animals may be generated with one normal SPL gene and one marked, abnormal gene. These hybrids may be mated, and homozygous progeny identified.

Transgenic animals may be used for a variety of purposes, which will be apparent to those of ordinary skill in the art. For example, such animals may be used to prepare cell lines from different tissues, using well known techniques. Such cell lines may be used, for example, to evaluate the effect of the alteration, and to test various candidate modulators.

The invention further provides *Drosophila melanogaster* animal models that exhibit a flightless phenotype, where the phenotype results from the disruption of an endogenous SPL gene as described in greater detail below. By flightless phenotype is meant that the subject non-mammalian animal models spontaneously develop a reduced number of muscle fibers comprising the dorsal longitudinal muscles (DLM) and have compensatory hypertrophy in the remaining fibers. In certain aspects, the non-mammalian animal model of the present invention may also demonstrate abnormal developmental patterning of thoracic muscles of the T2 segment. In a preferred embodiment, the above phenotypes result in an inability to fly. The subject non-mammalian animal models, within a preferred embodiment, demonstrate altered activity of the endogenous SPL. In a particularly illustrative embodiment, said D. melanogaster animal models have decreased activity of endogenous SPL.

Within further aspects, the present invention provides mutant strains of Drosophila melanogaster. In a preferred embodiment, the strain contains a mutation in the SPL gene. In a further embodiment of the present invention the D. melanogaster strain are heterozygous for a P-element transposon which sits in the coding region of the gene encoding the SPL protein set forth in SEQ ID NO:16. In a preferred embodiment, the flies are homozygous insertional mutants in the coding region of the gene encoding the SPL protein set forth in SEQ ID NO:16. In yet a further embodiment of the present invention, the homozygous mutant strain of fly has a flightless phenotype. In certain embodiments, the mutant flies have a reduced number of muscle fibers comprising the dorsal longitudinal muscles and have compensatory hypertrophy in the remaining fibers. In certain aspects, the mutant flies of the present invention may also demonstrate abnormal developmental patterning of thoracic muscles of the T2 segment.

Flies heterozygous for a P-element transposon which sits in the coding region of the SPL gene or genes and disrupts production of SPL proteins may be obtained from the Drosophila Genome Project. Homozygous insertional mutants can be made, using techniques known in the art, by genetically crossing and evaluating progeny for the presence of homozygous insertional mutants (based on presence of rosy eye color, encoded by a recessive marker carried on the P-element). Expression of the SPL gene can be evaluated using any number of assays known to the skilled artisan, for example, by Northern blot analysis. To determine the SPL function of each genotype, +/+, +/− and −/− flies may be homogenized using standard techniques and whole extracts can be assayed for SPL activity using assays as described herein. The transposon can be mobilized by crossing SPL mutant flies with flies carrying an actively transcribed transposase gene, which should cause the P-element to be excised in the chromosomes of both somatic cells and in the germline. Germline transposon loss is heritable and can be identified in progeny by virtue of eye color. Progeny which lost both the transposase gene and the P-element can then be isolated and the restored SPL allele can be homozygosed.

Mutations in Drosophila melanogaster as described herein which permanently block expression of a functional protein can be created in several ways, such as with P-element transposon insertions or chemical or radiation induced mutagenesis. Exemplary strains of mutant flies are available through the Drosophila Genome Project, at the University of California at Berkeley (Adams, M. et al. 2000. The genome sequence of Drosophila melanogaster. Science. 287:2185-2195.). Alternatively, insertional mutant of interest may be obtained by using local hop strategies essentially as described in Tower, J. et al (Tower, J., et al. 1993. Preferential transposition of Drosophila P elements to nearby chromosomal sites. Genetics. 133:347-359.), hereby incorporated by reference in its entirety. Transposons can be mobilized by crossing in a transposase gene, followed by crossing the transposase back out (reintroducing genetic stability). Mutant flies can be identified using techniques know to those of skill in the art. For example, mutant flies can be identified by probing Southern blots prepared from extracts from flies generated in the screen using the target gene as probe. Subsequently, crosses can be performed to introduce a mutant allele of interest, (e.g. SPL) and generate homozygosity at both mutant alleles (e.g. SPL and new transposon integration sites). Mutants can be screened for a phenotype of interest, for example the ability to restore flight to an SPL mutant when the mutated allele is homozygous (predicting a recessive phenotype).

In one aspect of the present invention, fly genetic manipulation may entail mating or "crossing" of flies and selection for or against progeny expressing various phenotypic markers. Exemplary techniques for fly genetic manipulation of the present invention are know in the art and are described, for example in, Ashburner, M., and J. Roote. 2000. Laboratory culture of Drosophila. In Drosophila Protocols. W. Sullivan, M. Ashburner, and R. Hawley, editors. Cold Spring Harbor Laboratory Press, Cold Spring Harbor, N.Y. 585-600. Phenotypic markers may be used to identify the inheritance of chromosomes, engineered transposable elements, or transposase genes used to facilitate their mobilization. Marker mutations affecting eye color, bristle shape, wing morphology and cuticle pigmentation, for example, may be employed in the crosses for the mutant flies of the present invention. Within one aspect of the present invention, it may be desirable to select the individuals which contain a collection of markers indicating the desired genotype. In another aspect of the present invention, balancer chromosomes may be used to create the ability to identify recessive mutations present in the heterozygous state. Balancer chromosomes may be employed to prevent homologous recombination during meiotic prophase in females. The presence of both dominant and recessive lethal markers allows one to determine the presence or absence of the balancer chromosomes and simultaneously to follow the homologous chromosomes, which may themselves not contain a dominant marker. One particularly illustrative cross of the present invention is to eliminate the P-element insertion in the Drosophila SPL gene and establish phenotypic reversion, as described herein in the Examples.

Selective markers to allow for selection of mutant flies is provided for in the present invention. Exemplary selective markers of the present invention may comprise a wild type rosy (ry$^+$) allele carried on the transposon to allow for selection for or against the stable transposon. Introduction of an active transposase is selected for by presence of the dominant marker, Stubble (short bristle phenotype) in the first cross, and is selected against to identify progeny which have lost the transposase, restoring genetic stability in the second cross. Other illustrative markers include Curly 0 (CyO) which is lethal when present in two copies, allowing selection for heterozygotes containing the CyO balancer and another allele of interest originally containing the transposon (e.g., SPL). By selecting against rosy eye color, progeny in which the transposon has been excised from the locus of interest, e.g., SPL, can be identified. Expansion of this "reverted" allele in the population can be achieved in the third cross, and the desired allele can be homozygosed in the final cross, to determine whether restoration of the intact allele of interest, for example SPL, is associated with a desired phenotype of interest, such as restoration of flight.

In another aspect of the present invention, transgenic flies can be created using P-elements to overexpress or misexpress proteins of interest, such as SPL. In one embodiment of the invention, GAL4-mediated ectopic gene expression is employed, essentially as described (van Roessel, P., and A. Brand. 2000. GAL4-mediated ectopic gene expression in *Drosophila*. In *Drosophila* Protocols. W. Sullivan, M. Ashburner, and R. Hawley, editors. Cold Spring Harbor Laboratory Press, Cold Spring Harbor, N.Y. 439-448). The GAL4 protein is a yeast transcription factor capable of activating transcription of *Drosophila* genes which have been engineered to contain upstream sequences recognized by the GAL4 protein. Various mutants can be created with a gene of interest expressed in specific tissue distributions, a construct containing the gene of interest (reporter) under regulation of a GAL4 containing promoter is introduced into embryos, and a genetic marker allows identification of progeny containing this construct. Illustrative GAL4 containing promoters include, but are not limited to, pUAS. The use of embryos of a strain containing an active P-transposase increases the efficiency of transgene integration, although many of the embryos die. These progeny can then be crossed to various available lines containing GAL4 transgenes (driver) expressed under control of tissue-specific promoters. In one aspect of the present invention, GAL4 driver constructs which allow expression during embryogenesis are used.

The following Examples are offered by way of illustration and not by way of limitation.

EXAMPLES

Example 1

Isolation and Characterization of SPL cDNA from Yeast

This Example illustrates the preparation of an *S. cerevisiae* cDNA molecule encoding an endogenous SPL polypeptide.

Wild-type yeast cells (SGP3 (Garrett and Broach, *Genes and Dev.* 3:1336-1348, 1989); leu2-3,112 trp1 ura3-52 his3 ade8 ras1::HIS3) were transformed with a yeast genomic library carried on the pRS202 high-copy shuttle vector (Sikorski and Heiter, *Genetics* 122:19-27, 1989) containing a selectable nutritional marker (URA3). pRS202 is a modified version of the pRS306 vector, into which a 2 micron plasmid piece was inserted. Inserts from this library are approximately 6-8 kb in length. Wild type yeast were transformed with the high copy library as described by Ito et al., *J. Bact.* 153:163-68, 1983, selected for uracil prototrophy (i.e., the ability to grow on medium lacking uracil), and transformants were pooled and replated at a concentration of $10^6$ cells per plate onto 1 mM D-erythro-sphingosine plates.

Six transformants which grew large colonies on 1 mM D-erythro-sphingosine plates were grown in selective medium, and control SGP3 colonies were grown in minimal medium, at 30° C. until saturated. Absorbance at 660 nm was used to correct for small variations in cell concentration between cultures. Serial dilutions were performed, and cells were template-inoculated onto 1 mM D-erythro-sphingosine plates and incubated at 30° C. for 48 hours.

The most highly represented insert, 13-1, was subcloned and sequenced, and named BST1 (bestower of sphingosine tolerance; GenBank accession number U51031; *Saccharomyces cerevisiae* genome database accession number YDR294C). The BST1 nucleotide sequence encodes a previously unknown predicted protein of 65,523 kilodaltons and 589 amino acids in length. This sequence is 23% identical to gadA and gadB, two nearly identical *E. coli* genes encoding glutamate decarboxylase (GAD), a pyridoxal-5'-phosphate-dependent enzyme which catalyzes synthesis of the neurotransmitter γ-amino butyric acid. BST1 has been localized to *S. cerevisiae* chromosome 4. The DNA sequence of BST1 is provided in SEQ ID NO:1, which encodes the amino acid sequence set forth in SEQ ID NO:2.

To explore the function of BST1, a deletion strain was created through homologous recombination using a NEO selectable marker (Wach et al., *Yeast* 10:1793-1808, 1994). Genomic BST1 was replaced with kanMX (Wach et al., *Yeast* 10:1793-1808, 1994), which confers resistance to G418. Disruption was confirmed using PCR amplification of genomic DNA from G418 resistant clones, using primers to genomic sequence just 5' and 3' to the region replaced by the disruption. Deletion of BST1 and all subsequent biological studies were performed in both SGP3 and in JK93d (Hietman et al., *Proc. Natl. Acad. Sci. USA* 88:1948-52, 1991); ura3-52 leu2-3,112 his4 trp1 rme1). Heterozygous diploids were sporulated, and spores segregated 2:2 for G418 resistance. Both G418 resistant and sensitive progeny were viable, indicating that BST1 is not an essential gene.

Analysis of GAD activity in cytosolic extracts from wild type, BST1 overexpression and bst1Δ strains indicated that BST1 does not encode the *S. cerevisiae* homologue of GAD. However, deletion of BST1 was associated with severe sensitivity to D-erythro-sphingosine. Concentrations as low as 10 µM sphingosine completely inhibited growth of bst1Δ strains but had no effect on the viability of wild type cells. In comparison to the control strain, the bst1Δ strain also demonstrated greater sensitivity to 100 µM phytosphingosine, the long chain base endogenous to *S. cerevisiae*. No difference between the growth of wild type and BST1 overexpression strains on phytosphingosine, which is only minimally toxic to wild type cells at this concentration, was observed.

To determine whether differences in sphingosine uptake or metabolism were responsible for these sensitivity differences, BST1 wild type, overexpression and bst1Δ strains were exposed to [C3-$^3$H]labeled sphingosine (American Radiolabeled Chemical, Inc., St. Louis, Mo.), washed in sterile water and subjected to Bligh-Dyer extractions (Bligh and Dyer, *Can. J. Buichem. Physiol.* 37:911-17, 1959). There were no major differences in sphingosine recovery among the three strains. However, the aqueous phase from the bst1Δ strain contained a ten-fold increase in radioactivity over that of control and BST1 overexpression strains. Thin layer chromatography (TLC) analysis of the lipid fractions in butanol:acetic acid:water (3:1:1) revealed a sphingosine band which appeared equivalent in each strain.

Radioactive sphingosine-1-phosphate (S-1-P) was also observed in the extracts from the bst1Δ strain, but not in the wild type or BST1 overexpression strains. This compound accumulated rapidly, reaching a plateau by 60 minutes. Three separate TLC conditions were used to confirm the presence of S-1-P. These conditions, along with the resulting RF values, are shown below:

| | |
|---|---|
| butanol:water:acetic acid (3:1:1) | .47 |
| chloroform:methanol:water (60:35:8) | .22 |
| chloroform:methanol:water:acetic acid (30:30:2:5) | .33 |

Hyperaccumulation of S-1-P and hypersensitivity to D-erythro-sphingosine suggest a failure to metabolize S-1-P, indicating that BST1 is a yeast SPL. To confirm this identification, lyase activity in BST1 wild type, overexpression and deletion strains were evaluated as described by Veldhoven and Mannaerts, *J. Biol. Chem.* 266:12502-07, 1991, using unlabeled D-erythro-dihydrosphingosine-1-phosphate (Biomol, Plymouth Meeting, Pa.) and D-erythro-dihydrosphingosine [4,5-³H]1-phosphate (American Radiolabeled Chemicals, Inc., St. Louis, Mo.). Specific activity was 100 mCi/mmol. SPL activity was found to correlate with BST1 expression, confirming BST1 to be the yeast homologue of sphingosine-1-phosphate lyase.

These results indication that BST1 is a yeast SPL, and that SPL catalyzes a rate-limiting step in sphingolipid catabolism. Regulation of SPL activity may therefore result in regulation of intracellular S-1-P levels.

Example 2

Isolation and Characterization of SPL cDNA from *C. elegans* and Mouse

This Example illustrates the identification of endogenous SPL cDNAs from *C. elegans* and *Mus musculus*.

Comparison of the yeast BST1 sequence to sequences within the GenBank database identified a full length gene from *C. elegans* that was identified during the systematic sequencing of the *C. elegans* genome. This cDNA sequence is set forth in SEQ ID NO:3 and was found to encode SPL, the sequence set forth in SEQ ID NO:4. This and other DNA homology searches described herein were performed via the National Center for Biotechnology Information website using BLAST search program.

Using both *S. cerevisiae* and *C. elegans* SPL sequences to search the EST database, an expressed sequence tag from early embryonic cells of the mouse (day 8 embryo, strain C57BL/6J) was identified. The cDNA clone containing this putative mouse SPL was purchased from Genome Systems, Inc (St. Louis, Mo.). Completion of the full length cDNA sequence revealed an 1707 bp open reading frame. This mouse sequence showed significant homology to BST1 and to other pyridoxal phosphate-binding enzymes such as glutamate decarboxylase, with greatest conservation surrounding the predicted pyridoxal phosphate-binding lysine. Since the two genes encoding mouse glutamate decarboxylase have been identified previously, and the identified sequence was unique and had no known function, it was a likely candidate mouse SPL gene.

To confirm the SPL activity of the mouse gene, a two step process was undertaken. First, the sequence was cloned into the high-copy yeast expression vector, pYES2 (Invitrogen, Inc., Carlsbad, Calif.), in which the gene of interest is placed under control of the yeast GAL promoter and is, therefore, transcriptionally activated by galactose and repressed by glucose. pYES2 also contains the URA3 gene (which provides transformants the ability to grow in media without uracil) and an ampicillin resistance marker and origin of replication functional in *E. coli*.

The expression vector containing the full-length mouse SPL gene was then introduced into the yeast bst1Δ strain which, as noted above, is extremely sensitive to D-erythro-sphingosine, as a result of metabolism of sphingosine to S-1-P. S-1-P cannot be further degraded in the absence of SPL activity and overaccumulates, causing growth inhibition. Transformation was performed using the lithium acetate method (Ito et al., *J. Bact.* 153:163-68, 1983). Transformants were grown on medium containing 20 g/L galactose and selected for uracil prototrophy.

Transformants were then evaluated for sphingosine resistance. Strains of interest were grown to saturation in liquid culture for 2-3 days. They were then resuspended in minimal medium, placed in the first row of a 96-well plate and diluted serially from 1:2 to 1:4000 across the plate. The cultures were then template inoculated onto a control plate (YPD) and a plate containing minimal synthetic media supplemented with 50 µM D-erythro-sphingosine (Sigma Chemical Co., St. Louis, Mo.) and 0.0015% NP40 (Sigma Chemical Co.). At this concentration of NP40, no effects on cell viability were observed. Plates were incubated at 30° C. for two days and assessed visually for differences in growth. Transformants containing the mouse SPL gene were resistant to sphingosine present in galactose-containing plates. A strain transformed with vector alone remained sensitive to sphingosine. Therefore, the mouse SPL gene was capable of reversing the sphingosine-sensitive phenotype of a yeast bst1Δ strain.

In order to determine whether the mouse SPL gene was able to restore biochemical SPL activity to the bst1Δ strain, the untransformed bst1Δ strain, and the bst1Δ strain transformed with pYES2 containing either BST1 or the putative mouse SPL gene were grown to exponential phase ($A_{600}$=1.0) in either minimal (JS16) or uracil medium containing galactose as a carbon source. Whole cell extracts were prepared from each strain as described above, adjusted for protein concentration, and evaluated for sphingosine phosphate lyase activity as described above, using ³H-dihydrosphingosine-1-phosphate (American Radiolabeled Chemicals, Inc., St. Louis, Mo.). Qualitative analysis of product was performed by autoradiography. Quantitative measurement was performed by scraping TLC plates and determining radioactivity present using a standard scintillation counter.

The results of the sphingosine phosphate lyase assays shown that expression of both the yeast and mouse sequences restored SPL activity to the bst1Δ strain, whereas vector alone had no effect, confirming the identity of the mouse sequence as SPL.

To determine whether the expression of the mouse SPL transcript coincided with previously reported tissue-specific SPL activity in the mouse, total RNA was obtained from a variety of mouse tissues and probed with the complete mouse SPL cDNA sequence. Northern analysis was performed as described by Thomas, *Proc. Natl. Acad. Sci. USA* 77:5201, 1980, using a full length mouse SPL cDNA probe labeled by random labeling technique (Cobianchi and Wilson, *Meth. Enzymol.* 152:94-110, 1987). This analysis revealed a pattern of expression consistent with the known SPL activity in various mouse tissues, providing further confirmation that this sequence encodes mouse SPL.

Example 3

Isolation and Characterization of Human SPL cDNA

This Example illustrates the identification of an endogenous human cDNA.

An EST database was searched using the mouse SPL sequence described herein. Two distinct EST sequences having strong homology to the mouse sequence were identified from human sources. One of these sequences corresponded to the C-terminus, and the other corresponded to the N-terminus. Primers were designed based on these sequences, and a DNA fragment was amplified by PCR from a human expression library made from human glioblastoma multiforme tissue RNA. The fragment was sequenced and was shown to contain a deletion, so the primers were used to amplify the gene from human fibroblast RNA. This gene has the sequence provided in SEQ ID NO:7 and encodes the polypeptide sequence provided in SEQ ID NO:8. The cDNA and amino acid sequences of the SPL containing the deletion are set forth in SEQ ID NOs:9 and 10, respectively.

Example 4

Isolation and Characterization of C. Elegans SPL cDNA

This Example illustrates the identification of a cDNA molecule encoding a primary C. elegans sphingosine phosphate lyase.

The human SPL cDNA sequence was used to screen the ACEdb C. elegans genome database. A potential C. elegans open reading frame of unknown function present on YAC Y66H1B showed substantial (40%) homology to yeast, human and mouse SPL cDNA sequences. To clone this sequence, a coupled reverse transcriptase/polymerase chain reaction was performed using the Access RT-PCR system (see below). Template was C. elegans total RNA, and primers were:

```
5'-GAGGAATTCATGGATTCGGTTAAGCACACAACCG-3'

5'-AGCCTCGAGTTAATTAGAAGTTGAAGGTGGAGC-3'
```

This resulted in a DNA fragment cSPL2, which was ligated into the yeast expression vector pYES2, obtained from Invitrogen. Inc. (Carlsbad, Calif.). Genes expressed using this system are regulated under the control of the GAL promoter, which allows expression in the presence of galactose and not in the presence of glucose. The nucleotide sequence of cSPL2 is set forth in SEQ ID NO:12, with the encoded amino acid sequence set forth in SEQ ID NO:11 cSPL2 was further analyzed for its ability to complement the sphingosine sensitive phenotype of a yeast dpl1 mutant, the previously described yeast strain JS16 which contains a large deletion in DPL1, the S. cerevisiae sphingosine phosphate lyase gene (Zhou and Saba, *Biochem Biophys Res Commun* 242:502-507, 1998). Transformation of JS16 with pYES2 or the C. elegans SPL-pYES2 construct was performed by the lithium acetate method (Ito et al., *J. Bact.* 153:163-168, 1983). Transformants were selected for uracil prototrophy and evaluated for sphingosine resistance using the dilutional assay described by Zhou and Saba, *Biochem Biophys Res Commun* 242:502-507, 1998. Cells were grown in minimal or uracil⁻ media containing either 20 g glucose or galactose per liter, as indicated. D-erythro-sphingosine and NP40 were obtained from Sigma Chemical Company (St. Louis, Mo.).

The results demonstrate that cSPL2 convincingly complemented the yeast mutant, restoring enzyme activity. In each plate, yeast were grown to saturation in overnight liquid cultures, spun down, resuspended in 200 microliters of water and dispensed into the first (left-most) well of each horizontal row. Yeast were then further diluted into sterile water, so the second well was 1:2, third well was 1:4, fourth well was 1:40, fifth was 1:400 and sixth was 1:4000 dilution from the original on the left. The toxicity of sphingosine is cell number dependent, because it disperses itself in cell membranes. Therefore, the concentration of sphingosine in the plate is not the only thing affecting toxicity, and these dilutional assays show differences in tolerance/sensitivity. So, a strain which can grow in the sixth row is about 4,000 times more resistant to sphingosine than one which can grow only in the first row.

The mutant yeast strain containing cSPL2 also demonstrated substantial SPL activity. The sphingosine phosphate lyase assay used whole cell extracts of yeast containing either pYES2 vector alone or (cSPL2) C. elegans SPL-pYES2. Extracts were prepared as described by Saba et al., *J Biol Chem* 272:26087, 1997. SPL activity was determined essentially as described, using $^3$H-dihydrosphingosine-1-phosphate substrate (see Zhou and Saba, *Biochem Biophys Res Commun* 242:502-507, 1998). Substrate for SPL assay ($^3$H-dihydrosphingosine-1-phosphate) was obtained from American Radiolabeled Chemicals, Inc. (St. Louis, Mo.). Access RT-PCR system was obtained from Promega Corp. (Madison, Wis.).

Enzyme activity in (cSPL2) C. elegans SPL-pYES2 was appreciably greater than that of the vector control. These results indicate that cSPL2 encodes the primary C. elegans SPL.

Example 5

Developmental Defects Induced by RNA Interference in C. elegans

In order to determine the effect of blocking cSPL2 expression on the development of C. elegans, RNA interference studies were undertaken. The cSPL2 cDNA was cloned into pBluescript such that the insert was flanked by the T3 and T7 promoter regions. RNA complementary to each strand was synthesized from these promoters using an in vitro transcription kit (Promega, Madison, Wis.). The two strands were annealed to make double stranded RNA (dsRNA) and injected into the distal gonads of 12 wild-type (N2 Bristol) young adult C. elegans hermaphrodites. As controls, uninjected hermaphrodites as well as hermaphrodites injected with a dsRNA that does not produce a visible phenotype were handled in parallel. Eight hours after injection, each hermaphrodite was transferred to a fresh culture plate and 12 hour cohorts of F1 progeny were established. Progeny were observed daily with a dissecting microscope until most animals reached adulthood and the culture plates became too crowded with F2 progeny. Compared to control F1s, animals inheriting cSPL-2 dsRNA developed slowly, moved sluggishly, were thin and pale, and did not pump food actively. These animals reach adulthood approximately 24 hours later than controls. Adult hermaphrodites that inherited cSPL-2 dsRNA were markedly different from controls especially in the gonad and uterus. Control animals had abundant nuclei in the distal gonad and a row of developing oocytes in the proximal gonad. Affected hermaphrodites had poorly developed distal gonads with fewer nuclei. Control adults had embryos of progressive stages of development in the uterus, whereas the number of developing oocytes in the proximal gonad of affected hermaphrodites was reduced. The embryos in the uterus of affected progeny were also abnormal. Those near the vulva were at late developmental stages indicating a defect in egg laying. There was not a uniform progression of developmental stages in adjacent embryos suggesting a defect in ovulation or development, and some of the embryos showed abnormal patterns of cell division. In summary, inhibition of C. elegans SPL expression through the use of RNA interference leads to poor feeding, developmental abnormalities and impaired fertility in the progeny. These results suggest that SPL is an essential gene in C. elegans.

Example 6

Isolation and Characterization of SPL cDNA from Drosophila melanogaster

In order to seek out the Drosophila melanogaster SPL cDNA and genomic sequence, the D. melanogaster genomic database was searched for sequences which demonstrated significant homology to human SPL cDNA. This led to identification of two full-length cDNA clones (LP04413 and GH3783) which were confirmed by sequence and restriction analysis. The two clones are predicted based on alternative 5' exon usage and may be expressed in different subcellular locations. The predicted *Drosophila melanogaster* SPL is located on the right arm of chromosome II, position 53F8-12. The cDNA sequence for *Drosophila melanogaster* SPL is set forth in SEQ ID NO:15 and encodes the SPL protein set forth in SEQ ID NO:16. The *Drosophila* SPL predicted protein sequence set forth in SEQ ID NO:16 is 49%, 49% and 43% identical to human, mouse and yeast SPL protein sequences, respectively.

In order to evaluate whether these clones contained a functional SPL gene, they were recloned into the yeast expression vector, pYES2, and this construct was transformed into a dpl1Δ strain. Expression of clones containing the potential *Drosophila melanogaster* SPL fully complement the dpl1Δ strain's sensitivity to 50 μM D-erythro-sphingosine. Further, whole cell extracts of dpl1 strains containing either pYES2-LP04413 or pYES2-GH3783 demonstrate restoration of SPL enzyme activity to wild type levels or greater, although not as high as a DPL1 overexpressing strain (DPL OE).

Example 7

Generation and Characterization of SPL Transposon Mutant *D. melanogaster*

Flies heterozygous for a P-element transposon which sits in the coding region of both of the above transcripts described in Example 6 and presumably disrupts both SPL proteins were obtained from the *Drosophila* Genome Project. These flies were genetically crossed using techniques well known to ordinarily skilled artisans, and progeny were evaluated for the presence of homozygous insertional mutants (based on presence of rosy eye color, encoded by a recessive marker carried on the P-element). Northern blot analysis from wild type and SPL insertional mutant flies indicated that no SPL gene expression occurred in the latter.

To determine the SPL function of each genotype, +/+, +/- and -/- flies were homogenized and whole extracts assayed for SPL activity. It was observed that SPL genotype corresponded with SPL activity with +/+>+/->-/-. Initial evaluation of homozygous mutants indicated that adult SPL mutants were flightless, suggesting a potential defect in either muscle development or energetics of the adult fly. Flight analysis was carried out essentially as described (Vigoreaux, J., J. Saide, K. Valgeirdottir, and M. Pardue. 1993. Flightin, a novel myofibrillar protein of *Drosophila* stretch-activated muscles. *J Cell Biol*. 121:587-598) by determining the percentage of flies that were flightless or exhibited downward, upward, or lateral flight capabilities in control Canton-S flies as compared to mutant flies.

The transposon was mobilized by crossing SPL mutant flies with flies carrying an actively transcribed transposase gene, which caused the P-element to be excised in the chromosomes of both somatic cells and in the germline. Germline transposon loss is heritable and was identified in progeny by virtue of eye color. Progeny which lost both the transposase gene and the P-element were then isolated and the restored SPL allele was homozygosed. Progeny which had lost the P-element at the SPL locus demonstrated restoration of flight, indicating that the phenotype correlated with the P-element insertional mutation. To determine the etiology of the flightlessness of -/- flies, flies were sectioned through the thoracic region and indirect flight muscles were evaluated by both light and electron microscopy. These studies revealed a reduced number of muscle fibers comprising the dorsal longitudinal muscles with evidence of what appears to be compensatory hypertrophy in the fibers which remained. Electron microscopy revealed no ultrastructural defects in the myocytes which remained.

In order to determine whether the loss of SPL expression was due to excess accumulation of S-1-P in the developing adult fly, we salvaged the developing flight muscles of homozygous SPL mutant progeny by adding D,L-threo-dihydrosphingosine, an inhibitor of mammalian sphingosine kinase, to the growth media. A significant proportion of homozygous SPL mutant progeny demonstrated restoration of flight when grown on media supplemented with D,L-threo-dihydrosphingosine.

Northern analysis was performed to investigate SPL expression throughout development. These studies indicated that SPL expression begins at 8-12 hours of embryonic development and remains detectable throughout larval stages and pupation.

Therefore, the *Drosophila melanogaster* model described herein can be used to identify pharmacologic suppressors of SPL mutant flies' inability to fly. Drugs which alter SPL activity or expression may be effective treatment for at least some kinds of cancer. Therefore, the fact that a fruitfly SPL null mutant containing a P-element insertion within the SPL coding region is flightless provides an excellent model in which to screen and identify compounds that modulate SPL activity. Thus, other chemicals created through rational drug design approaches can be screened using this method. The *Drosophila melanogaster* model described herein can thus be used to screen an array of rationally designed chemicals with homology to sphingolipids for their ability to restore flight to SPL mutant progeny. Candidate drugs identified using this method can then be further evaluated in an in vitro yeast screen.

Example 8

Further Characterization of Developmental Expression Patterns of SPL in SPL Transposon Mutant *D. melanogaster*

Northern analysis is carried out and extended to include adult samples, and blots are reprobed with SPL specific probes using the following approaches. Once genes are confirmed to encode the predicted enzyme, DNA probes or riboprobes for SPL and S-1-P phosphatase are labeled either radioactively or with digoxygenin. For Northern analysis, full-length probes are labeled by random priming with $[\alpha\text{-}^{32}P]dATP$. Hybridization is carried out under standard conditions against an RNA blot prepared from total RNA of flies harvested at different stages of development (embryos at hours 0-4, 4-8, 8-12, 12-24, larval instars $1^{st}$, $2^{nd}$, $3^{rd}$, early and late pupal stages, and adults). For in situ hybridization purposes, $^3H$ labeling is the most sensitive approach, and the very low energy of the beta particle emitted causes it to travel only short distances through the radiographic emulsion, allowing precise localization for the probe. However, digoxygenin labeling provides the advantage of being able to visualize hybridization with much higher spatial resolution because of the ability to directly visualize the tissue. Random primer labeling of DNA are performed with either tritium or digoxygenin labeled nucleotides. In situ hybridization is performed as described in Blair, S. (Blair S., 2000. Imaginal discs. In *Drosophila* Protocols. W. Sullivan, M. Ashburner, and R. Hawley, editors. Cold Spring Harbor Laboratory Example 9

Characterization of Sphingolipid Species in the Drosophila Melanogaster

Without being bound by theory, it is hypothesized that the phenotype of the SPL mutant Drosophila is caused by an abnormal level of S-1-P during development. Further, without being bound by theory, it is the inventors' hypothesis that phosphorylated sphingoid base species are responsible for regulating cell proliferation, migration and other events required for both tumor formation and normal developmental processes in this model organism. Therefore, characterization of sphingolipid species in Drosophila was determined.

Method: Wild type (Canton S) whole fly extracts were prepared by mechanical disruption. Lipids were isolated by two-phase extraction and derivatized with the fluorescent molecule o-pthalaldehyde essentially as described in Caligan, et al. hereby incorporated by reference in its entirety (Caligan, T. B., K. Peters, J. Ou, E. Wang, J. Saba, and A. H. Merrill, Jr. 2000. A high-performance liquid chromatographic method to measure sphingosine 1-phosphate and related compounds from sphingosine kinase assays and other biological samples. *Analytical Biochemistry.* 281:36-44). Derivatized lipid extracts were separated by HPLC using a $C_{18}$ ODS column (LUNA 4.6×250 mm) and mobile phase MeOH/H$_2$0/1M TBAP 82:17:0.9, pH 4.8. Standards included commercially available $C_{10}$, $C_{12}$, $C_{14}$, $C_{16}$, $C_{18}$ and $C_{20}$ sphingosines, as well as the phosphorylated forms of these standards, prepared by incubation of sphingosine standards with extract from a yeast strain which overexpresses the major yeast sphingosine kinase, LCB4.

Results: Drosophila extracts contained only sphingolipid species which comigrated with $C_{14}$ sphingosine and $C_{14}$ sphingosine-1-phosphate (S-1-P) standards under the stated conditions. To verify the identity of the peaks in fly extracts which comigrated with $C_{14}$sphingosine and $C_{14}$S-1-P standards, extracts and standards were compared in four different mobile phase buffers. The peak identified as $C_{14}$ sphingosine comigrated with the $C_{14}$ sphingosine standard under all four conditions (Table 1). However, the peak identified as $C_{14}$S-1-P demonstrated a slight difference from the $C_{14}$S-1-P standard under conditions which exploit differences in charge (MeOH/10 mM KP/1 M TBAP, pH 7.2, 81:18:1).

TABLE 1

Sphingolipid Identification

| Mobile Phase | $C_{14}$S std | $C_{14}$S in extract | $C_{14}$S-1-P std | $C_{14}$S-1-P in extract |
|---|---|---|---|---|
| MeOH/H$_2$0/1M TBAP pH 4.8 82.1:17:0.9 | 19.1 min | 19.0 min | 14.8 min | 14.8 min |
| MeOH/H$_2$0/1M TBAP pH 4.8 79.1:20:0.9 | 27.3 min | 27.1 min | 22.5 min | 22.1 min |
| MeOH/10 mM KP/ 1M TBAP pH 5.5 81:18.1 | 21.9 min | 22.0 min | 18.3 min | 17.2 min |
| MeOH/10 mM KP/ 1M TBAP pH 7.2 81:18.1 | 21.4 min | 21.8 min | 15.0 min | 17.1 min |

This finding is likely to be due to a chemical modification of the phosphate group, since a phosphatase capable of dephosphorylating the $C_{14}$S-1-P standard does not recognize this substrate. Mass spectroscopy is utilized to identify the phosphate group modification of this S-1-P species. Herein, this sphingolipid is referred to as "modified $C_{14}$S-1-P."

Example 10

Characterization of Sphingolipid Species in the Drosophila SPL Mutant

Differences in the quantity or type of sphingolipid species present in mutant versus wild type adult flies and during various stages of development was determined as described below.

Methods were as described in Example 9.

Results: The modified $C_{14}$S-1-P peak was ten-fold higher in the Drosophila SPL mutant than in the wild type (using an internal standard to normalize for extraction variation), supporting the notion that the phenotype of the SPL mutant may be due to abnormal accumulation of phosphorylated sphingoid bases and resulting abnormalities in signaling. $C_{14}$ sphingosine was also increased in the mutant, but to a lesser extent (Table 2). No other peaks in the mutant demonstrated a significant difference in comparison to wild type controls.

TABLE 2

Sphingolipid Quantification (nmol/200 mg flies)

| Line (n = 3) | modified $C_{14}$S-1-P | $C_{14}$S |
|---|---|---|
| Canton S (wild type) | 0.49 ± 0.07 | 2.61 ± 0.27 |
| SPL mutant | 4.49 ± 0.53 | 5.27 ± 0.73 |

Example 11

Characterization of the SPL Activity Encoded by ESTs LP04413/GH3783 and which is Absent in Insertional Mutant 11393

Drosophila ESTs LP04413 and GH3783 encode a protein with strong homology to other sphingosine phosphate lyases (SPL). Mutant 11393 which demonstrates the flight defect and dorsal longitudinal muscle (DLM) abnormalities described above in Example 7, contains a p-element insertion within this locus. Initial results using a standard SPL assay and a radiolabelled $C_{18}$DHS-1-P substrate indicated that Drosophila ESTs LP04413 and GH3783 encode an SPL, since expression restored SPL activity to a yeast SPL mutant. However, the activity conferred by the EST expression in yeast was not pronounced. Since Drosophila extracts contain $C_{14}$ sphingosine and a modified species of $C_{14}$S-1-P, it was hypothesized that the $C_{18}$DHS-1-P was not a favorable substrate for the major Drosophila lyase. Further, residual lyase activity observed in the mutant indicated the presence of more than one SPL activity in Drosophila. Therefore, the optimal substrate of the SPL encoded by ESTs LP04413 and GH3783 was determined and this activity was differentiated from other SPL activities in Drosophila.

Methods: Wild type (Canton S) and mutant whole fly extracts were prepared by mechanical disruption. Standard SPL assays using $C_{18}$ DHS-1-P substrate were performed as previously described (Van Veldhoven, P. P., and G. P. Mannaerts. 1991. Subcellular localization and membrane topology of sphingosine-1-phosphate lyase in rat liver. *J Biol Chem.* 266:12502-12507). An HPLC-based SPL assay was established, to allow for various non-radioactive substrates to be evaluated. For this assay, $C_{14}$S-1-P, $C_{18}$DHS-1-P and modified $C_{14}$S-1-P were prepared by drying down the lipid extract from 15 mg of 11939 flies, plus 200 pmol $C_{14}$S-1-P standard and 200 pmol $C_{18}$DHS-1-P standard. Lipids were resuspended in 25 μl of 1% Triton X-100 in potassium phosphate buffer, pH 7.4. 175 μl of reaction buffer (KP buffer, NaF, DTT, EDTA, sucrose) were added, and mixture was tip sonicated for 20 seconds, followed by addition of 50 μg of protein from whole cell extract of flies (CS or 11939) or Δdpl1:lcb4 yeast overexpressing the fly lyase. Incubation proceeded for 1 hr at 37° C. Reaction was stopped by adding 175 μl of MeOH containing 0.2% acetic acid. The reaction was applied to STRATA C18 column in 40% MeOH containing 0.1% acetic acid. The column was washed with 600 μl of 40% MeOH containing 0.1% acetic acid. Lipids were eluted with 1 ml of 90% MeOH/10% 10 mM K-Phosphate, pH 7.2. Samples were dried and resuspended in MeOH, treated with o-pthalaldehyde and injected on the HPLC. The degradation of S-1-P standards and modified $C_{14}$S-1-P were compared to standards incubated in the absence of protein extracts.

Results: An activity which metabolizes modified $C_{14}$S-1-P is present in wild type fly extracts but is absent in the mutant fly extracts. Residual SPL activity does exist in the mutant fly. This activity is distinct from that encoded by LP04413/GH3783, in that it metabolizes $C_{14}$S-1-P and $C_{18}$DHS-1-P with an efficacy similar to or better than wild type. The pH curve of the residual SPL activity in mutant flies is identical to that seen in wild type flies (against a $C_{18}$DHS-1-P substrate), indicating that this activity is not disrupted in the mutant.

Example 12

Further Characterization of the *Drosophila melanogaster* SPL Mutant Phenotype

Adult SPL mutant flies demonstrated inability to fly and abnormal patterning of indirect flight muscles. The adult SPL mutant flies consistently demonstrated abnormal patterning of DLMs, although the number of remaining DLMs varied in each mutant. In this Example, it was determined whether the abnormal muscle development was limited to the adult fly, or whether the defect was also present at earlier developmental stages.

Methods: Larval locomotor assay. Third instar larvae were placed on a clear agar substrate that overlays a grid. A light source at one end provided a photactic stimulus. Distance traveled was scored during three minute trials. Larval muscle microscopy. Larvae were filleted during the third instar and pinned with the dorsal cuticle down. The viscera were removed to allow an unobstructed view of the body wall muscles using polarized light. Muscles were refractile due to the presence of filamentous arrays in each muscle fiber.

Results: 11393 mutant larvae demonstrated significant defects in locomotion in comparison to wild type larvae, although phototactic response is intact. In all mutant larvae examined, the T2-dorsal oblique muscles exhibited alterations in number and/or size. Fused, hypertrophied residual dorsal obliques were observed in the mutants.

Since the four pairs of dorsal obliques in thoracic segment two create scaffolds which give rise during pupation to the DLM structures of the adult, it is likely that the developmental defect seen in the adult is the result of a process which begins much earlier, during larval development or embryogenesis.

Example 13

Human SPL Expression Patterns in Cancer

To determine if SPL expression is altered in human tumors, we utilized a cancer profiling array which contains more than 240 cDNA pairs representing tumor tissue and corresponding normal tissue from the same patient. By utilizing tissue pairs from one patient, differences between gene expression in tumor and normal tissue which might be due to person to person variability should not confound the interpretation of results. Additionally, each blot was normalized for loading using four separate housekeeping genes. Traditional hybridization techniques were utilized to probe this cDNA blot with a 300 nucleotide 3' fragment of human SPL cDNA (SEQ ID NO:7), which was obtained from the previously described cloning experiments. Analysis of the array indicated that, whereas human SPL expression is matched closely in most tissue pairs, it is significantly reduced in colon cancer specimens, with a 50% reduction in expression in colloid cancer of the colon and 61% reduction in adenocarcinoma of the colon. Reduced SPL expression was also seen in adenocarcinoma of the uterus. None of the tumors in which SPL expression is diminished demonstrate SK overexpression. Thus, altered SPL expression is observed in primary human tumors. Therefore, modulating the activity of SPL protein either by altering gene expression or through direct action on the protein may provide a useful treatment for individuals afflicted with an SPL-related cancer. Furthermore, SPL expression serves as a useful diagnostic marker of cancer in humans.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated antibody, or antigen-binding fragment thereof, that binds to
a polypeptide comprising the sequence recited in SEQ ID NO:8.

2. The isolated antibody, or antigen-binding fragment thereof, of claim 1, wherein the antibody is a monoclonal antibody.

3. The isolated antibody, or antigen-binding fragment thereof, according to claim 1 or claim 2, wherein the antibody, or antigen-binding fragment thereof, inhibits the ability of a polypeptide having a sequence recited in SEQ ID NO:8 to degrade sphingosine-1-phosphate.

4. A kit
comprising an antibody, or antigen-binding fragment thereof, according to claim 1 or claim 2 and a buffer or detection reagent.

5. The isolated antibody, or antigen-binding fragment thereof, of claim 1 or claim 2, wherein the antigen-binding fragment is selected from the group consisting of F(ab')2, -Fab', Fab and F[v] fragments.

6. The isolated antibody, or antigen-binding fragment thereof, of claim 3, wherein the antigen-binding fragment is selected from the group consisting of F(ab')2, Fab', Fab and F[v] fragments.

7. A method for detecting sphingosine-1-phosphate lyase in a sample, comprising:
(a) contacting a sample with an antibody, or antigen-binding fragment thereof, according to claim 1 or claim 2 under conditions and for a time sufficient to allow the antibody, or antigen-binding fragment thereof, to bind to sphingosine-1-phosphate lyase; and
(b) detecting in the sample the presence of sphingosine-1-phosphate lyase bound to the antibody, or antigen-binding fragment thereof.

* * * * *

SEQUENCE LISTING

<160> NUMBER OF SEQ ID NOS: 21

<210> SEQ ID NO 1
<211> LENGTH: 1770
<212> TYPE: DNA
<213> ORGANISM: S. cerevisiae
<220> FEATURE:
<221> NAME/KEY: CDS
<222> LOCATION: (1)...(1770)

<400> SEQUENCE: 1

```
atg agt gga gta tca aat aaa aca gta tca att aat ggt tgg tat ggc      48
Met Ser Gly Val Ser Asn Lys Thr Val Ser Ile Asn Gly Trp Tyr Gly
1               5                   10                  15 atg cca att cat tta cta agg gaa gaa ggc gac ttt gcc cag ttt atg      96
Met Pro Ile His Leu Leu Arg Glu Glu Gly Asp Phe Ala Gln Phe Met
            20                  25                  30 att cta acc atc aac gaa tta aaa ata gcc ata cat ggt tac ctc aga     144
Ile Leu Thr Ile Asn Glu Leu Lys Ile Ala Ile His Gly Tyr Leu Arg
        35                  40                  45 aat acc cca tgg tac aac atg ttg aag gat tat ttg ttt gtg atc ttt     192
Asn Thr Pro Trp Tyr Asn Met Leu Lys Asp Tyr Leu Phe Val Ile Phe
    50                  55                  60 tgt tac aag cta ata agt aat ttt ttt tat ctg ttg aaa gtt tat ggg     240
Cys Tyr Lys Leu Ile Ser Asn Phe Phe Tyr Leu Leu Lys Val Tyr Gly
65                  70                  75                  80 ccg gtg agg tta gca gtg aga aca tac gag cat agt tcc aga aga ttg     288
Pro Val Arg Leu Ala Val Arg Thr Tyr Glu His Ser Ser Arg Arg Leu
                85                  90                  95 ttt cgt tgg tta ttg gac tca cca ttt ttg agg ggt acc gta gaa aag     336
Phe Arg Trp Leu Leu Asp Ser Pro Phe Leu Arg Gly Thr Val Glu Lys
            100                 105                 110 gaa gtc aca aag gtc aaa caa tcg atc gaa gac gaa cta att aga tcg     384
Glu Val Thr Lys Val Lys Gln Ser Ile Glu Asp Glu Leu Ile Arg Ser
        115                 120                 125 gac tct cag tta atg aat ttc cca cag ttg cca tcc aat ggg ata cct     432
Asp Ser Gln Leu Met Asn Phe Pro Gln Leu Pro Ser Asn Gly Ile Pro
    130                 135                 140 cag gat gat gtt att gaa gag cta aat aaa ttg aac gac ttg ata cca     480
Gln Asp Asp Val Ile Glu Glu Leu Asn Lys Leu Asn Asp Leu Ile Pro
145                 150                 155                 160 cat acc caa tgg aag gaa gga aag gtc tct ggt gcc gtt tac cac ggt     528
His Thr Gln Trp Lys Glu Gly Lys Val Ser Gly Ala Val Tyr His Gly
                165                 170                 175 ggt gat gat ttg atc cac tta caa aca atc gca tac gaa aaa tat tgc     576
Gly Asp Asp Leu Ile His Leu Gln Thr Ile Ala Tyr Glu Lys Tyr Cys
            180                 185                 190 gtt gcc aat caa tta cat ccc gat gtc ttt cct gcc gta cgt aaa atg     624
Val Ala Asn Gln Leu His Pro Asp Val Phe Pro Ala Val Arg Lys Met
        195                 200                 205 gaa tcc gaa gtg gtt tct atg gtt tta aga atg ttt aat gcc cct tct     672
Glu Ser Glu Val Val Ser Met Val Leu Arg Met Phe Asn Ala Pro Ser
    210                 215                 220 gat aca ggt tgt ggt acc aca act tca ggt ggt aca gaa tcc ttg ctt     720
Asp Thr Gly Cys Gly Thr Thr Thr Ser Gly Gly Thr Glu Ser Leu Leu
225                 230                 235                 240 tta gca tgt ctg agc gct aaa atg tat gcc ctt cat cat cgt gga atc     768
Leu Ala Cys Leu Ser Ala Lys Met Tyr Ala Leu His His Arg Gly Ile
                245                 250                 255 acc gaa cca gaa ata att gct ccc gta act gca cat gct ggg ttt gac     816
Thr Glu Pro Glu Ile Ile Ala Pro Val Thr Ala His Ala Gly Phe Asp
            260                 265                 270 aaa gct gct tat tac ttt ggc atg aag cta cgc cac gtg gag cta gat     864
Lys Ala Ala Tyr Tyr Phe Gly Met Lys Leu Arg His Val Glu Leu Asp
        275                 280                 285 cca acg aca tat caa gtg gac ctg gga aaa gtg aaa aaa ttc atc aat     912
Pro Thr Thr Tyr Gln Val Asp Leu Gly Lys Val Lys Lys Phe Ile Asn
    290                 295                 300 aag aac aca att tta ctg gtc ggt tcc gct cca aac ttt cct cat ggt     960
Lys Asn Thr Ile Leu Leu Val Gly Ser Ala Pro Asn Phe Pro His Gly
```

```
Lys Asn Thr Ile Leu Leu Val Gly Ser Ala Pro Asn Phe Pro His Gly
305                 310                 315                 320 att gcc gat gat att gaa gga ttg ggt aaa ata gca caa aaa tat aaa    1008
Ile Ala Asp Asp Ile Glu Gly Leu Gly Lys Ile Ala Gln Lys Tyr Lys
                325                 330                 335 ctt cct tta cac gtc gac agt tgt cta ggt tcc ttt att gtt tca ttt    1056
Leu Pro Leu His Val Asp Ser Cys Leu Gly Ser Phe Ile Val Ser Phe
                340                 345                 350 atg gaa aag gct ggt tac aaa aat ctg cca tta ctt gac ttt aga gtc    1104
Met Glu Lys Ala Gly Tyr Lys Asn Leu Pro Leu Leu Asp Phe Arg Val
                355                 360                 365 ccg gga gtc acc tca ata tca tgt gac act cat aaa tat gga ttt gca    1152
Pro Gly Val Thr Ser Ile Ser Cys Asp Thr His Lys Tyr Gly Phe Ala
            370                 375                 380 cca aaa ggc tcg tca gtt ata atg tat aga aac agc gac tta cga atg    1200
Pro Lys Gly Ser Ser Val Ile Met Tyr Arg Asn Ser Asp Leu Arg Met
385                 390                 395                 400 cat cag tat tac gta aat cct gct tgg act ggc ggg tta tat ggc tct    1248
His Gln Tyr Tyr Val Asn Pro Ala Trp Thr Gly Gly Leu Tyr Gly Ser
                405                 410                 415 cct aca tta gca ggg tcc agg cct ggt gct att gtc gta ggt tgt tgg    1296
Pro Thr Leu Ala Gly Ser Arg Pro Gly Ala Ile Val Val Gly Cys Trp
            420                 425                 430 gcc act atg gtc aac atg ggt gaa aat ggg tac att gag tcg tgc caa    1344
Ala Thr Met Val Asn Met Gly Glu Asn Gly Tyr Ile Glu Ser Cys Gln
                435                 440                 445 gaa ata gtc ggt gca gca atg aag ttt aaa aaa tac atc cag gaa aac    1392
Glu Ile Val Gly Ala Ala Met Lys Phe Lys Lys Tyr Ile Gln Glu Asn
450                 455                 460 att cca gac ctg aat ata atg ggc aac cct aga tat tca gtc att tca    1440
Ile Pro Asp Leu Asn Ile Met Gly Asn Pro Arg Tyr Ser Val Ile Ser
465                 470                 475                 480 ttt tct tca aag acc ttg aac ata cac gaa cta tct gac agg ttg tcc    1488
Phe Ser Ser Lys Thr Leu Asn Ile His Glu Leu Ser Asp Arg Leu Ser
                485                 490                 495 aag aaa ggc tgg cat ttc aat gcc cta caa aag ccg gtt gca cta cac    1536
Lys Lys Gly Trp His Phe Asn Ala Leu Gln Lys Pro Val Ala Leu His
            500                 505                 510 atg gcc ttc acg aga ttg agc gct cat gtt gtg gat gag atc tgc gac    1584
Met Ala Phe Thr Arg Leu Ser Ala His Val Val Asp Glu Ile Cys Asp
            515                 520                 525 att tta cgt act acc gtg caa gag ttg aag agc gaa tca aat tct aaa    1632
Ile Leu Arg Thr Thr Val Gln Glu Leu Lys Ser Glu Ser Asn Ser Lys
530                 535                 540 cca tcc cca gac gga act agc gct cta tat ggt gtc gcc ggg agc gtt    1680
Pro Ser Pro Asp Gly Thr Ser Ala Leu Tyr Gly Val Ala Gly Ser Val
545                 550                 555                 560 aaa act gct ggc gtt gca gac aaa ttg att gtg gga ttc cta gac gca    1728
Lys Thr Ala Gly Val Ala Asp Lys Leu Ile Val Gly Phe Leu Asp Ala
                565                 570                 575 tta tac aag ttg ggt cca gga gag gat acc gcc acc aag tag            1770
Leu Tyr Lys Leu Gly Pro Gly Glu Asp Thr Ala Thr Lys *
            580                 585
```

<210> SEQ ID NO 2
<211> LENGTH: 589
<212> TYPE: PRT
<213> ORGANISM: S. cerevisiae

<400> SEQUENCE: 2

Met Ser Gly Val Ser Asn Lys Thr Val Ser Ile Asn Gly Trp Tyr Gly

-continued

```
              1               5                  10                 15
Met Pro Ile His Leu Arg Glu Glu Gly Asp Phe Ala Gln Phe Met
                20                 25                 30

Ile Leu Thr Ile Asn Glu Leu Lys Ile Ala Ile His Gly Tyr Leu Arg
                35                 40                 45

Asn Thr Pro Trp Tyr Asn Met Leu Lys Asp Tyr Leu Phe Val Ile Phe
 50                 55                 60

Cys Tyr Lys Leu Ile Ser Asn Phe Phe Tyr Leu Leu Lys Val Tyr Gly
 65                 70                 75                 80

Pro Val Arg Leu Ala Val Arg Thr Tyr Glu His Ser Ser Arg Arg Leu
                85                 90                 95

Phe Arg Trp Leu Leu Asp Ser Pro Phe Leu Arg Gly Thr Val Glu Lys
                100                105                110

Glu Val Thr Lys Val Lys Gln Ser Ile Glu Asp Glu Leu Ile Arg Ser
                115                120                125

Asp Ser Gln Leu Met Asn Phe Pro Gln Leu Pro Ser Asn Gly Ile Pro
                130                135                140

Gln Asp Asp Val Ile Glu Glu Leu Asn Lys Leu Asn Asp Leu Ile Pro
145                150                155                160

His Thr Gln Trp Lys Glu Gly Lys Val Ser Gly Ala Val Tyr His Gly
                165                170                175

Gly Asp Asp Leu Ile His Leu Gln Thr Ile Ala Tyr Glu Lys Tyr Cys
                180                185                190

Val Ala Asn Gln Leu His Pro Asp Val Phe Pro Ala Val Arg Lys Met
                195                200                205

Glu Ser Glu Val Val Ser Met Val Leu Arg Met Phe Asn Ala Pro Ser
                210                215                220

Asp Thr Gly Cys Gly Thr Thr Thr Ser Gly Gly Thr Glu Ser Leu Leu
225                230                235                240

Leu Ala Cys Leu Ser Ala Lys Met Tyr Ala Leu His His Arg Gly Ile
                245                250                255

Thr Glu Pro Glu Ile Ile Ala Pro Val Thr Ala His Ala Gly Phe Asp
                260                265                270

Lys Ala Ala Tyr Tyr Phe Gly Met Lys Leu Arg His Val Glu Leu Asp
                275                280                285

Pro Thr Thr Tyr Gln Val Asp Leu Gly Lys Val Lys Lys Phe Ile Asn
                290                295                300

Lys Asn Thr Ile Leu Leu Val Gly Ser Ala Pro Asn Phe Pro His Gly
305                310                315                320

Ile Ala Asp Asp Ile Glu Gly Leu Gly Lys Ile Ala Gln Lys Tyr Lys
                325                330                335

Leu Pro Leu His Val Asp Ser Cys Leu Gly Ser Phe Ile Val Ser Phe
                340                345                350

Met Glu Lys Ala Gly Tyr Lys Asn Leu Pro Leu Leu Asp Phe Arg Val
                355                360                365

Pro Gly Val Thr Ser Ile Ser Cys Asp Thr His Lys Tyr Gly Phe Ala
                370                375                380

Pro Lys Gly Ser Ser Val Ile Met Tyr Arg Asn Ser Asp Leu Arg Met
385                390                395                400

His Gln Tyr Tyr Val Asn Pro Ala Trp Thr Gly Gly Leu Tyr Gly Ser
                405                410                415

Pro Thr Leu Ala Gly Ser Arg Pro Gly Ala Ile Val Val Gly Cys Trp
                420                425                430
```

-continued

```
Ala Thr Met Val Asn Met Gly Glu Asn Gly Tyr Ile Glu Ser Cys Gln
        435                 440                 445

Glu Ile Val Gly Ala Ala Met Lys Phe Lys Lys Tyr Ile Gln Glu Asn
    450                 455                 460

Ile Pro Asp Leu Asn Ile Met Gly Asn Pro Arg Tyr Ser Val Ile Ser
465                 470                 475                 480

Phe Ser Ser Lys Thr Leu Asn Ile His Glu Leu Ser Asp Arg Leu Ser
                485                 490                 495

Lys Lys Gly Trp His Phe Asn Ala Leu Gln Lys Pro Val Ala Leu His
            500                 505                 510

Met Ala Phe Thr Arg Leu Ser Ala His Val Val Asp Glu Ile Cys Asp
        515                 520                 525

Ile Leu Arg Thr Thr Val Gln Glu Leu Lys Ser Glu Ser Asn Ser Lys
    530                 535                 540

Pro Ser Pro Asp Gly Thr Ser Ala Leu Tyr Gly Val Ala Gly Ser Val
545                 550                 555                 560

Lys Thr Ala Gly Val Ala Asp Lys Leu Ile Val Gly Phe Leu Asp Ala
                565                 570                 575

Leu Tyr Lys Leu Gly Pro Gly Glu Asp Thr Ala Thr Lys
            580                 585
```

<210> SEQ ID NO 3
<211> LENGTH: 1629
<212> TYPE: DNA
<213> ORGANISM: C. elegans
<220> FEATURE:
<221> NAME/KEY: CDS
<222> LOCATION: (1)...(1629)

<400> SEQUENCE: 3

```
atg gat ttt gca ctg gag caa tat cat agt gca aag gat ttg tta ata      48
Met Asp Phe Ala Leu Glu Gln Tyr His Ser Ala Lys Asp Leu Leu Ile
1               5                   10                  15 ttt gag ctt cga aag ttc aat cca att gtt ctg gtt tct agt act att      96
Phe Glu Leu Arg Lys Phe Asn Pro Ile Val Leu Val Ser Ser Thr Ile
            20                  25                  30 gtt gca aca tac gta ctc acc aat ctg aga cat atg cat tta gat gaa     144
Val Ala Thr Tyr Val Leu Thr Asn Leu Arg His Met His Leu Asp Glu
        35                  40                  45 atg ggc atc cgg aaa cgt ttg agc act tgg ttt ttc acc act gta aag     192
Met Gly Ile Arg Lys Arg Leu Ser Thr Trp Phe Phe Thr Thr Val Lys
    50                  55                  60 cgt gtg cct ttc atc agg aaa atg att gac aaa caa cta aac gaa gta     240
Arg Val Pro Phe Ile Arg Lys Met Ile Asp Lys Gln Leu Asn Glu Val
65                  70                  75                  80 aag gac gag ctt gag aaa agt ctg aga att gtg gat cga agc acc gaa     288
Lys Asp Glu Leu Glu Lys Ser Leu Arg Ile Val Asp Arg Ser Thr Glu
                85                  90                  95 tac ttc act aca atc cca agc cat tca gtt gga aga act gaa gta ctt     336
Tyr Phe Thr Thr Ile Pro Ser His Ser Val Gly Arg Thr Glu Val Leu
            100                 105                 110 cgc ctt gct gcc atc tat gat gat ttg gaa gga cca gct ttt ttg gaa     384
Arg Leu Ala Ala Ile Tyr Asp Asp Leu Glu Gly Pro Ala Phe Leu Glu
        115                 120                 125 gga aga gta tct gga gca gtc ttc aat aga gaa gac gac aag gac gaa     432
Gly Arg Val Ser Gly Ala Val Phe Asn Arg Glu Asp Asp Lys Asp Glu
    130                 135                 140 cgg gag atg tat gag gag gtg ttc gga aaa ttt gcc tgg acc aac cca     480
Arg Glu Met Tyr Glu Glu Val Phe Gly Lys Phe Ala Trp Thr Asn Pro
145                 150                 155                 160
```

| | | | | | | | | | | | | | | | | |
|---|---|---|---|---|---|---|---|---|---|---|---|---|---|---|---|---|
|ctt|tgg|cca|aaa|ttg|ttc|cct|gga|gtg|aga|atc|atg|gag|gct|gaa|gtt|528|
|Leu|Trp|Pro|Lys|Leu|Phe|Pro|Gly|Val|Arg|Ile|Met|Glu|Ala|Glu|Val| |
| | | |165| | | |170| | | |175| | | | | |

```
gtt cgc atg tgt tgt aat atg atg aat gga gat tcg gag aca tgt gga      576
Val Arg Met Cys Cys Asn Met Met Asn Gly Asp Ser Glu Thr Cys Gly
            180                 185                 190 act atg tca act ggt gga tcc att tca att ctt ttg gcg tgc ctg gct      624
Thr Met Ser Thr Gly Gly Ser Ile Ser Ile Leu Leu Ala Cys Leu Ala
    195                 200                 205 cat cgt aat cgt ctt ttg aaa aga gga gaa aag tac aca gag atg att      672
His Arg Asn Arg Leu Leu Lys Arg Gly Glu Lys Tyr Thr Glu Met Ile
210                 215                 220 gtc cca tca tcc gtc cat gca gcg ttc ttc aaa gct gcc gaa tgt ttc      720
Val Pro Ser Ser Val His Ala Ala Phe Phe Lys Ala Ala Glu Cys Phe
225                 230                 235                 240 cgt atc aaa gtt cgc aag att cca gtt gat cct gtt act ttc aaa gta      768
Arg Ile Lys Val Arg Lys Ile Pro Val Asp Pro Val Thr Phe Lys Val
            245                 250                 255 gac ctt gtc aaa atg aaa gcc gca att aac aag aga aca tgt atg tta      816
Asp Leu Val Lys Met Lys Ala Ala Ile Asn Lys Arg Thr Cys Met Leu
        260                 265                 270 gtt gga tct gct cca aac ttt cca ttt gga act gtt gat gac att gaa      864
Val Gly Ser Ala Pro Asn Phe Pro Phe Gly Thr Val Asp Asp Ile Glu
    275                 280                 285 gct att gga cag cta gga ctt gaa tat gac atc cca gtt cat gtt gat      912
Ala Ile Gly Gln Leu Gly Leu Glu Tyr Asp Ile Pro Val His Val Asp
    290                 295                 300 gct tgt ctt ggt ggt ttc ctt ctt cca ttc ctt gaa gaa gac gag att      960
Ala Cys Leu Gly Gly Phe Leu Leu Pro Phe Leu Glu Glu Asp Glu Ile
305                 310                 315                 320 cgc tat gac ttc cgt gtt cct ggt gta tct tcg att tct gca gat agt     1008
Arg Tyr Asp Phe Arg Val Pro Gly Val Ser Ser Ile Ser Ala Asp Ser
            325                 330                 335 cac aaa tac gga ctc gct cca aag ggg tca tca gtt gtt ctt tat cgc     1056
His Lys Tyr Gly Leu Ala Pro Lys Gly Ser Ser Val Val Leu Tyr Arg
        340                 345                 350 aat aag gaa ctt ctt cat aat cag tac ttc tgt gat gct gat tgg caa     1104
Asn Lys Glu Leu Leu His Asn Gln Tyr Phe Cys Asp Ala Asp Trp Gln
    355                 360                 365 gga ggt atc tat gca tcg gct act atg gaa gga tca cgc gct ggg cac     1152
Gly Gly Ile Tyr Ala Ser Ala Thr Met Glu Gly Ser Arg Ala Gly His
    370                 375                 380 aac att gca ctt tgc tgg gcc gca atg ctt tat cac gct cag gaa gga     1200
Asn Ile Ala Leu Cys Trp Ala Ala Met Leu Tyr His Ala Gln Glu Gly
385                 390                 395                 400 tac aag gcc aat gct aga aag att gtt gac act aca aga aag att aga     1248
Tyr Lys Ala Asn Ala Arg Lys Ile Val Asp Thr Thr Arg Lys Ile Arg
            405                 410                 415 aat gga ctt tca aac att aag gga atc aaa tta caa ggg cca agt gat     1296
Asn Gly Leu Ser Asn Ile Lys Gly Ile Lys Leu Gln Gly Pro Ser Asp
        420                 425                 430 gtt tgt att gtt agc tgg aca acc aat gat gga gtt gaa ctc tac aga     1344
Val Cys Ile Val Ser Trp Thr Thr Asn Asp Gly Val Glu Leu Tyr Arg
    435                 440                 445 ttc cat aac ttc atg aag gaa aaa cat tgg caa ctg aat gga ctt caa     1392
Phe His Asn Phe Met Lys Glu Lys His Trp Gln Leu Asn Gly Leu Gln
    450                 455                 460 ttc cca gct gga gtt cat atc atg gtc act atg aat cat act cat cct     1440
Phe Pro Ala Gly Val His Ile Met Val Thr Met Asn His Thr His Pro
465                 470                 475                 480
```

-continued

```
gga ctc gct gaa gct ttc gtc gcc gat tgc aga gct gca gtt gag ttt    1488
Gly Leu Ala Glu Ala Phe Val Ala Asp Cys Arg Ala Ala Val Glu Phe
            485                 490                 495 gtc aaa agc cac aaa cca tcg gaa tcc gac aag aca agt gaa gca gcc    1536
Val Lys Ser His Lys Pro Ser Glu Ser Asp Lys Thr Ser Glu Ala Ala
        500                 505                 510 atc tac gga ctt gct caa agt att cca gac cga tcg ctt gtt cac gag    1584
Ile Tyr Gly Leu Ala Gln Ser Ile Pro Asp Arg Ser Leu Val His Glu
        515                 520                 525 ttt gct cac agc tat atc gat gct gtt tat gct tta aca gag tga        1629
Phe Ala His Ser Tyr Ile Asp Ala Val Tyr Ala Leu Thr Glu *
        530                 535                 540
```

<210> SEQ ID NO 4
<211> LENGTH: 542
<212> TYPE: PRT
<213> ORGANISM: C. elegans

<400> SEQUENCE: 4

```
Met Asp Phe Ala Leu Glu Gln Tyr His Ser Ala Lys Asp Leu Leu Ile
  1               5                  10                  15

Phe Glu Leu Arg Lys Phe Asn Pro Ile Val Leu Val Ser Ser Thr Ile
                 20                  25                  30

Val Ala Thr Tyr Val Leu Thr Asn Leu Arg His Met His Leu Asp Glu
             35                  40                  45

Met Gly Ile Arg Lys Arg Leu Ser Thr Trp Phe Phe Thr Thr Val Lys
         50                  55                  60

Arg Val Pro Phe Ile Arg Lys Met Ile Asp Lys Gln Leu Asn Glu Val
 65                  70                  75                  80

Lys Asp Glu Leu Glu Lys Ser Leu Arg Ile Val Asp Arg Ser Thr Glu
                 85                  90                  95

Tyr Phe Thr Thr Ile Pro Ser His Ser Val Gly Arg Thr Glu Val Leu
            100                 105                 110

Arg Leu Ala Ala Ile Tyr Asp Asp Leu Glu Gly Pro Ala Phe Leu Glu
        115                 120                 125

Gly Arg Val Ser Gly Ala Val Phe Asn Arg Glu Asp Lys Asp Glu
        130                 135                 140

Arg Glu Met Tyr Glu Glu Val Phe Gly Lys Phe Ala Trp Thr Asn Pro
145                 150                 155                 160

Leu Trp Pro Lys Leu Phe Pro Gly Val Arg Ile Met Glu Ala Glu Val
                165                 170                 175

Val Arg Met Cys Cys Asn Met Met Asn Gly Asp Ser Glu Thr Cys Gly
            180                 185                 190

Thr Met Ser Thr Gly Gly Ser Ile Ser Ile Leu Leu Ala Cys Leu Ala
        195                 200                 205

His Arg Asn Arg Leu Leu Lys Arg Gly Glu Lys Tyr Thr Glu Met Ile
    210                 215                 220

Val Pro Ser Ser Val His Ala Ala Phe Phe Lys Ala Ala Glu Cys Phe
225                 230                 235                 240

Arg Ile Lys Val Arg Lys Ile Pro Val Asp Pro Val Thr Phe Lys Val
                245                 250                 255

Asp Leu Val Lys Met Lys Ala Ala Ile Asn Lys Arg Thr Cys Met Leu
            260                 265                 270

Val Gly Ser Ala Pro Asn Phe Pro Phe Gly Thr Val Asp Asp Ile Glu
        275                 280                 285

Ala Ile Gly Gln Leu Gly Leu Glu Tyr Asp Ile Pro Val His Val Asp
```

```
                      290                     295                      300
Ala Cys Leu Gly Gly Phe Leu Pro Phe Leu Glu Glu Asp Glu Ile
305                     310                     315                      320

Arg Tyr Asp Phe Arg Val Pro Gly Val Ser Ser Ile Ser Ala Asp Ser
                    325                     330                     335

His Lys Tyr Gly Leu Ala Pro Lys Gly Ser Ser Val Val Leu Tyr Arg
                    340                     345                     350

Asn Lys Glu Leu Leu His Asn Gln Tyr Phe Cys Asp Ala Asp Trp Gln
                    355                     360                     365

Gly Gly Ile Tyr Ala Ser Ala Thr Met Glu Gly Ser Arg Ala Gly His
                    370                     375                     380

Asn Ile Ala Leu Cys Trp Ala Ala Met Leu Tyr His Ala Gln Glu Gly
385                     390                     395                      400

Tyr Lys Ala Asn Ala Arg Lys Ile Val Asp Thr Arg Lys Ile Arg
                    405                     410                     415

Asn Gly Leu Ser Asn Ile Lys Gly Ile Lys Leu Gln Gly Pro Ser Asp
                    420                     425                     430

Val Cys Ile Val Ser Trp Thr Thr Asn Asp Gly Val Glu Leu Tyr Arg
                    435                     440                     445

Phe His Asn Phe Met Lys Glu Lys His Trp Gln Leu Asn Gly Leu Gln
                    450                     455                     460

Phe Pro Ala Gly Val His Ile Met Val Thr Met Asn His Thr His Pro
465                     470                     475                      480

Gly Leu Ala Glu Ala Phe Val Ala Asp Cys Arg Ala Ala Val Glu Phe
                    485                     490                     495

Val Lys Ser His Lys Pro Ser Glu Ser Asp Lys Thr Ser Glu Ala Ala
                    500                     505                     510

Ile Tyr Gly Leu Ala Gln Ser Ile Pro Asp Arg Ser Leu Val His Glu
                    515                     520                     525

Phe Ala His Ser Tyr Ile Asp Ala Val Tyr Ala Leu Thr Glu
                    530                     535                     540

<210> SEQ ID NO 5
<211> LENGTH: 1707
<212> TYPE: DNA
<213> ORGANISM: Mus musculus
<220> FEATURE:
<221> NAME/KEY: CDS
<222> LOCATION: (1)...(1707)

<400> SEQUENCE: 5 atg ccc gga acc gac ctc ctc aag ctg aag gac ttc gag cct tat ttg      48
Met Pro Gly Thr Asp Leu Leu Lys Leu Lys Asp Phe Glu Pro Tyr Leu
1               5                   10                  15 gag att ttg gaa tct tat tcc aca aaa gcc aag aat tat gtg aat gga      96
Glu Ile Leu Glu Ser Tyr Ser Thr Lys Ala Lys Asn Tyr Val Asn Gly
            20                  25                  30 tat tgc acc aaa tat gag ccc tgg cag ctc att gcg tgg agt gtc ctg     144
Tyr Cys Thr Lys Tyr Glu Pro Trp Gln Leu Ile Ala Trp Ser Val Leu
        35                  40                  45 tgt act ctg ctg ata gtc tgg gtg tat gag ctt atc ttc cag cca gag     192
Cys Thr Leu Leu Ile Val Trp Val Tyr Glu Leu Ile Phe Gln Pro Glu
    50                  55                  60 agt tta tgg tct cgg ttt aaa aaa aaa tta ttt aag ctt atc agg aag     240
Ser Leu Trp Ser Arg Phe Lys Lys Lys Leu Phe Lys Leu Ile Arg Lys
65                  70                  75                  80 atg cca ttt att gga cgt aag atc gaa caa cag gtg agc aaa gcc aag     288
Met Pro Phe Ile Gly Arg Lys Ile Glu Gln Gln Val Ser Lys Ala Lys
```

-continued

|     |     |     | 85  |     |     |     | 90  |     |     |     | 95  |     |     |      |
|-----|-----|-----|-----|-----|-----|-----|-----|-----|-----|-----|-----|-----|-----|------|
aag gat ctt gtc aag aac atg cca ttc cta aag gtg gac aag gat tat    336
Lys Asp Leu Val Lys Asn Met Pro Phe Leu Lys Val Asp Lys Asp Tyr
        100                 105                 110 gtg aaa act ctg cct gct cag ggt atg ggc aca gct gag gtt ctg gag    384
Val Lys Thr Leu Pro Ala Gln Gly Met Gly Thr Ala Glu Val Leu Glu
        115                 120                 125 aga ctc aag gag tac agc tcc atg gat ggt tcc tgg caa gaa ggg aaa    432
Arg Leu Lys Glu Tyr Ser Ser Met Asp Gly Ser Trp Gln Glu Gly Lys
    130                 135                 140 gcc tca gga gct gtg tac aat ggg gaa ccg aag ctc acg gag ctg ctg    480
Ala Ser Gly Ala Val Tyr Asn Gly Glu Pro Lys Leu Thr Glu Leu Leu
145                 150                 155                 160 gtg cag gct tat gga gaa ttc acg tgg agc aat cca ctg cat cca gat    528
Val Gln Ala Tyr Gly Glu Phe Thr Trp Ser Asn Pro Leu His Pro Asp
                165                 170                 175 atc ttc cct gga ttg cgg aag tta gag gca gaa atc gtt agg atg act    576
Ile Phe Pro Gly Leu Arg Lys Leu Glu Ala Glu Ile Val Arg Met Thr
            180                 185                 190 tgt tcc ctc ttc aat ggg gga cca gat tcc tgt gga tgt gtg act tct    624
Cys Ser Leu Phe Asn Gly Gly Pro Asp Ser Cys Gly Cys Val Thr Ser
        195                 200                 205 ggg gga acg gaa agc atc ctg atg gcc tgc aaa gct tac cgg gac ttg    672
Gly Gly Thr Glu Ser Ile Leu Met Ala Cys Lys Ala Tyr Arg Asp Leu
        210                 215                 220 gcg tta gag aag ggg atc aaa act cca gaa att gtg gct ccc gag agt    720
Ala Leu Glu Lys Gly Ile Lys Thr Pro Glu Ile Val Ala Pro Glu Ser
225                 230                 235                 240 gcc cat gct gca ttc gac aaa gca gct cat tat ttt ggg atg aag att    768
Ala His Ala Ala Phe Asp Lys Ala Ala His Tyr Phe Gly Met Lys Ile
                245                 250                 255 gtc cga gtt gca ctg aaa aag aac atg gag gtg gat gtg cag gca atg    816
Val Arg Val Ala Leu Lys Lys Asn Met Glu Val Asp Val Gln Ala Met
            260                 265                 270 aag aga gcc atc tcc agg aac aca gct atg ctg gtc tgt tct acc cca    864
Lys Arg Ala Ile Ser Arg Asn Thr Ala Met Leu Val Cys Ser Thr Pro
        275                 280                 285 cag ttt cct cat ggt gtg atg gat cct gtc ccc gaa gtg gcc aag tta    912
Gln Phe Pro His Gly Val Met Asp Pro Val Pro Glu Val Ala Lys Leu
        290                 295                 300 act gtc aga tat aaa atc cca ctc cat gtg gat gct tgt ctg ggg ggc    960
Thr Val Arg Tyr Lys Ile Pro Leu His Val Asp Ala Cys Leu Gly Gly
305                 310                 315                 320 ttc ctc att gtc ttc atg gag aaa gca ggg tac cca ctg gag aaa cca    1008
Phe Leu Ile Val Phe Met Glu Lys Ala Gly Tyr Pro Leu Glu Lys Pro
                325                 330                 335 ttt gat ttc cgg gtg aaa ggt gtg acc agc att tca gca gat act cat    1056
Phe Asp Phe Arg Val Lys Gly Val Thr Ser Ile Ser Ala Asp Thr His
            340                 345                 350 aag tat ggc tat gct cct aaa ggt tca tca gtg gtg atg tac tct aac    1104
Lys Tyr Gly Tyr Ala Pro Lys Gly Ser Ser Val Val Met Tyr Ser Asn
        355                 360                 365 gag aag tac agg acg tac cag ttc ttt gtt ggt gca gac tgg caa ggt    1152
Glu Lys Tyr Arg Thr Tyr Gln Phe Phe Val Gly Ala Asp Trp Gln Gly
        370                 375                 380 ggt gtc tac gca tct cca agc ata gct ggc tca cgg cct ggt ggc atc    1200
Gly Val Tyr Ala Ser Pro Ser Ile Ala Gly Ser Arg Pro Gly Gly Ile
385                 390                 395                 400 att gca gcc tgt tgg gcg gcc ttg atg cac ttc ggt gag aac ggc tat    1248
Ile Ala Ala Cys Trp Ala Ala Leu Met His Phe Gly Glu Asn Gly Tyr

```
                 405                 410                 415
gtt gaa gct acc aaa cag atc atc aaa act gct cgc ttc ctg aag tca    1296
Val Glu Ala Thr Lys Gln Ile Ile Lys Thr Ala Arg Phe Leu Lys Ser
            420                 425                 430 gaa ctg gaa aac atc aaa aac atc ttc att ttc ggt gat cct caa ttg    1344
Glu Leu Glu Asn Ile Lys Asn Ile Phe Ile Phe Gly Asp Pro Gln Leu
        435                 440                 445 tca gtt att gct ctg gga tcc aac gat ttt gac att tac cga cta tct    1392
Ser Val Ile Ala Leu Gly Ser Asn Asp Phe Asp Ile Tyr Arg Leu Ser
    450                 455                 460 aat atg atg tct gct aag ggg tgg aat ttt aac tac ctg cag ttc cca    1440
Asn Met Met Ser Ala Lys Gly Trp Asn Phe Asn Tyr Leu Gln Phe Pro
465                 470                 475                 480 aga agc att cat ttc tgc att acg tta gta cat act cgg aag cga gtg    1488
Arg Ser Ile His Phe Cys Ile Thr Leu Val His Thr Arg Lys Arg Val
                485                 490                 495 gcg atc cag ttc cta aag gat atc cgg gaa tca gtc aca caa atc atg    1536
Ala Ile Gln Phe Leu Lys Asp Ile Arg Glu Ser Val Thr Gln Ile Met
            500                 505                 510 aag aat cct aaa gct aag acc aca gga atg ggt gcc atc tat ggc atg    1584
Lys Asn Pro Lys Ala Lys Thr Thr Gly Met Gly Ala Ile Tyr Gly Met
        515                 520                 525 gcc cag gca acc att gac agg aag ctg gtt gca gaa ata tcc tcc gtc    1632
Ala Gln Ala Thr Ile Asp Arg Lys Leu Val Ala Glu Ile Ser Ser Val
    530                 535                 540 ttc ttg gac tgc ctt tat act acg gac ccc gtg act cag ggc aac cag    1680
Phe Leu Asp Cys Leu Tyr Thr Thr Asp Pro Val Thr Gln Gly Asn Gln
545                 550                 555                 560 atg aac ggt tct cca aag ccc cgc tga                                1707
Met Asn Gly Ser Pro Lys Pro Arg *
                565

<210> SEQ ID NO 6
<211> LENGTH: 568
<212> TYPE: PRT
<213> ORGANISM: Mus musculus

<400> SEQUENCE: 6

Met Pro Gly Thr Asp Leu Leu Lys Leu Lys Asp Phe Glu Pro Tyr Leu
1               5                   10                  15

Glu Ile Leu Glu Ser Tyr Ser Thr Lys Ala Lys Asn Tyr Val Asn Gly
            20                  25                  30

Tyr Cys Thr Lys Tyr Glu Pro Trp Gln Leu Ile Ala Trp Ser Val Leu
        35                  40                  45

Cys Thr Leu Leu Ile Val Trp Val Tyr Glu Leu Ile Phe Gln Pro Glu
    50                  55                  60

Ser Leu Trp Ser Arg Phe Lys Lys Leu Phe Lys Leu Ile Arg Lys
65              70                  75                  80

Met Pro Phe Ile Gly Arg Lys Ile Glu Gln Gln Val Ser Lys Ala Lys
            85                  90                  95

Lys Asp Leu Val Lys Asn Met Pro Phe Leu Lys Val Asp Lys Asp Tyr
        100                 105                 110

Val Lys Thr Leu Pro Ala Gln Gly Met Gly Thr Ala Glu Val Leu Glu
    115                 120                 125

Arg Leu Lys Glu Tyr Ser Ser Met Asp Gly Ser Trp Gln Glu Gly Lys
130                 135                 140

Ala Ser Gly Ala Val Tyr Asn Gly Glu Pro Lys Leu Thr Glu Leu Leu
145                 150                 155                 160
```

```
Val Gln Ala Tyr Gly Glu Phe Thr Trp Ser Asn Pro Leu His Pro Asp
                165                 170                 175
Ile Phe Pro Gly Leu Arg Lys Leu Glu Ala Glu Ile Val Arg Met Thr
            180                 185                 190
Cys Ser Leu Phe Asn Gly Gly Pro Asp Ser Cys Gly Cys Val Thr Ser
        195                 200                 205
Gly Gly Thr Glu Ser Ile Leu Met Ala Cys Lys Ala Tyr Arg Asp Leu
    210                 215                 220
Ala Leu Glu Lys Gly Ile Lys Thr Pro Glu Ile Val Ala Pro Glu Ser
225                 230                 235                 240
Ala His Ala Ala Phe Asp Lys Ala His Tyr Phe Gly Met Lys Ile
                245                 250                 255
Val Arg Val Ala Leu Lys Lys Asn Met Glu Val Asp Val Gln Ala Met
                260                 265                 270
Lys Arg Ala Ile Ser Arg Asn Thr Ala Met Leu Val Cys Ser Thr Pro
                275                 280                 285
Gln Phe Pro His Gly Val Met Asp Pro Val Pro Glu Val Ala Lys Leu
                290                 295                 300
Thr Val Arg Tyr Lys Ile Pro Leu His Val Asp Ala Cys Leu Gly Gly
305                 310                 315                 320
Phe Leu Ile Val Phe Met Glu Lys Ala Gly Tyr Pro Leu Glu Lys Pro
                325                 330                 335
Phe Asp Phe Arg Val Lys Gly Val Thr Ser Ile Ser Ala Asp Thr His
                340                 345                 350
Lys Tyr Gly Tyr Ala Pro Lys Gly Ser Ser Val Val Met Tyr Ser Asn
                355                 360                 365
Glu Lys Tyr Arg Thr Tyr Gln Phe Phe Val Gly Ala Asp Trp Gln Gly
        370                 375                 380
Gly Val Tyr Ala Ser Pro Ser Ile Ala Gly Ser Arg Pro Gly Gly Ile
385                 390                 395                 400
Ile Ala Ala Cys Trp Ala Ala Leu Met His Phe Gly Glu Asn Gly Tyr
                405                 410                 415
Val Glu Ala Thr Lys Gln Ile Ile Lys Thr Ala Arg Phe Leu Lys Ser
                420                 425                 430
Glu Leu Glu Asn Ile Lys Asn Ile Phe Ile Phe Gly Asp Pro Gln Leu
        435                 440                 445
Ser Val Ile Ala Leu Gly Ser Asn Asp Phe Asp Ile Tyr Arg Leu Ser
    450                 455                 460
Asn Met Met Ser Ala Lys Gly Trp Asn Phe Asn Tyr Leu Gln Phe Pro
465                 470                 475                 480
Arg Ser Ile His Phe Cys Ile Thr Leu Val His Thr Arg Lys Arg Val
                485                 490                 495
Ala Ile Gln Phe Leu Lys Asp Ile Arg Glu Ser Val Thr Gln Ile Met
                500                 505                 510
Lys Asn Pro Lys Ala Lys Thr Thr Gly Met Gly Ala Ile Tyr Gly Met
            515                 520                 525
Ala Gln Ala Thr Ile Asp Arg Lys Leu Val Ala Glu Ile Ser Ser Val
        530                 535                 540
Phe Leu Asp Cys Leu Tyr Thr Thr Asp Pro Val Thr Gln Gly Asn Gln
545                 550                 555                 560
Met Asn Gly Ser Pro Lys Pro Arg
                565

<210> SEQ ID NO 7
```

<211> LENGTH: 1707
<212> TYPE: DNA
<213> ORGANISM: Homo sapiens
<220> FEATURE:
<221> NAME/KEY: CDS
<222> LOCATION: (1)...(1707)

<400> SEQUENCE: 7

```
atg cct agc aca gac ctt ctg atg ttg aag gcc ttt gag ccc tac tta      48
Met Pro Ser Thr Asp Leu Leu Met Leu Lys Ala Phe Glu Pro Tyr Leu
 1               5                  10                  15 gag att ttg gaa gta tac tcc aca aaa gcc aag aat tat gta aat gga      96
Glu Ile Leu Glu Val Tyr Ser Thr Lys Ala Lys Asn Tyr Val Asn Gly
             20                  25                  30 cat tgc acc aag tat gag ccc tgg cag cta att gca tgg agt gtc gtg    144
His Cys Thr Lys Tyr Glu Pro Trp Gln Leu Ile Ala Trp Ser Val Val
         35                  40                  45 tgg acc ctg ctg ata gtc tgg gga tat gag ttt gtc ttc cag cca gag    192
Trp Thr Leu Leu Ile Val Trp Gly Tyr Glu Phe Val Phe Gln Pro Glu
     50                  55                  60 agt tta tgg tca agg ttt aaa aag aaa tgt ttt aag ctc acc agg aag    240
Ser Leu Trp Ser Arg Phe Lys Lys Lys Cys Phe Lys Leu Thr Arg Lys
 65                  70                  75                  80 atg ccc att att ggt cgt aag att caa gac aag ttg aac aag acc aag    288
Met Pro Ile Ile Gly Arg Lys Ile Gln Asp Lys Leu Asn Lys Thr Lys
                 85                  90                  95 gat gat att agc aag aac atg tca ttc ctg aaa gtg gac aaa gag tat    336
Asp Asp Ile Ser Lys Asn Met Ser Phe Leu Lys Val Asp Lys Glu Tyr
            100                 105                 110 gtg aaa gct tta ccc tcc cag ggt ctg agc tca tct gct gtt ttg gag    384
Val Lys Ala Leu Pro Ser Gln Gly Leu Ser Ser Ser Ala Val Leu Glu
        115                 120                 125 aaa ctt aag gag tac agc tct atg gac gcc ttc tgg caa gag ggg aga    432
Lys Leu Lys Glu Tyr Ser Ser Met Asp Ala Phe Trp Gln Glu Gly Arg
    130                 135                 140 gcc tct gga aca gtg tac agt ggg gag gag aag ctc act gag ctc ctt    480
Ala Ser Gly Thr Val Tyr Ser Gly Glu Glu Lys Leu Thr Glu Leu Leu
145                 150                 155                 160 gtg aag gct tat gga gat ttt gca tgg agt aac ccc ctg cat cca gat    528
Val Lys Ala Tyr Gly Asp Phe Ala Trp Ser Asn Pro Leu His Pro Asp
                165                 170                 175 atc ttc cca gga cta cgc aag ata gag gca gaa att gtg agg ata gct    576
Ile Phe Pro Gly Leu Arg Lys Ile Glu Ala Glu Ile Val Arg Ile Ala
            180                 185                 190 tgt tcc ctg ttc aat ggg gga cca gat tcg tgt gga tgt gtg act tct    624
Cys Ser Leu Phe Asn Gly Gly Pro Asp Ser Cys Gly Cys Val Thr Ser
        195                 200                 205 ggg gga aca gaa agc ata ctc atg gcc tgc aaa gca tgt cgg gat ctg    672
Gly Gly Thr Glu Ser Ile Leu Met Ala Cys Lys Ala Cys Arg Asp Leu
    210                 215                 220 gcc ttt gag aag ggg atc aaa act cca gaa att gtg gct ccc caa agt    720
Ala Phe Glu Lys Gly Ile Lys Thr Pro Glu Ile Val Ala Pro Gln Ser
225                 230                 235                 240 gcc cat gct gca ttt aac aaa gca gcc agt tac ttt ggg atg aag att    768
Ala His Ala Ala Phe Asn Lys Ala Ala Ser Tyr Phe Gly Met Lys Ile
                245                 250                 255 gtg cgg gtc cca ttg acg aag atg atg gag gtg gat gtg agg gca atg    816
Val Arg Val Pro Leu Thr Lys Met Met Glu Val Asp Val Arg Ala Met
            260                 265                 270 aga aga gct atc tcc agg aac act gcc atg ctc gtc tgt tct acc cca    864
Arg Arg Ala Ile Ser Arg Asn Thr Ala Met Leu Val Cys Ser Thr Pro
        275                 280                 285
```

```
cag ttt cct cat ggt gta ata gat cct gtc cct gaa gtg gcc aag ctg      912
Gln Phe Pro His Gly Val Ile Asp Pro Val Pro Glu Val Ala Lys Leu
    290                 295                 300 gct gtc aaa tac aaa ata ccc ctt cat gtc gac gct tgt ctg gga ggc      960
Ala Val Lys Tyr Lys Ile Pro Leu His Val Asp Ala Cys Leu Gly Gly
305                 310                 315                 320 ttc ctc atc gtc ttt atg gag aaa gca gga tac cca ctg gag cac cca     1008
Phe Leu Ile Val Phe Met Glu Lys Ala Gly Tyr Pro Leu Glu His Pro
                325                 330                 335 ttt gat ttc cgg gtg aaa ggt gta acc agc att tca gct gac acc cat     1056
Phe Asp Phe Arg Val Lys Gly Val Thr Ser Ile Ser Ala Asp Thr His
            340                 345                 350 aag tat ggc tat gcc cca aaa ggc tca tca ttg gtg ttg tat agt gac     1104
Lys Tyr Gly Tyr Ala Pro Lys Gly Ser Ser Leu Val Leu Tyr Ser Asp
        355                 360                 365 aag aag tac agg aac tat cag ttc ttc gtc gat aca gat tgg cag ggt     1152
Lys Lys Tyr Arg Asn Tyr Gln Phe Phe Val Asp Thr Asp Trp Gln Gly
    370                 375                 380 ggc atc tat gct tcc cca acc atc gca ggc tca cgg cct ggt ggc att     1200
Gly Ile Tyr Ala Ser Pro Thr Ile Ala Gly Ser Arg Pro Gly Gly Ile
385                 390                 395                 400 agc gca gcc tgt tgg gct gcc ttg atg cac ttc ggt gag aac ggc tat     1248
Ser Ala Ala Cys Trp Ala Ala Leu Met His Phe Gly Glu Asn Gly Tyr
                405                 410                 415 gtt gaa gct acc aaa cag atc atc aaa act gct cgc ttc ctc aag tca     1296
Val Glu Ala Thr Lys Gln Ile Ile Lys Thr Ala Arg Phe Leu Lys Ser
            420                 425                 430 gaa ctg gaa aat atc aaa ggc atc ttt gtt ttt ggg aat ccc caa ttg     1344
Glu Leu Glu Asn Ile Lys Gly Ile Phe Val Phe Gly Asn Pro Gln Leu
        435                 440                 445 tca ctc att gct ctg gga tcc cgt gat ttt gac atc tac cga cta tca     1392
Ser Leu Ile Ala Leu Gly Ser Arg Asp Phe Asp Ile Tyr Arg Leu Ser
    450                 455                 460 aac ctg atg act gct aag ggg tgg aac ttg aac cag ttg cag ttc cca     1440
Asn Leu Met Thr Ala Lys Gly Trp Asn Leu Asn Gln Leu Gln Phe Pro
465                 470                 475                 480 ccc agt att cat ttc tgc atc aca tta cta cac gcc cgg aaa cga gta     1488
Pro Ser Ile His Phe Cys Ile Thr Leu Leu His Ala Arg Lys Arg Val
                485                 490                 495 gct ata caa ttc cta aag gac att cga gaa tct gtc act caa atc atg     1536
Ala Ile Gln Phe Leu Lys Asp Ile Arg Glu Ser Val Thr Gln Ile Met
            500                 505                 510 aag aat cct aaa gcg aag acc aca gga atg ggt gcc atc tat gcc atg     1584
Lys Asn Pro Lys Ala Lys Thr Thr Gly Met Gly Ala Ile Tyr Ala Met
        515                 520                 525 gcc cag aca act gtt gac agg aat atg gtt gca gaa ttg tcc tca gtc     1632
Ala Gln Thr Thr Val Asp Arg Asn Met Val Ala Glu Leu Ser Ser Val
    530                 535                 540 ttc ttg gac agc ttg tac agc acc gac act gtc acc cag ggc agc cag     1680
Phe Leu Asp Ser Leu Tyr Ser Thr Asp Thr Val Thr Gln Gly Ser Gln
545                 550                 555                 560 atg aat ggt tct cca aaa ccc cac tga                                  1707
Met Asn Gly Ser Pro Lys Pro His *
                565
```

<210> SEQ ID NO 8
<211> LENGTH: 568
<212> TYPE: PRT
<213> ORGANISM: Homo sapiens

<400> SEQUENCE: 8

```
Met Pro Ser Thr Asp Leu Leu Met Leu Lys Ala Phe Glu Pro Tyr Leu
 1               5                  10                  15
Glu Ile Leu Glu Val Tyr Ser Thr Lys Ala Lys Asn Tyr Val Asn Gly
             20                  25                  30
His Cys Thr Lys Tyr Glu Pro Trp Gln Leu Ile Ala Trp Ser Val Val
             35                  40                  45
Trp Thr Leu Leu Ile Val Trp Gly Tyr Glu Phe Val Phe Gln Pro Glu
 50                  55                  60
Ser Leu Trp Ser Arg Phe Lys Lys Cys Phe Lys Leu Thr Arg Lys
 65                  70                  75                  80
Met Pro Ile Ile Gly Arg Lys Ile Gln Asp Lys Leu Asn Lys Thr Lys
                 85                  90                  95
Asp Asp Ile Ser Lys Asn Met Ser Phe Leu Lys Val Asp Lys Glu Tyr
                100                 105                 110
Val Lys Ala Leu Pro Ser Gln Gly Leu Ser Ser Ala Val Leu Glu
             115                 120                 125
Lys Leu Lys Glu Tyr Ser Ser Met Asp Ala Phe Trp Gln Glu Gly Arg
             130                 135                 140
Ala Ser Gly Thr Val Tyr Ser Gly Glu Glu Lys Leu Thr Glu Leu Leu
145                 150                 155                 160
Val Lys Ala Tyr Gly Asp Phe Ala Trp Ser Asn Pro Leu His Pro Asp
                165                 170                 175
Ile Phe Pro Gly Leu Arg Lys Ile Glu Ala Glu Ile Val Arg Ile Ala
                180                 185                 190
Cys Ser Leu Phe Asn Gly Gly Pro Asp Ser Cys Gly Cys Val Thr Ser
            195                 200                 205
Gly Gly Thr Glu Ser Ile Leu Met Ala Cys Lys Ala Cys Arg Asp Leu
            210                 215                 220
Ala Phe Glu Lys Gly Ile Lys Thr Pro Glu Ile Val Ala Pro Gln Ser
225                 230                 235                 240
Ala His Ala Ala Phe Asn Lys Ala Ala Ser Tyr Phe Gly Met Lys Ile
                245                 250                 255
Val Arg Val Pro Leu Thr Lys Met Met Glu Val Asp Val Arg Ala Met
                260                 265                 270
Arg Arg Ala Ile Ser Arg Asn Thr Ala Met Leu Val Cys Ser Thr Pro
            275                 280                 285
Gln Phe Pro His Gly Val Ile Asp Pro Val Pro Glu Val Ala Lys Leu
            290                 295                 300
Ala Val Lys Tyr Lys Ile Pro Leu His Val Asp Ala Cys Leu Gly Gly
305                 310                 315                 320
Phe Leu Ile Val Phe Met Glu Lys Ala Gly Tyr Pro Leu Glu His Pro
                325                 330                 335
Phe Asp Phe Arg Val Lys Gly Val Thr Ser Ile Ser Ala Asp Thr His
                340                 345                 350
Lys Tyr Gly Tyr Ala Pro Lys Gly Ser Ser Leu Val Leu Tyr Ser Asp
            355                 360                 365
Lys Lys Tyr Arg Asn Tyr Gln Phe Phe Val Asp Thr Asp Trp Gln Gly
            370                 375                 380
Gly Ile Tyr Ala Ser Pro Thr Ile Ala Gly Ser Arg Pro Gly Gly Ile
385                 390                 395                 400
Ser Ala Ala Cys Trp Ala Ala Leu Met His Phe Gly Glu Asn Gly Tyr
                405                 410                 415
Val Glu Ala Thr Lys Gln Ile Ile Lys Thr Ala Arg Phe Leu Lys Ser
```

```
              420                 425                 430
Glu Leu Glu Asn Ile Lys Gly Ile Phe Val Phe Gly Asn Pro Gln Leu
            435                 440                 445

Ser Leu Ile Ala Leu Gly Ser Arg Asp Phe Asp Ile Tyr Arg Leu Ser
        450                 455                 460

Asn Leu Met Thr Ala Lys Gly Trp Asn Leu Asn Gln Leu Gln Phe Pro
465                 470                 475                 480

Pro Ser Ile His Phe Cys Ile Thr Leu Leu His Ala Arg Lys Arg Val
                485                 490                 495

Ala Ile Gln Phe Leu Lys Asp Ile Arg Glu Ser Val Thr Gln Ile Met
            500                 505                 510

Lys Asn Pro Lys Ala Lys Thr Thr Gly Met Gly Ala Ile Tyr Ala Met
        515                 520                 525

Ala Gln Thr Thr Val Asp Arg Asn Met Val Ala Glu Leu Ser Ser Val
    530                 535                 540

Phe Leu Asp Ser Leu Tyr Ser Thr Asp Thr Val Thr Gln Gly Ser Gln
545                 550                 555                 560

Met Asn Gly Ser Pro Lys Pro His
                565

<210> SEQ ID NO 9
<211> LENGTH: 1467
<212> TYPE: DNA
<213> ORGANISM: Homo sapiens
<220> FEATURE:
<221> NAME/KEY: CDS
<222> LOCATION: (1)...(1467)

<400> SEQUENCE: 9 atg cct agc aca gac ctt ctg atg ttg aag gcc ttt gag ccc tac tta      48
Met Pro Ser Thr Asp Leu Leu Met Leu Lys Ala Phe Glu Pro Tyr Leu
1               5                   10                  15 gag att ttg gaa gta tac tcc aca aaa gcc aag aat tat gta aat gga      96
Glu Ile Leu Glu Val Tyr Ser Thr Lys Ala Lys Asn Tyr Val Asn Gly
            20                  25                  30 cat tgc acc aag tat gag ccc tgg cag cta att gca tgg agt gtc gtg     144
His Cys Thr Lys Tyr Glu Pro Trp Gln Leu Ile Ala Trp Ser Val Val
        35                  40                  45 tgg acc ctg ctg ata gtc tgg gga tat gag ttt gtc ttc cag cca gag     192
Trp Thr Leu Leu Ile Val Trp Gly Tyr Glu Phe Val Phe Gln Pro Glu
    50                  55                  60 agt tta tgg tca agg ttt aaa aag aaa tgt ttt aag ctc acc agg aag     240
Ser Leu Trp Ser Arg Phe Lys Lys Lys Cys Phe Lys Leu Thr Arg Lys
65                  70                  75                  80 atg ccc att att ggt cgt aag att caa gac aag ttg aac aag acc aag     288
Met Pro Ile Ile Gly Arg Lys Ile Gln Asp Lys Leu Asn Lys Thr Lys
                85                  90                  95 gat gat att agc aag aac atg tca ttc ctg aaa gtg gac aaa gag tat     336
Asp Asp Ile Ser Lys Asn Met Ser Phe Leu Lys Val Asp Lys Glu Tyr
            100                 105                 110 gtg aaa gct tta ccc tcc cag ggt ctg agc tca tct gct gtt ttg gag     384
Val Lys Ala Leu Pro Ser Gln Gly Leu Ser Ser Ser Ala Val Leu Glu
        115                 120                 125 aaa ctt aag gag tac agc tct atg gac gcc ttc tgg caa gag ggg aga     432
Lys Leu Lys Glu Tyr Ser Ser Met Asp Ala Phe Trp Gln Glu Gly Arg
    130                 135                 140 gcc tct gga aca gtg tac agt ggg gag gag aag ctc act gag ctc ctt     480
Ala Ser Gly Thr Val Tyr Ser Gly Glu Glu Lys Leu Thr Glu Leu Leu
145                 150                 155                 160
```

```
gtg aag gct tat gga gat ttt gca tgg agt aac ccc ctg cat cca gat        528
Val Lys Ala Tyr Gly Asp Phe Ala Trp Ser Asn Pro Leu His Pro Asp
            165                 170                 175 atc ttc cca gga cta cgc aag ata gag gca gaa att gtg agg ata gct        576
Ile Phe Pro Gly Leu Arg Lys Ile Glu Ala Glu Ile Val Arg Ile Ala
        180                 185                 190 tgt tcc ctg ttc aat ggg gga cca gat tcg tgt gga tgt gtg act tct        624
Cys Ser Leu Phe Asn Gly Gly Pro Asp Ser Cys Gly Cys Val Thr Ser
    195                 200                 205 ggg gga aca gaa agc ata ctc atg gcc tgc aaa gca tgt cgg gat ctg        672
Gly Gly Thr Glu Ser Ile Leu Met Ala Cys Lys Ala Cys Arg Asp Leu
210                 215                 220 gcc ttt gag aag ggg atc aaa act cca gaa att gtg gct ccc caa agt        720
Ala Phe Glu Lys Gly Ile Lys Thr Pro Glu Ile Val Ala Pro Gln Ser
225                 230                 235                 240 gcc cat gct gca ttt aac aaa gca gcc agt tac ttt ggg atg aag att        768
Ala His Ala Ala Phe Asn Lys Ala Ala Ser Tyr Phe Gly Met Lys Ile
            245                 250                 255 gtg cgg gtc cca ttg acg aag atg atg gag gtg gat gtg agg gca atg        816
Val Arg Val Pro Leu Thr Lys Met Met Glu Val Asp Val Arg Ala Met
        260                 265                 270 aga aga gct atc tcc agg aac act gcc atg ctc gtc tgt tct acc cca        864
Arg Arg Ala Ile Ser Arg Asn Thr Ala Met Leu Val Cys Ser Thr Pro
    275                 280                 285 cag ttt cct cat ggt gta ata gat cct gtc cct gaa gtg gcc aag ctg        912
Gln Phe Pro His Gly Val Ile Asp Pro Val Pro Glu Val Ala Lys Leu
290                 295                 300 gct gtc aaa tac aaa ata ccc ctt cat gtc gac gct tgt ctg gga ggc        960
Ala Val Lys Tyr Lys Ile Pro Leu His Val Asp Ala Cys Leu Gly Gly
305                 310                 315                 320 ttc ctc atc gtc ttt atg gag aaa gca gga tac cca ctg gag cac cca       1008
Phe Leu Ile Val Phe Met Glu Lys Ala Gly Tyr Pro Leu Glu His Pro
            325                 330                 335 ttt gat ttc cgg gtg aaa ggt gta acc agc att tca gct gac acc cat       1056
Phe Asp Phe Arg Val Lys Gly Val Thr Ser Ile Ser Ala Asp Thr His
        340                 345                 350 aag ctg gaa aat atc aaa ggc atc ttt gtt ttt ggg aat ccc caa ttg       1104
Lys Leu Glu Asn Ile Lys Gly Ile Phe Val Phe Gly Asn Pro Gln Leu
    355                 360                 365 tca ctc att gct ctg gga tcc cgt gat ttt gac atc tac cga cta tca       1152
Ser Leu Ile Ala Leu Gly Ser Arg Asp Phe Asp Ile Tyr Arg Leu Ser
370                 375                 380 aac ctg atg act gct aag ggg tgg aac ttg aac cag ttg cag ttc cca       1200
Asn Leu Met Thr Ala Lys Gly Trp Asn Leu Asn Gln Leu Gln Phe Pro
385                 390                 395                 400 ccc agt att cat ttc tgc atc aca tta cta cac gcc cgg aaa cga gta       1248
Pro Ser Ile His Phe Cys Ile Thr Leu Leu His Ala Arg Lys Arg Val
            405                 410                 415 gct ata caa ttc cta aag gac att cga gaa tct gtc act caa atc atg       1296
Ala Ile Gln Phe Leu Lys Asp Ile Arg Glu Ser Val Thr Gln Ile Met
        420                 425                 430 aag aat cct aaa gcg aag acc aca gga atg ggt gcc atc tat gcc atg       1344
Lys Asn Pro Lys Ala Lys Thr Thr Gly Met Gly Ala Ile Tyr Ala Met
    435                 440                 445 gcc cag aca act gtt gac agg aat atg gtt gca gaa ttg tcc tca gtc       1392
Ala Gln Thr Thr Val Asp Arg Asn Met Val Ala Glu Leu Ser Ser Val
450                 455                 460 ttc ttg gac agc ttg tac agc acc gac act gtc acc cag ggc agc cag       1440
Phe Leu Asp Ser Leu Tyr Ser Thr Asp Thr Val Thr Gln Gly Ser Gln
465                 470                 475                 480
```

```
atg aat ggt tct cca aaa ccc cac tga                                    1467
Met Asn Gly Ser Pro Lys Pro His *
                485
```

<210> SEQ ID NO 10
<211> LENGTH: 488
<212> TYPE: PRT
<213> ORGANISM: Homo sapiens

<400> SEQUENCE: 10

```
Met Pro Ser Thr Asp Leu Leu Met Leu Lys Ala Phe Glu Pro Tyr Leu
 1               5                  10                  15

Glu Ile Leu Glu Val Tyr Ser Thr Lys Ala Lys Asn Tyr Val Asn Gly
             20                  25                  30

His Cys Thr Lys Tyr Glu Pro Trp Gln Leu Ile Ala Trp Ser Val Val
         35                  40                  45

Trp Thr Leu Leu Ile Val Trp Gly Tyr Glu Phe Val Phe Gln Pro Glu
     50                  55                  60

Ser Leu Trp Ser Arg Phe Lys Lys Cys Phe Lys Leu Thr Arg Lys
 65                  70                  75                  80

Met Pro Ile Ile Gly Arg Lys Ile Gln Asp Lys Leu Asn Lys Thr Lys
                 85                  90                  95

Asp Asp Ile Ser Lys Asn Met Ser Phe Leu Lys Val Asp Lys Glu Tyr
            100                 105                 110

Val Lys Ala Leu Pro Ser Gln Gly Leu Ser Ser Ser Ala Val Leu Glu
        115                 120                 125

Lys Leu Lys Glu Tyr Ser Ser Met Asp Ala Phe Trp Gln Glu Gly Arg
    130                 135                 140

Ala Ser Gly Thr Val Tyr Ser Gly Glu Glu Lys Leu Thr Glu Leu Leu
145                 150                 155                 160

Val Lys Ala Tyr Gly Asp Phe Ala Trp Ser Asn Pro Leu His Pro Asp
                165                 170                 175

Ile Phe Pro Gly Leu Arg Lys Ile Glu Ala Glu Ile Val Arg Ile Ala
            180                 185                 190

Cys Ser Leu Phe Asn Gly Gly Pro Asp Ser Cys Gly Cys Val Thr Ser
        195                 200                 205

Gly Gly Thr Glu Ser Ile Leu Met Ala Cys Lys Ala Cys Arg Asp Leu
    210                 215                 220

Ala Phe Glu Lys Gly Ile Lys Thr Pro Glu Ile Val Ala Pro Gln Ser
225                 230                 235                 240

Ala His Ala Ala Phe Asn Lys Ala Ala Ser Tyr Phe Gly Met Lys Ile
                245                 250                 255

Val Arg Val Pro Leu Thr Lys Met Met Glu Val Asp Val Arg Ala Met
            260                 265                 270

Arg Arg Ala Ile Ser Arg Asn Thr Ala Met Leu Val Cys Ser Thr Pro
        275                 280                 285

Gln Phe Pro His Gly Val Ile Asp Pro Val Pro Glu Val Ala Lys Leu
    290                 295                 300

Ala Val Lys Tyr Lys Ile Pro Leu His Val Asp Ala Cys Leu Gly Gly
305                 310                 315                 320

Phe Leu Ile Val Phe Met Glu Lys Ala Gly Tyr Pro Leu Glu His Pro
                325                 330                 335

Phe Asp Phe Arg Val Lys Gly Val Thr Ser Ile Ser Ala Asp Thr His
            340                 345                 350

Lys Leu Glu Asn Ile Lys Gly Ile Phe Val Phe Gly Asn Pro Gln Leu
        355                 360                 365
```

Ser Leu Ile Ala Leu Gly Ser Arg Asp Phe Asp Ile Tyr Arg Leu Ser
    370                 375                 380

Asn Leu Met Thr Ala Lys Gly Trp Asn Leu Asn Gln Leu Gln Phe Pro
385                 390                 395                 400

Pro Ser Ile His Phe Cys Ile Thr Leu Leu His Ala Arg Lys Arg Val
                405                 410                 415

Ala Ile Gln Phe Leu Lys Asp Ile Arg Glu Ser Val Thr Gln Ile Met
            420                 425                 430

Lys Asn Pro Lys Ala Lys Thr Thr Gly Met Gly Ala Ile Tyr Ala Met
435                 440                 445

Ala Gln Thr Thr Val Asp Arg Asn Met Val Ala Glu Leu Ser Ser Val
    450                 455                 460

Phe Leu Asp Ser Leu Tyr Ser Thr Asp Thr Val Thr Gln Gly Ser Gln
465                 470                 475                 480

Met Asn Gly Ser Pro Lys Pro His
                485

<210> SEQ ID NO 11
<211> LENGTH: 552
<212> TYPE: PRT
<213> ORGANISM: C. elegans

<400> SEQUENCE: 11

Met Asp Ser Val Lys His Thr Thr Glu Ile Ile Val Asp Leu Thr Lys
1               5                   10                  15

Met His Tyr His Met Ile Asn Asp Arg Leu Ser Arg Tyr Asp Pro Val
            20                  25                  30

Val Leu Val Leu Ala Ala Phe Gly Gly Thr Leu Val Tyr Thr Lys Val
        35                  40                  45

Val His Leu Tyr Arg Lys Ser Glu Asp Pro Ile Leu Lys Arg Met Gly
    50                  55                  60

Ala Tyr Val Phe Ser Leu Leu Arg Lys Leu Pro Ala Val Arg Asp Lys
65                  70                  75                  80

Ile Glu Lys Glu Leu Ala Ala Glu Lys Pro Lys Leu Ile Glu Ser Ile
                85                  90                  95

His Lys Asp Asp Lys Asp Lys Gln Phe Ile Ser Thr Leu Pro Ile Ala
            100                 105                 110

Pro Leu Ser Gln Asp Ser Ile Met Glu Leu Ala Lys Lys Tyr Glu Asp
        115                 120                 125

Tyr Asn Thr Phe Asn Ile Asp Gly Gly Arg Val Ser Gly Ala Val Tyr
    130                 135                 140

Thr Asp Arg His Ala Glu His Ile Asn Leu Leu Gly Lys Ile Tyr Glu
145                 150                 155                 160

Lys Tyr Ala Phe Ser Asn Pro Leu His Pro Asp Val Phe Pro Gly Ala
                165                 170                 175

Arg Lys Met Glu Ala Glu Leu Ile Arg Met Val Leu Asn Leu Tyr Asn
            180                 185                 190

Gly Pro Glu Asp Ser Ser Gly Ser Val Thr Ser Gly Gly Thr Glu Ser
        195                 200                 205

Ile Ile Met Ala Cys Phe Ser Tyr Arg Asn Arg Ala His Ser Leu Gly
    210                 215                 220

Ile Glu His Pro Val Ile Leu Ala Cys Lys Thr Ala His Ala Ala Phe
225                 230                 235                 240

Asp Lys Ala Ala His Leu Cys Gly Met Arg Leu Arg His Val Pro Val
                245                 250                 255

Asp Ser Asp Asn Arg Val Asp Leu Lys Glu Met Glu Arg Leu Ile Asp
            260                 265                 270

Ser Asn Val Cys Met Leu Val Gly Ser Ala Pro Asn Phe Pro Ser Gly
        275                 280                 285

Thr Ile Asp Pro Ile Pro Glu Ile Ala Lys Leu Gly Lys Tyr Gly
        290                 295                 300

Ile Pro Val His Val Asp Ala Cys Leu Gly Gly Phe Met Ile Pro Phe
305                 310                 315                 320

Met Asn Asp Ala Gly Tyr Leu Ile Pro Val Phe Asp Phe Arg Asn Pro
                325                 330                 335

Gly Val Thr Ser Ile Ser Cys Asp Thr His Lys Tyr Gly Cys Thr Pro
            340                 345                 350

Lys Gly Ser Ser Ile Val Met Tyr Arg Ser Lys Glu Leu His His Phe
        355                 360                 365

Gln Tyr Phe Ser Val Ala Asp Trp Cys Gly Gly Ile Tyr Ala Thr Pro
    370                 375                 380

Thr Ile Ala Gly Ser Arg Ala Gly Ala Asn Thr Ala Val Ala Trp Ala
385                 390                 395                 400

Thr Leu Leu Ser Phe Gly Arg Asp Glu Tyr Val Arg Arg Cys Ala Gln
                405                 410                 415

Ile Val Lys His Thr Arg Met Leu Ala Glu Lys Ile Glu Lys Ile Lys
            420                 425                 430

Trp Ile Lys Pro Tyr Gly Lys Ser Asp Val Ser Leu Val Ala Phe Ser
        435                 440                 445

Gly Asn Gly Val Asn Ile Tyr Glu Val Ser Asp Lys Met Met Lys Leu
    450                 455                 460

Gly Trp Asn Leu Asn Thr Leu Gln Asn Pro Ala Ala Ile His Ile Cys
465                 470                 475                 480

Leu Thr Ile Asn Gln Ala Asn Glu Glu Val Val Asn Ala Phe Ala Val
                485                 490                 495

Asp Leu Glu Lys Ile Cys Glu Glu Leu Ala Ala Lys Gly Glu Gln Lys
            500                 505                 510

Ala Asp Ser Gly Met Ala Ala Met Tyr Gly Met Ala Ala Gln Val Pro
        515                 520                 525

Lys Ser Val Val Asp Glu Val Ile Ala Leu Tyr Ile Asp Ala Thr Tyr
    530                 535                 540

Ser Ala Pro Pro Ser Thr Ser Asn
545                 550

<210> SEQ ID NO 12
<211> LENGTH: 3162
<212> TYPE: DNA
<213> ORGANISM: C. elegans

<400> SEQUENCE: 12
atggattcgg ttaagcacac aaccgaaatt attgtcgact tgacaaaaat gcactatcac      60
atgataaatg ataggtgaat tttaaacaaa aattagatat ttggaaatta ctaattcaag     120
attttcagac tttctcggta tgatccggtt gttctagtgt tggccgcttt tgggggtacc     180
cttgtctata caaagtcgt ccatttgtac cgaaaaagcg aggatccaat tttgaaacgg      240
caagtgtttt cttgcgaatt ttagaaatat caaaatgaaa ttttcagcat gggagcttat     300
gtattctcac ttcttcgaaa acttccagct gttcgggata aaatcgaaaa agagctggct     360
gctgagaagc caaagcttat tgaatcgatt cataaggatg ataaggacaa gcaattcatt     420

```
tccagtttgt ttgaacattt attaattaac caattcatta attctatttt tcagctcttc    480
ccatcgctcc attatctcag gactcaatta tggaactggc gaaaaaatat gaggattaca    540
acacatttaa cattgacgga ggacgagtat ctggagcggt ttatactgat cgtcatgctg    600
aacacattaa tttgcttgga aaggtttaga aattctagaa tttttcaaaa tcttagctct    660
caaatatatt ctcttgtaaa tagctacata gtatatcctg tagggaagct tgaatccaa     720
ttcagatcag gggcgacaaa cgattttttc cggcaaatcg gcaaatcgcc ggaatggaaa    780
tttcctgcaa atcggcaaat tgccggaatg gaaatttcct gcaagttggc aaattgacgg    840
aattgaaatt tccggcaaac cgacaaattt ccgtaattaa aatttcctgc aaaccggcga    900
attggcggaa ttgaaatttc ctgcaaaccg gcaaattgcc gtaattgaaa tttcctgcaa    960
accggcaaat tgccggaatt gaaatttccg gcaaaccggc aaatcggctg aattgaaatt   1020
tcctgcaaac cggcaaattg cggtaattga aattcctgc aaaccggtca gttgccgatt    1080
tgcctttgcc tgaaaacgg cgattgccag aaatattcgg caaattgtgg ttttgcacat    1140
ttttctggaa atttcaggca aaattgtacg catcctatga atatccctat aacatcttt    1200
tttgaaaagt cagtaaatta tatgaaaata tctaaagaaa cggggaaaa tatttcaaag    1260
aggcacagtt ttatgtgttt ccgtcatcta aatagtccct ctaaacattt ccggcaaatc   1320
tgatatccgg caaacggcaa atcgggatat tgccggaatt taaaatttgc gaacttgtc    1380
gacaaaaaaa atgcgccttg aatccgattc agatattcaa aaattgaatt ttggacgttt   1440
tagaaatcat ttagtttgtc aattttcaag aaatttctag aaaattggat ggtttccgcc   1500
aagaaatatt agctacatga aaataatttt gaaactagac atttcttaaa ataaaaattg   1560
ccatctttta tatccagatt tacgaaaagt atgcgttctc gaatcccctc caccctgacg   1620
tctttccggg agctcgtaaa atggaggcag aacttattcg aatggttctg aacctgtata   1680
atggaccaga agattctagt ggaagtgtaa cttctggtgg tactgaaagt attattatgg   1740
catgcttttc gtatcggtaa gcatttattc aactcttaaa attcaatttt gcaaactcta   1800
cagaaatcgt gcacactctc ttggcattga acatccagtt attttggcat gtaaaacagc   1860
tcacgcggca tttgataagg ccgcccatct atgcggaatg cgtcttcgcc acgttccagt   1920
tgattcggat aatcgtgtcg atttaaaaga aatggagaga ctaattgatt cgaatgtttg   1980
tatgttggtt ggctcagcgc ctaacttccc atcaggcaca attgatccaa ttccggaaat   2040
tgctaaggta ctggaaattc ccgcctcaat atcgcggaaa aaatagagaa atgactgaac   2100
aaaattacat tgtgagcggg aactctaatt gaattcagca aaaatacgat actttttct    2160
aacttaaaat aattttaaa aaaactcaca gatgctagtc caaaaaatgg ccttttttga    2220
ttacttaatc gaacgtttac actttcagct cggcaaaaag tatggaatcc cggtccacgt   2280
ggacgcatgt cttggtggat tcatgattcc atttatgaat gacgccggat acctgattcc   2340
tgtattcgat ttcagaaatc ccggtgttac atctatttcg tgtgatactc ataaggttgg   2400
atacagttct atccattttt ttccttcaat tcaaaatctt tcagtacgga tgcacaccga   2460
aaggttcatc gattgtcatg tatcgttcca aggaacttca tcacttccag tatttctcgg   2520
ttgccgattg gtgtggaggc atctatgcca ccccgactat tgcaggtttg aagaatgttt   2580
tagtagcttc aatagaatca aagagatccc ttaggatccc gagctggagc caacactgcc   2640
gtcgcctggg ccacacttt atccttcggt cgagacgaat atgttcgaag atgtgctcaa    2700
attgtgaagc atacacgaat gctggccgag aaaattgaga aaatcaaatg gatcaagcct   2760
tatggaaaat cggatgtttc attggtggcg ttctccggaa atggtgtgaa tatctacgaa   2820
```

| | |
|---|---|
| gtttctgaca aaatgatgaa gctcggatgg aatttgaaca ctctgcagaa tccagcggcg | 2880 |
| tatgtttatc aattttatga gttatcagct tgctaaattt tttgtttcag aatccacatt | 2940 |
| tgtttgacaa tcaatcaagc gaacgaggaa gttgtgaatg cgttcgccgt cgaccttgag | 3000 |
| aagatttgtg aagaactcgc tgcaaaaggt gaacaaaaag ctgacagtgg aatggctgcg | 3060 |
| atgtatggaa tggctgcgca agtaccaaaa tcagtagtgg acgaggttat cgctctgtac | 3120 |
| attgacgcaa cttattcagc tccaccttca acttctaatt aa | 3162 |

```
<210> SEQ ID NO 13
<211> LENGTH: 34
<212> TYPE: DNA
<213> ORGANISM: Artificial Sequence
<220> FEATURE:
<223> OTHER INFORMATION: primer

<400> SEQUENCE: 13
```

| | |
|---|---|
| gaggaattca tggattcggt taagcacaca accg | 34 |

```
<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
```

| | |
|---|---|
| agcctcgagt taattagaag ttgaaggtgg agc | 33 |

```
<210> SEQ ID NO 15
<211> LENGTH: 1638
<212> TYPE: DNA
<213> ORGANISM: Drosophila melanogaster

<400> SEQUENCE: 15
```

| | |
|---|---|
| atgcgtccgt tctccggcag cgattgcctt aagcccgtca ccgagggcat caaccgggcg | 60 |
| ttcggcgcca aggagccctg gcaggtggcc accatcacgg ccaccacggt gctgggaggc | 120 |
| gtctggctct ggactgtgat ctgccaggat gaaaatcttt acattcgtgg caagcgtcag | 180 |
| ttctttaagt ttgccaagaa gattccagcc gtgcgtcgtc aggtggagac tgaattggcc | 240 |
| aaggccaaaa acgacttcga gacggaaatc aaaaagagca acgcccacct tacctactcg | 300 |
| gaaactctgc ccgagaaggg actcagcaag gaggagatcc tccgactggt ggatgagcac | 360 |
| ctgaagactg tcactacaa ctggcgtgat ggtcgtgtat ctggcgcggt ctacggctac | 420 |
| aagcctgatc tggtggagct cgtcactgaa gtgtacggca aggcctccta caccaatccc | 480 |
| ttgcacgcag atcttttccc gggagtttgc aaaatggagg cggaggtagt gcgcatggca | 540 |
| tgcaacctgt tccatggaaa ctcagccagc tgtggaacca tgaccaccgg cggcaccgaa | 600 |
| tccattgtaa tggccatgaa ggcgtacagg gatttcgcta gagagtacaa gggaatcacc | 660 |
| aggccaaaca tcgtggtgcc taagacggtc cacgcggcct tcgacaaggg cggtcagtac | 720 |
| tttaatatcc acgtgcgatc cgtggatgta gatccggaga cctacgaagt ggacattaag | 780 |
| aagttcaaac gtgccattaa caggaacacg attctgctgg ttgggtctgc tccgaacttc | 840 |
| ccctatggaa ccatcgatga catcgaagct atcgccgctt gggcgttaa gtacgacatt | 900 |
| cccgtgcacg tggacgcctg cctgggcagc tttgtggtgg ccttggtccg caacgccggc | 960 |
| tataagctgc gtcccttcga ctttgaggtc aagggagtga ccagtatctc cgctgatacc | 1020 |
| cacaagtatg gtttcgcgcc caagggatca tcggtgatcc tttactcgga caagaagtac | 1080 |

-continued

```
aaggaccatc agttcactgt gactactgac tggcctggcg gcgtgtatgg ttctcccaca    1140
gtcaacggtt cccgtgccgg aggtattatc gccgcctgct gggctaccat gatgagcttt    1200
ggctatgatg ttatctgga  agccactaag cgcattgtgg atacggcgcg ctatatcgag    1260
aggggcgttc gcgacatcga tggcatcttt atctttggca agccagctac ttcagtgatt    1320
gccctgggtt ccaatgtgtt tgacattttc cggctatcgg attcgctgtg caaactgggc    1380
tggaacctaa atgcgctgca gtttccatct ggtatccacc tgtgcgtgac ggacatgcac    1440
acacagcccg gagtcgcgga taaattcatt gccgatgtgc gcagctgtac ggcggagatc    1500
atgaaggatc ccggccagcc cgtcgttgga agatggctc  tttacggcat ggcacagagc    1560 ataccccgacc gttcggtgat cggagaagtg actcgcctat tcctgcactc catgtactac    1620
actcccagcc agaaatag                                                    1638
```

<210> SEQ ID NO 16
<211> LENGTH: 545
<212> TYPE: PRT
<213> ORGANISM: Drosophila melanogaster

<400> SEQUENCE: 16

```
Met Arg Pro Phe Ser Gly Ser Asp Cys Leu Lys Pro Val Thr Glu Gly
  1               5                  10                  15

Ile Asn Arg Ala Phe Gly Ala Lys Glu Pro Trp Gln Val Ala Thr Ile
             20                  25                  30

Thr Ala Thr Thr Val Leu Gly Gly Val Trp Leu Trp Thr Val Ile Cys
         35                  40                  45

Gln Asp Glu Asn Leu Tyr Ile Arg Gly Lys Arg Gln Phe Phe Lys Phe
     50                  55                  60

Ala Lys Lys Ile Pro Ala Val Arg Arg Gln Val Glu Thr Glu Leu Ala
 65                  70                  75                  80

Lys Ala Lys Asn Asp Phe Glu Thr Glu Ile Lys Lys Ser Asn Ala His
                 85                  90                  95

Leu Thr Tyr Ser Glu Thr Leu Pro Glu Lys Gly Leu Ser Lys Glu Glu
            100                 105                 110

Ile Leu Arg Leu Val Asp Glu His Leu Lys Thr Gly His Tyr Asn Trp
        115                 120                 125

Arg Asp Gly Arg Val Ser Gly Ala Val Tyr Gly Tyr Lys Pro Asp Leu
    130                 135                 140

Val Glu Leu Val Thr Glu Val Tyr Gly Lys Ala Ser Tyr Thr Asn Pro
145                 150                 155                 160

Leu His Ala Asp Leu Phe Pro Gly Val Cys Lys Met Glu Ala Glu Val
                165                 170                 175

Val Arg Met Ala Cys Asn Leu Phe His Gly Asn Ser Ala Ser Cys Gly
            180                 185                 190

Thr Met Thr Thr Gly Gly Thr Glu Ser Ile Val Met Ala Met Lys Ala
        195                 200                 205

Tyr Arg Asp Phe Ala Arg Glu Tyr Lys Gly Ile Thr Arg Pro Asn Ile
    210                 215                 220

Val Val Pro Lys Thr Val His Ala Ala Phe Asp Lys Gly Gly Gln Tyr
225                 230                 235                 240

Phe Asn Ile His Val Arg Ser Val Asp Val Pro Glu Thr Tyr Glu
                245                 250                 255

Val Asp Ile Lys Lys Phe Lys Arg Ala Ile Asn Arg Asn Thr Ile Leu
            260                 265                 270

Leu Val Gly Ser Ala Pro Asn Phe Pro Tyr Gly Thr Ile Asp Asp Ile
```

```
              275                 280                 285
Glu Ala Ile Ala Ala Leu Gly Val Lys Tyr Asp Ile Pro Val His Val
    290                 295                 300

Asp Ala Cys Leu Gly Ser Phe Val Val Ala Leu Val Arg Asn Ala Gly
305                 310                 315                 320

Tyr Lys Leu Arg Pro Phe Asp Phe Glu Val Lys Gly Val Thr Ser Ile
                325                 330                 335

Ser Ala Asp Thr His Lys Tyr Gly Phe Ala Pro Lys Gly Ser Ser Val
            340                 345                 350

Ile Leu Tyr Ser Asp Lys Lys Tyr Lys Asp His Gln Phe Thr Val Thr
        355                 360                 365

Thr Asp Trp Pro Gly Gly Val Tyr Gly Ser Pro Thr Val Asn Gly Ser
    370                 375                 380

Arg Ala Gly Gly Ile Ile Ala Ala Cys Trp Ala Thr Met Met Ser Phe
385                 390                 395                 400

Gly Tyr Asp Gly Tyr Leu Glu Ala Thr Lys Arg Ile Val Asp Thr Ala
                405                 410                 415

Arg Tyr Ile Glu Arg Gly Val Arg Asp Ile Asp Gly Ile Phe Ile Phe
            420                 425                 430

Gly Lys Pro Ala Thr Ser Val Ile Ala Leu Gly Ser Asn Val Phe Asp
        435                 440                 445

Ile Phe Arg Leu Ser Asp Ser Leu Cys Lys Leu Gly Trp Asn Leu Asn
    450                 455                 460

Ala Leu Gln Phe Pro Ser Gly Ile His Leu Cys Val Thr Asp Met His
465                 470                 475                 480

Thr Gln Pro Gly Val Ala Asp Lys Phe Ile Ala Asp Val Arg Ser Cys
                485                 490                 495

Thr Ala Glu Ile Met Lys Asp Pro Gly Gln Pro Val Val Gly Lys Met
            500                 505                 510

Ala Leu Tyr Gly Met Ala Gln Ser Ile Pro Asp Arg Ser Val Ile Gly
        515                 520                 525

Glu Val Thr Arg Leu Phe Leu His Ser Met Tyr Tyr Thr Pro Ser Gln
    530                 535                 540

Lys
545

<210> SEQ ID NO 17
<211> LENGTH: 1707
<212> TYPE: DNA
<213> ORGANISM: Homo sapiens
<220> FEATURE:
<221> NAME/KEY: CDS
<222> LOCATION: (1)...(1707)

<400> SEQUENCE: 17 atg cct agc aca gac ctt ctg atg ttg aag gcc ttt gag ccc tac tta      48
Met Pro Ser Thr Asp Leu Leu Met Leu Lys Ala Phe Glu Pro Tyr Leu
1               5                   10                  15 gag att ttg gaa gta tac tcc aca aaa gcc aag aat tat gta aat gga      96
Glu Ile Leu Glu Val Tyr Ser Thr Lys Ala Lys Asn Tyr Val Asn Gly
            20                  25                  30 cat tgc acc aag tat gag ccc tgg cag cta att gca tgg agt gtc gtg     144
His Cys Thr Lys Tyr Glu Pro Trp Gln Leu Ile Ala Trp Ser Val Val
        35                  40                  45 tgg acc ctg ctg ata gtc tgg gga tat gag ttt gtc ttc cag cca gag     192
Trp Thr Leu Leu Ile Val Trp Gly Tyr Glu Phe Val Phe Gln Pro Glu
    50                  55                  60
```

```
agt tta tgg tca agg ttt aaa aag aaa tgt ttt aag ctc acc agg aag      240
Ser Leu Trp Ser Arg Phe Lys Lys Lys Cys Phe Lys Leu Thr Arg Lys
65              70                  75                  80 atg ccc att att ggt cgt aag att caa gac aag ttg aac aag acc aag      288
Met Pro Ile Ile Gly Arg Lys Ile Gln Asp Lys Leu Asn Lys Thr Lys
                    85                  90                  95 gat gat att agc aag aac atg tca ttc ctg aaa gtg gac aaa gag tat      336
Asp Asp Ile Ser Lys Asn Met Ser Phe Leu Lys Val Asp Lys Glu Tyr
                100                 105                 110 gtg aaa gct tta ccc tcc cag ggt ctg agc tca tct gct gtt ttg gag      384
Val Lys Ala Leu Pro Ser Gln Gly Leu Ser Ser Ser Ala Val Leu Glu
            115                 120                 125 aaa ctt aag gag tac agc tct atg gac gcc ttc tgg caa gag ggg aga      432
Lys Leu Lys Glu Tyr Ser Ser Met Asp Ala Phe Trp Gln Glu Gly Arg
130                 135                 140 gcc tct gga aca gtg tac agt ggg gag gag aag ctc act gag ctc ctt      480
Ala Ser Gly Thr Val Tyr Ser Gly Glu Glu Lys Leu Thr Glu Leu Leu
145                 150                 155                 160 gtg aag gct tat gga gat ttt gca tgg agt aac ccc ctg cat cca gat      528
Val Lys Ala Tyr Gly Asp Phe Ala Trp Ser Asn Pro Leu His Pro Asp
                165                 170                 175 atc ttc cca gga cta cgc aag ata gag gca gaa att gtg agg ata gct      576
Ile Phe Pro Gly Leu Arg Lys Ile Glu Ala Glu Ile Val Arg Ile Ala
                180                 185                 190 tgt tcc ctg ttc aat ggg gga cca gat tcg tgt gga tgt gtg act tct      624
Cys Ser Leu Phe Asn Gly Gly Pro Asp Ser Cys Gly Cys Val Thr Ser
            195                 200                 205 ggg gga aca gaa agc ata ctc atg gcc tgc aaa gca tat cgg gat ctg      672
Gly Gly Thr Glu Ser Ile Leu Met Ala Cys Lys Ala Tyr Arg Asp Leu
210                 215                 220 gcc ttt gag aag ggg atc aaa act cca gaa att gtg gct ccc caa agt      720
Ala Phe Glu Lys Gly Ile Lys Thr Pro Glu Ile Val Ala Pro Gln Ser
225                 230                 235                 240 gcc cat gct gca ttt aac aaa gca gcc agt tac ttt ggg atg aag att      768
Ala His Ala Ala Phe Asn Lys Ala Ala Ser Tyr Phe Gly Met Lys Ile
                245                 250                 255 gtg cgg gtc cca ttg acg aag atg atg gag gtg gat gtg agg gca atg      816
Val Arg Val Pro Leu Thr Lys Met Met Glu Val Asp Val Arg Ala Met
                260                 265                 270 aga aga gct atc tcc agg aac act gcc atg ctc gtc tgt tct acc cca      864
Arg Arg Ala Ile Ser Arg Asn Thr Ala Met Leu Val Cys Ser Thr Pro
            275                 280                 285 cag ttt cct cat ggt gta ata gat cct gtc cct gaa gtg gcc aag ctg      912
Gln Phe Pro His Gly Val Ile Asp Pro Val Pro Glu Val Ala Lys Leu
290                 295                 300 gct gtc aaa tac aaa ata ccc ctt cat gtc gac gct tgt ctg gga ggc      960
Ala Val Lys Tyr Lys Ile Pro Leu His Val Asp Ala Cys Leu Gly Gly
305                 310                 315                 320 ttc ctc atc gtc ttt atg gag aaa gca gga tac cca ctg gag cac cca     1008
Phe Leu Ile Val Phe Met Glu Lys Ala Gly Tyr Pro Leu Glu His Pro
                325                 330                 335 ttt gat ttc cgg gtg aaa ggt gta acc agc att tca gct gac acc cat     1056
Phe Asp Phe Arg Val Lys Gly Val Thr Ser Ile Ser Ala Asp Thr His
                340                 345                 350 aag tat ggc tat gcc cca aaa ggc tca tca ttg gtg ttg tat agt gac     1104
Lys Tyr Gly Tyr Ala Pro Lys Gly Ser Ser Leu Val Leu Tyr Ser Asp
            355                 360                 365 aag aag tac agg aac tat cag ttc ttc gtc gat aca gat tgg cag ggt     1152
Lys Lys Tyr Arg Asn Tyr Gln Phe Phe Val Asp Thr Asp Trp Gln Gly
370                 375                 380
```

```
ggc atc tat gct tcc cca acc atc gca ggc tca cgg cct ggt ggc att    1200
Gly Ile Tyr Ala Ser Pro Thr Ile Ala Gly Ser Arg Pro Gly Gly Ile
385             390                 395                 400 agc gca gcc tgt tgg gct gcc ttg atg cac ttc ggt gag aac ggc tat    1248
Ser Ala Ala Cys Trp Ala Ala Leu Met His Phe Gly Glu Asn Gly Tyr
            405                 410                 415 gtt gaa gct acc aaa cag atc atc aaa act gct cgc ttc ctc aag tca    1296
Val Glu Ala Thr Lys Gln Ile Ile Lys Thr Ala Arg Phe Leu Lys Ser
        420                 425                 430 gaa ctg gaa aat atc aaa ggc atc ttt gtt ttt ggg aat ccc caa ttg    1344
Glu Leu Glu Asn Ile Lys Gly Ile Phe Val Phe Gly Asn Pro Gln Leu
                435                 440                 445 tca gtc att gct ctg gga tcc cgt gat ttt gac atc tac cga cta tca    1392
Ser Val Ile Ala Leu Gly Ser Arg Asp Phe Asp Ile Tyr Arg Leu Ser
    450                 455                 460 aac ctg atg act gct aag ggg tgg aac ttg aac cag ttg cag ttc cca    1440
Asn Leu Met Thr Ala Lys Gly Trp Asn Leu Asn Gln Leu Gln Phe Pro
465                 470                 475                 480 ccc agt att cat ttc tgc atc aca tta cta cac gcc cgg aaa cga gta    1488
Pro Ser Ile His Phe Cys Ile Thr Leu Leu His Ala Arg Lys Arg Val
            485                 490                 495 gct ata caa ttc cta aag gac att cga gaa tct gtc act caa atc atg    1536
Ala Ile Gln Phe Leu Lys Asp Ile Arg Glu Ser Val Thr Gln Ile Met
        500                 505                 510 aag aat cct aaa gcg aag acc aca gga atg ggt gcc atc tat ggc atg    1584
Lys Asn Pro Lys Ala Lys Thr Thr Gly Met Gly Ala Ile Tyr Gly Met
                515                 520                 525 gcc cag aca act gtt gac agg aat atg gtt gca gaa ttg tcc tca gtc    1632
Ala Gln Thr Thr Val Asp Arg Asn Met Val Ala Glu Leu Ser Ser Val
    530                 535                 540 ttc ttg gac agc ttg tac agc acc gac act gtc acc cag ggc agc cag    1680
Phe Leu Asp Ser Leu Tyr Ser Thr Asp Thr Val Thr Gln Gly Ser Gln
545                 550                 555                 560 atg aat ggt tct cca aaa ccc cac tga                                1707
Met Asn Gly Ser Pro Lys Pro His *
            565

<210> SEQ ID NO 18
<211> LENGTH: 568
<212> TYPE: PRT
<213> ORGANISM: Homo sapiens

<400> SEQUENCE: 18

Met Pro Ser Thr Asp Leu Leu Met Leu Lys Ala Phe Glu Pro Tyr Leu
1               5                   10                  15

Glu Ile Leu Glu Val Tyr Ser Thr Lys Ala Lys Asn Tyr Val Asn Gly
            20                  25                  30

His Cys Thr Lys Tyr Glu Pro Trp Gln Leu Ile Ala Trp Ser Val Val
        35                  40                  45

Trp Thr Leu Leu Ile Val Trp Gly Tyr Glu Phe Val Phe Gln Pro Glu
    50                  55                  60

Ser Leu Trp Ser Arg Phe Lys Lys Cys Phe Lys Leu Thr Arg Lys
65                  70                  75                  80

Met Pro Ile Ile Gly Arg Lys Ile Gln Asp Lys Leu Asn Lys Thr Lys
                85                  90                  95

Asp Asp Ile Ser Lys Asn Met Ser Phe Leu Lys Val Asp Lys Glu Tyr
            100                 105                 110

Val Lys Ala Leu Pro Ser Gln Gly Leu Ser Ser Ser Ala Val Leu Glu
        115                 120                 125
```

```
Lys Leu Lys Glu Tyr Ser Ser Met Asp Ala Phe Trp Gln Glu Gly Arg
        130                 135                 140

Ala Ser Gly Thr Val Tyr Ser Gly Glu Glu Lys Leu Thr Glu Leu Leu
145                 150                 155                 160

Val Lys Ala Tyr Gly Asp Phe Ala Trp Ser Asn Pro Leu His Pro Asp
                165                 170                 175

Ile Phe Pro Gly Leu Arg Lys Ile Glu Ala Glu Ile Val Arg Ile Ala
            180                 185                 190

Cys Ser Leu Phe Asn Gly Gly Pro Asp Ser Cys Gly Cys Val Thr Ser
        195                 200                 205

Gly Gly Thr Glu Ser Ile Leu Met Ala Cys Lys Ala Tyr Arg Asp Leu
210                 215                 220

Ala Phe Glu Lys Gly Ile Lys Thr Pro Glu Ile Val Ala Pro Gln Ser
225                 230                 235                 240

Ala His Ala Ala Phe Asn Lys Ala Ala Ser Tyr Phe Gly Met Lys Ile
                245                 250                 255

Val Arg Val Pro Leu Thr Lys Met Met Glu Val Asp Val Arg Ala Met
            260                 265                 270

Arg Arg Ala Ile Ser Arg Asn Thr Ala Met Leu Val Cys Ser Thr Pro
        275                 280                 285

Gln Phe Pro His Gly Val Ile Asp Pro Val Pro Glu Val Ala Lys Leu
290                 295                 300

Ala Val Lys Tyr Lys Ile Pro Leu His Val Asp Ala Cys Leu Gly Gly
305                 310                 315                 320

Phe Leu Ile Val Phe Met Glu Lys Ala Gly Tyr Pro Leu Glu His Pro
                325                 330                 335

Phe Asp Phe Arg Val Lys Gly Val Thr Ser Ile Ser Ala Asp Thr His
            340                 345                 350

Lys Tyr Gly Tyr Ala Pro Lys Gly Ser Ser Leu Val Leu Tyr Ser Asp
        355                 360                 365

Lys Lys Tyr Arg Asn Tyr Gln Phe Phe Val Asp Thr Asp Trp Gln Gly
370                 375                 380

Gly Ile Tyr Ala Ser Pro Thr Ile Ala Gly Ser Arg Pro Gly Gly Ile
385                 390                 395                 400

Ser Ala Ala Cys Trp Ala Ala Leu Met His Phe Gly Glu Asn Gly Tyr
                405                 410                 415

Val Glu Ala Thr Lys Gln Ile Ile Lys Thr Ala Arg Phe Leu Lys Ser
            420                 425                 430

Glu Leu Glu Asn Ile Lys Gly Ile Phe Val Phe Gly Asn Pro Gln Leu
        435                 440                 445

Ser Val Ile Ala Leu Gly Ser Arg Asp Phe Asp Ile Tyr Arg Leu Ser
450                 455                 460

Asn Leu Met Thr Ala Lys Gly Trp Asn Leu Asn Gln Leu Gln Phe Pro
465                 470                 475                 480

Pro Ser Ile His Phe Cys Ile Thr Leu Leu His Ala Arg Lys Arg Val
                485                 490                 495

Ala Ile Gln Phe Leu Lys Asp Ile Arg Glu Ser Val Thr Gln Ile Met
            500                 505                 510

Lys Asn Pro Lys Ala Lys Thr Thr Gly Met Gly Ala Ile Tyr Gly Met
        515                 520                 525

Ala Gln Thr Thr Val Asp Arg Asn Met Val Ala Glu Leu Ser Ser Val
530                 535                 540

Phe Leu Asp Ser Leu Tyr Ser Thr Asp Thr Val Thr Gln Gly Ser Gln
545                 550                 555                 560
```

```
Met Asn Gly Ser Pro Lys Pro His
                565

<210> SEQ ID NO 19
<211> LENGTH: 490
<212> TYPE: PRT
<213> ORGANISM: Drosophila melanogaster

<400> SEQUENCE: 19

Phe Arg Ser Ser Asn Asp Tyr Gly Val Asn Leu Gln Thr Ala Glu Met
 1               5                  10                  15

Trp His His Thr Ile Arg Lys His Lys Arg Gly Asn Gly Ser Ser Ser
            20                  25                  30

Pro Ala Asp Cys Gly Lys Gln Leu Leu Ile Leu Leu Asn Pro Lys Ser
        35                  40                  45

Gly Ser Gly Lys Gly Arg Glu Leu Phe Gln Lys Gln Val Ala Pro Leu
    50                  55                  60

Leu Thr Glu Ala Glu Val Gln Tyr Asp Leu Gln Ile Thr Thr His Pro
65                  70                  75                  80

Gln Tyr Ala Lys Glu Phe Val Arg Thr Arg Arg Asp Leu Leu Thr Arg
                85                  90                  95

Tyr Ser Gly Ile Val Val Ala Ser Gly Asp Gly Leu Phe Tyr Glu Val
            100                 105                 110

Leu Asn Gly Leu Met Glu Arg Met Asp Trp Arg Arg Ala Cys Arg Glu
        115                 120                 125

Leu Pro Leu Gly Ile Ile Pro Cys Gly Ser Gly Asn Gly Leu Ala Lys
    130                 135                 140

Ser Val Ala His His Cys Asn Glu Pro Tyr Glu Pro Lys Pro Ile Leu
145                 150                 155                 160

His Ala Thr Leu Thr Cys Met Ala Gly Lys Ser Thr Pro Met Asp Val
                165                 170                 175

Val Arg Val Glu Leu Ala Thr Arg Asp Lys His Phe Val Met Tyr Ser
            180                 185                 190

Phe Leu Ser Val Gly Trp Gly Leu Ile Ala Asp Ile Asp Ile Glu Ser
        195                 200                 205

Glu Arg Leu Arg Ser Ile Gly Ala Gln Arg Phe Thr Leu Trp Ala Ile
    210                 215                 220

Lys Arg Leu Ile Gly Leu Arg Ser Tyr Lys Gly Arg Val Ser Tyr Leu
225                 230                 235                 240

Leu Gly Lys Gly Lys Lys Glu Pro Pro Val Glu Ala Ala Arg Glu Leu
                245                 250                 255

Pro Ala Glu Ser Thr Ala Ala Gly Ile Arg Ser Ser Leu Pro Leu Asn
            260                 265                 270

Ala Gly Glu Phe His Asp Leu Pro Glu Glu Glu Gly Glu Ala Val
        275                 280                 285

Leu Asp Gly Glu Gln Phe Ala Asp Ala Ile Ser Leu Asp Arg Ser Val
    290                 295                 300

Tyr Arg Gln His Ala Asp Ser Trp His Ser Ala Met Ser Arg Arg Thr
305                 310                 315                 320

Ala Tyr Tyr Ser Leu Gly Gly Pro Ser Met Arg Ser Asn Arg Ser Arg
                325                 330                 335

Met Ser Ile Ser Gln Arg Ile Glu Ala Ala Asn Ala Glu Phe Ala Glu
            340                 345                 350

Arg Val Pro Thr Gly Thr Ile Pro Pro Leu Gln Met Pro Leu Leu Ser
        355                 360                 365
```

```
Ser Asp Gly Trp Ile Cys Glu Asp Gly Asp Phe Val Met Val His Ala
    370                 375                 380

Ala Tyr Thr Thr His Leu Ser Ser Asp Val Phe Phe Ala Pro Glu Ser
385                 390                 395                 400

Arg Leu Asp Asp Gly Leu Ile Tyr Leu Val Ile Ile Arg Arg Gly Val
                405                 410                 415

Ser Arg His Gln Leu Leu Asn Phe Met Leu Asn Leu Asn Ala Gly Thr
                420                 425                 430

His Leu Pro Ile Gly Glu Asp Pro Phe Ile Lys Val Val Pro Cys Arg
                435                 440                 445

Ala Phe Arg Ile Glu Pro Ser Ser Asp Gly Ile Leu Val Val Asp
450                 455                 460

Gly Glu Arg Val Glu Tyr Gly Pro Ile Gln Ala Glu Val Met Pro Gly
465                 470                 475                 480

Leu Ile Asn Val Met Thr Thr Ser Gly Gln
                485                 490

<210> SEQ ID NO 20
<211> LENGTH: 524
<212> TYPE: PRT
<213> ORGANISM: Drosophila melanogaster

<400> SEQUENCE: 20

Phe Arg Ser Phe Asp Thr Phe Glu Asp Asn Met Arg Glu Ala Asp Arg
1               5                   10                  15

Trp Tyr Arg Ser Leu Arg Trp Gln Leu His Arg Thr Leu Glu Glu Ile
                20                  25                  30

Phe Val Ala Pro Thr Val Asp Glu Arg Arg Arg Val Leu Val Leu
            35                  40                  45

Leu Asn Pro Lys Ser Gly Ser Gly Asp Ala Arg Glu Val Phe Asn Met
50                  55                  60

His Val Thr Pro Val Leu Asn Glu Ala Glu Val Pro Tyr Asp Leu Tyr
65                  70                  75                  80

Val Thr Lys His Ser Asn Phe Ala Ile Glu Phe Leu Ser Thr Arg Cys
                85                  90                  95

Leu Asp Ala Trp Cys Cys Val Ala Val Gly Gly Asp Gly Leu Phe
                100                 105                 110

His Glu Ile Val Asn Gly Leu Leu Gln Arg Gln Asp Trp Ala His Val
            115                 120                 125

Leu Pro His Leu Ala Leu Gly Ile Ile Pro Cys Gly Ser Gly Asn Gly
130                 135                 140

Leu Ala Arg Ser Ile Ala His Cys Tyr Asn Lys Pro Val Leu Gly Ala
145                 150                 155                 160

Ala Leu Thr Val Ile Ser Gly Arg Ser Pro Met Asp Val Val Arg
                165                 170                 175

Val Gln Leu Gln Ser Arg Ser Leu Tyr Ser Phe Leu Ser Ile Gly Trp
            180                 185                 190

Gly Leu Ile Ser Asp Val Asp Ile Glu Ser Glu Arg Ile Arg Met Leu
            195                 200                 205

Gly Tyr Gln Arg Phe Thr Val Trp Thr Leu Tyr Arg Leu Val Asn Leu
        210                 215                 220

Arg Thr Tyr Asn Gly Arg Ile Ser Tyr Leu Leu Thr Asp His Glu Val
225                 230                 235                 240

Ser Ser Thr His Ser Ala Thr Gly Tyr Ala Ala Gln Arg Arg Met Gln
                245                 250                 255
```

Ser Ser Arg Ser Cys Asn Thr His Ile Asp Met Leu Asn Gly Pro Ala
            260                 265                 270

Pro Ile Tyr His Ser Ser Ala Glu Tyr Leu Pro Gln Glu Phe Ala Asp
        275                 280                 285

Val Ile Ser Leu Glu Thr Ser Ile Asn Gln Ser Phe Arg Ser Arg Cys
    290                 295                 300

Asp Ser Trp Leu Ser Gly Gly Ser Arg Arg Ser Phe Tyr Tyr Ser Ile
305                 310                 315                 320

Ser Glu Ser Ile Tyr His Ser Leu Ala Asp Glu Ser Glu Phe Ala Gly
                325                 330                 335

Leu Ala Ala Ala Ser Leu Glu Asn Arg Gln Gln Asn Tyr Gly Pro Ala
            340                 345                 350

Ser Glu Leu Pro Asp Leu Asn Glu Pro Leu Ser Glu Asp Gln Gly Trp
        355                 360                 365

Leu Val Glu Glu Gly Glu Phe Val Met Met His Ala Val Tyr Gln Thr
    370                 375                 380

His Leu Gly Ile Asp Cys His Phe Ala Pro Lys Ala Gln Leu Asn Asp
385                 390                 395                 400

Gly Thr Ile Tyr Leu Ile Leu Ile Arg Ala Gly Ile Ser Arg Pro His
                405                 410                 415

Leu Leu Ser Phe Leu Tyr Asn Met Ser Ser Gly Thr His Leu Pro Glu
            420                 425                 430

Ser His Asp Asp His Val Lys Val Leu Pro Val Arg Ala Phe Arg Leu
        435                 440                 445

Glu Pro Tyr Asp Asn His Gly Ile Ile Thr Val Asp Gly Glu Arg Val
    450                 455                 460

Glu Phe Gly Pro Leu Gln Ala Glu Val Leu Pro Gly Ile Ala Arg Val
465                 470                 475                 480

Met Val Pro Asn Val Ser Thr Phe Arg Phe Gln Ser Ala Thr Leu Gln
                485                 490                 495

His Gly Ile Pro Val Cys Ile Pro Val Arg Lys Arg Phe Val Leu Tyr
            500                 505                 510

Asn Met Ser Ser Glu Glu Leu Ala Pro Ile Asn Glu
        515                 520

<210> SEQ ID NO 21
<211> LENGTH: 368
<212> TYPE: PRT
<213> ORGANISM: Homo sapiens

<400> SEQUENCE: 21

Val Leu Val Leu Leu Asn Pro Arg Gly Gly Lys Gly Lys Ala Leu Gln
 1               5                   10                  15

Leu Phe Arg Ser His Val Gln Pro Leu Leu Ala Glu Ala Glu Ile Ser
            20                  25                  30

Phe Thr Leu Met Leu Thr Glu Arg Arg Asn His Ala Arg Glu Leu Val
        35                  40                  45

Arg Ser Glu Glu Leu Gly Arg Trp Asp Ala Leu Val Val Met Ser Gly
    50                  55                  60

Asp Gly Leu Met His Glu Val Val Asn Gly Leu Met Glu Arg Pro Asp
65                  70                  75                  80

Trp Glu Thr Ala Ile Gln Lys Pro Leu Cys Ser Leu Pro Ala Gly Ser
                85                  90                  95

Gly Asn Ala Leu Ala Ala Ser Leu Asn His Tyr Ala Gly Tyr Glu Gln
            100                 105                 110

-continued

```
Val Thr Asn Glu Asp Leu Leu Thr Asn Cys Thr Leu Leu Leu Cys Arg
        115                 120                 125

Arg Leu Leu Ser Pro Met Asn Leu Leu Ser Leu His Thr Ala Ser Gly
        130                 135                 140

Leu Arg Leu Phe Ser Val Leu Ser Leu Ala Trp Gly Phe Ile Ala Asp
145                 150                 155                 160

Val Asp Leu Glu Ser Glu Lys Tyr Arg Arg Leu Gly Glu Met Arg Phe
                165                 170                 175

Thr Leu Gly Thr Phe Leu Arg Leu Ala Ala Leu Arg Thr Tyr Arg Gly
            180                 185                 190

Arg Leu Ala Tyr Leu Pro Val Gly Arg Val Gly Ser Lys Thr Pro Ala
        195                 200                 205

Ser Pro Val Val Val Gln Gln Gly Pro Val Asp Ala His Leu Val Pro
        210                 215                 220

Leu Glu Glu Pro Val Pro Ser His Trp Thr Val Val Pro Asp Glu Asp
225                 230                 235                 240

Phe Val Leu Val Leu Ala Leu Leu His Ser His Leu Gly Ser Glu Met
                245                 250                 255

Phe Ala Ala Pro Met Gly Arg Cys Ala Ala Gly Val Met His Leu Phe
                260                 265                 270

Tyr Val Arg Ala Gly Val Ser Arg Ala Met Leu Leu Arg Leu Phe Leu
            275                 280                 285

Ala Met Glu Lys Gly Arg His Met Glu Tyr Glu Cys Pro Tyr Leu Val
        290                 295                 300

Tyr Val Pro Val Val Ala Phe Arg Leu Glu Pro Lys Asp Gly Lys Gly
305                 310                 315                 320

Val Phe Ala Val Asp Gly Glu Leu Met Val Ser Glu Ala Val Gln Gly
                325                 330                 335

Gln Val His Pro Asn Tyr Phe Trp Met Val Ser Gly Cys Val Glu Pro
            340                 345                 350

Pro Pro Ser Trp Lys Pro Gln Gln Met Pro Pro Pro Glu Glu Pro Leu
        355                 360                 365
```